(12) United States Patent
Kong et al.

(10) Patent No.: US 12,173,304 B2
(45) Date of Patent: Dec. 24, 2024

(54) INTRON FRAGMENTS

(71) Applicant: NEURACLE GENETICS INC., Seoul (KR)

(72) Inventors: Hoon Young Kong, Seoul (KR); Jong-Mook Kim, Seoul (KR); Jee Yong Kim, Gwacheon-si (KR); Sunhwa Shin, Seoul (KR); Kyungwon Lee, Ansan-si (KR); Joo Seok Han, Seoul (KR)

(73) Assignee: NEURACLE GENETICS INC., Seoul (KR)

( * ) Notice: Subject to any disclaimer, the term of this patent is extended or adjusted under 35 U.S.C. 154(b) by 0 days.

(21) Appl. No.: 17/365,884

(22) Filed: Jul. 1, 2021

(65) Prior Publication Data
US 2022/0010332 A1    Jan. 13, 2022

(30) Foreign Application Priority Data

Jul. 8, 2020  (KR) .................... 10-2020-0084038

(51) Int. Cl.
*C12N 15/85* (2006.01)
*C12N 15/113* (2010.01)
*C12N 15/86* (2006.01)

(52) U.S. Cl.
CPC .......... *C12N 15/85* (2013.01); *C12N 15/113* (2013.01); *C12N 15/86* (2013.01); *C12N 2310/11* (2013.01); *C12N 2310/141* (2013.01); *C12N 2710/16622* (2013.01); *C12N 2750/14143* (2013.01); *C12N 2830/15* (2013.01); *C12N 2830/42* (2013.01); *C12N 2830/48* (2013.01); *C12N 2830/60* (2013.01); *C12N 2840/445* (2013.01)

(58) Field of Classification Search
CPC . C12N 15/86; C12N 2830/15; C12N 2830/42
See application file for complete search history.

(56) References Cited

U.S. PATENT DOCUMENTS

| | | | | |
|---|---|---|---|---|
| 2003/0166251 A1* | 9/2003 | Kim | ................... | C12N 15/86 435/235.1 |
| 2011/0165191 A1* | 7/2011 | Ranga | ................... | A61K 39/12 435/320.1 |
| 2011/0301226 A1 | 12/2011 | Mendell et al. | | |
| 2015/0361451 A1* | 12/2015 | Le Fourn | ............... | C12N 15/90 435/375 |
| 2020/0237821 A1* | 7/2020 | Kwon | .................... | C07K 16/28 |

FOREIGN PATENT DOCUMENTS

| | | | |
|---|---|---|---|
| JP | 2004508047 A | 3/2004 | |
| WO | WO-2009139004 A2 | 11/2009 | |
| WO | WO-2018170473 A1 * | 9/2018 | ............ A61K 48/00 |
| WO | WO-2018187363 A1 | 10/2018 | |
| WO | WO-2020032784 A1 * | 2/2020 | ............ A61K 35/17 |
| WO | WO-2020106916 A1 | 5/2020 | |

OTHER PUBLICATIONS

Wang et al. Enhanced transgene expression using cis-acting elements combined with the EF1 promoter in a mammalian expression system. European Journal of Pharmaceutical Sciences, vol. 123, pp. 539-545, and pp. 1/5-5/5 of Supplement, 2018. (Year: 2018).*

Wakabayashi-Ito et al. Characterization of regulatory elements in the promoter of the human elongation factor-1alpha gene. The Journal of Biological Chemistry, vol. 269, No. 47, pp. 29831-29837, 1994. (Year: 1994).*

Green, M.R. Biochemical mechanisms of constitutive and regulated pre-mRNA splicing. Annual Review of Cell Biology, vol. 7, pp. 559-599, 1991. (Year: 1991).*

Riethoven, JM. Regulatory regions in DNA: promoters, enhancers, silencers, and insulators. Methods in Molecular Biology, vol. 674, pp. 33-42, Jan. 2010. (Year: 2010).*

Brinster, R.L., et al., "Introns increase transcriptional efficiency in transgenic mice," Proc. Natl. Acad. Sci. 85:836-840, United States National Academy of Sciences, United States (Feb. 1988).

Huh, G.S., et al., "Regulation of alternative pre-mRNA splicing by a novel repeated hexanucleotide element," Genes & Development 8:1561-1574, Colspring Harbor Laboratory Press, United States (Jul. 1994).

Muzyczka, N., "Use of Adeno-Associated Virus as a General Transduction Vector for Mammalian Cells," Current Topics in Microbiology and Immunology 158: 98-129, Springer-Verlag, Germany (1992).

Parenteau, J., et al., "Introns are mediators of cell response to starvation," Nature 565: 612-617, Springer Nature Limited, United States (Jan. 2019).

Parenteau, J., et al., "Introns within Ribosomal Protein Genes Regulate the Production and Function of Yeast Ribosomes," Cell 147:320-331, Elsevier, Netherlands (Oct. 2011).

Samulski, R.J., et al., "AAV-Mediated Gene Therapy for Research and Therapeutic Purposes," Annual Review of Virology 1: 427-451, Annual Reviews, United States (Nov. 2014).

GenBank, "Cloning vector pAAV-EF1alpha-hFAH.AOS2, complete sequence," Accession No. EF203084.1, accessed at URL:[https://www.ncbi.nlm.nih.gov/nuccore/124109384] on Sep. 7, 2022, 3 pages, National Library of Medicine, United States (Jan. 2007).

(Continued)

*Primary Examiner* — Jennifer Dunston
(74) *Attorney, Agent, or Firm* — Sterne, Kessler, Goldstein & Fox P.L.L.C.

(57) ABSTRACT

Novel intron fragments are provided. The intron fragments can increase gene expression to levels equal to or higher than those achieved by the full-length intron while maintaining their ability to increase gene expression even when combined with various types of promoters and splicing donors. Particularly, the intron fragments enable loading of larger transgenes when used in genetic information delivery systems whose size is limited, for example, adeno-associated viruses (AAVs) and rhabdoviruses. Therefore, the use of the intron fragments is expected to extend the range of therapeutic genes.

17 Claims, 15 Drawing Sheets
Specification includes a Sequence Listing.

(56) References Cited

OTHER PUBLICATIONS

Kim, S.-Y., et al., "The human elongation factor 1 alpha (EF-1 alpha) first intron highly enhances expression of foreign genes from the murine cytomegalovirus promoter," Journal of Biotechnology 93(2):183-187, Elsevier, Netherlands (Feb. 2002).

Lu, J., et al., "A 5' Noncoding Exon Containing Engineered Intron Enhances Transgene Expression from Recombinant AAV Vectors in vivo," Hum Gene Ther 28(1):125-134, Mary Ann Liebert Inc., United States (Jan. 2017).

Nakai, H., et al., "Increasing the size of rAAV-mediated expression cassettes in vivo by intermolecular joining of two complementary vectors," Nat Biotechnol 18(5):527-532, Nature Publishing Group, United Kingdom (May 2000).

Clark, K., "Recent advances in recombinant adeno-associated virus vector production," Kidney Int 61(1 Suppl):S9-15, Elsevier, Netherlands (Jan. 2002).

Clement, N., and Grieger, J., "Manufacturing of recombinant adeno-associated viral vectors for clinical trials," Mol Ther Methods Clin Dev 3:16002, Cell Press, United States (Mar. 2016).

Fields, B., et al., Fields Virology, 4th edition vol. 2, Chapter 69:2327-2359, Lippincott-Raven Publishers, United States (2001).

Gao, G., et al., "Clades of Adeno-associated viruses are widely disseminated in human tissues," J Virol 78(12):6381-6388, American Society for Microbiology, United States (Jun. 2004).

Mori, S., et al., "Two novel adeno-associated viruses from cynomolgus monkey: pseudotyping characterization of capsid protein," Virology 330(2):375-383, Academic Press Inc., United States (Dec. 2004).

Scaggiante, B., and Bosutti, A., "EEF1A1 (eukaryotic translation elongation factor 1 alpha 1)," Atlas Genet Cytogenet Oneal Haematol 19(4):256-265, France (Mar. 2015).

Xiao, X., et al., "Production of high-titer recombinant adeno-associated virus vectors in the absence of helper adenovirus," J Virol 72(3):2224-2232, American Society for Microbiology, United States (Mar. 1998).

\* cited by examiner

INTRON FRAGMENTS

CROSS-REFERENCE TO RELATED APPLICATIONS

This application claims the priority benefit of Koran Patent Application No. 10-2020-0084038, filed on Jul. 8, 2020, the contents of which is hereby incorporated by reference in its entirety.

REFERENCE TO SEQUENCE LISTING SUBMITTED ELECTRONICALLY

The content of the electronically submitted sequence listing in ASCII text file (Name: 4265_0020001_SeqListing_ST25.txt; Size: 24,515 bytes; and Date of Creation: Sep. 7, 2022) filed with the application is incorporated herein by reference in its entirety.

FIELD OF THE DISCLOSURE

The present disclosure relates to novel intron fragments (i.e., untranslated nucleic acid sequences) that can increase transgene expression.

BACKGROUND OF THE DISCLOSURE

Eukaryotic pre-mRNAs consist of exons containing actual genetic information and introns intervening between the exons and have poly A sequences at their 3' ends. Introns affect alternative mRNA splicing and regulate protein production (Huh, G. S., et al., "Regulation of Alternative pre-mRNA Splicing by a Novel Repeated Hexanucleotide Element," *Genes Dev* 8(13):1561-74 (July 1994); Parenteau, J., et al., "Introns Within Ribosomal Protein Genes Regulate the Production and Function of Yeast Ribosomes," *Cell* 147(2):320-31 (October 2011)). It has also been reported that intron-containing transgenes in mice are transcribed 10- to 100-fold more efficiently than the same genes lacking introns without and even affect the survival of mice (Brinster, R. L., et al., "Introns Increase Transcriptional Efficiency in Transgenic Mice," *Proc. Natl. Acad. Sci. USA*. 85(3):836-40 (February 1988); Parenteau, J., et al., "Introns Are Mediators of Cell Response to Starvation," *Nature* 565 (7741):612-617 (January 2019)). Particularly, introns enhance protein production by a mechanism called intron-mediated enhancement (IME). Most introns used to gain the IME effect are quite long, limiting their actual use. For example, since adeno-associated viruses (AAVs), which have recently attracted attention as vectors for gene therapy, can carry only genetic information with a length of up to 4.7 kbp, the use of long introns greatly restricts the range of genes that can be delivered. Therefore, short intron fragments, including those that can be used with AAV vectors while retaining their ability to increase protein expression, is highly desirable.

SUMMARY OF THE DISCLOSURE

Provided herein is an isolated polynucleotide comprising an untranslated nucleic acid sequence having at least about 70%, at least about 80%, at least about 85%, at least about 90%, at least about 95%, at least about 96%, at least about 97%, at least about 98%, at least about 99%, or about 100% sequence identity to nucleotides 874 to 924 of SEQ ID NO: 1, wherein the untranslated nucleic acid sequence does not comprise SEQ ID NO: 1. In some aspects, the untranslated nucleic acid sequence comprises the nucleotide sequence set forth in SEQ ID NO: 57. In some aspects, the untranslated nucleic acid sequence consists of the nucleotide sequence set forth in SEQ ID NO: 57.

Provided herein is an isolated polynucleotide comprising an untranslated nucleic acid sequence having at least about 70%, at least about 80%, at least about 85%, at least about 90%, at least about 95%, at least about 96%, at least about 97%, at least about 98%, at least about 99%, or about 100% sequence identity to nucleotides 852-924 of SEQ ID NO: 1, wherein the untranslated nucleic acid sequence does not comprise SEQ ID NO: 1. In some aspects, the untranslated nucleic acid sequence comprises the nucleotide sequence set forth in SEQ ID NO: 3. In some aspects, wherein the untranslated nucleic acid sequence consists of the nucleotide sequence set forth in SEQ ID NO: 3.

Provided herein is an isolated polynucleotide comprising an untranslated nucleic acid sequence having at least about 70%, at least about 80%, at least about 85%, at least about 90%, at least about 95%, at least about 96%, at least about 97%, at least about 98%, at least about 99%, or about 100% sequence identity to nucleotides 830-924 of SEQ ID NO: 1, wherein the untranslated nucleic acid sequence does not comprise SEQ ID NO: 1. In some aspects, the untranslated nucleic acid sequence comprises the nucleotide sequence set forth in SEQ ID NO: 2. In some aspects, the untranslated nucleic acid sequence consists of the nucleotide sequence set forth in SEQ ID NO: 2.

In some aspects, a polynucleotide described herein comprises at least one, at least two, at least three, at least five, at least about 10, at least about 15, at least about 20, at least about 25, at least about 30, at least about 40, at least about 50, at least about 60, at least about 70, at least about 80, at least about 90, or at least about 100 additional nucleotides at the 5' terminus ("5' region") of the untranslated nucleic acid sequence. In some aspects, the polynucleotide comprises one or more contiguous or non-contiguous nucleotides corresponding to positions 1 to 873 in SEQ ID NO: 1 at the 5' region of the untranslated nucleic acid sequence. In some aspects, a polynucleotide described herein comprises at least one, at least two, at least three, at least five, at least about 10, at least about 15, at least about 20, at least about 25, at least about 30, at least about 40, at least about 50, at least about 60, at least about 70, at least about 80, at least about 90, or at least about 100 additional nucleotides at the 3' terminus ("3' region") of the untranslated nucleic acid sequence.

In some aspects, the untranslated nucleic acid sequence of a polynucleotide described herein has at least about 70%, at least about 80%, at least about 85%, at least about 90%, at least about 95%, at least about 96%, at least about 97%, at least about 98%, at least about 99%, or about 100% sequence identity to (i) nucleotides 871 to 924 of SEQ ID NO: 1 (i.e., SEQ ID NO: 58), (ii) nucleotides 861 to 924 of SEQ ID NO: 1 (i.e., SEQ ID NO: 59), (iii) nucleotides 852 to 924 of SEQ ID NO: 1 (i.e., SEQ ID NO: 60), (iv) nucleotides 851 to 924 of SEQ ID NO: 1 (i.e., SEQ ID NO: 61), (v) nucleotides 830 to 924 of SEQ ID NO: 1 (i.e., SEQ ID NO: 2), (vi) nucleotides 821 to 924 of SEQ ID NO: 1 (i.e., SEQ ID NO: 63), (vii) nucleotides 811 to 924 of SEQ ID NO: 1 (i.e., SEQ ID NO: 64), (viii) nucleotides 808 to 924 of SEQ ID NO: 1 (i.e., SEQ ID NO: 65), (ix) nucleotides 801 to 924 of SEQ ID NO: 1 (i.e., SEQ ID NO: 66), (x) nucleotides 751 to 924 of SEQ ID NO: 1 (i.e., SEQ ID NO: 67), (xi) nucleotides 721 to 924 of SEQ ID NO: 1 (i.e., SEQ ID NO: 68), (xii) nucleotides 701 to 924 of SEQ ID NO: 1 (i.e., SEQ ID NO: 69), (xii) nucleotides 651 to 924 of SEQ ID NO: 1 (i.e., SEQ ID NO: 70), (xiii) nucleotides 601 to 924 of SEQ ID NO: 1 (i.e., SEQ ID NO: 71), (xiv) nucleotides 570 to 924 of SEQ ID NO: 1 (i.e., SEQ ID NO: 72), (xv) nucleotides 551 to 924 of SEQ ID NO: 1 (i.e., SEQ ID NO; 73), or (xvi) nucleotides 501 to 924 of SEQ ID NO: 1 (i.e., SEQ ID NO: 74).

In some aspects, a polynucleotide described herein further comprises a transgene. In some aspects, the transgene is capable of being translated into a polypeptide.

In some aspects, the untranslated nucleic acid sequence of a polynucleotide described herein is capable of increasing the expression of the transgene when translated, compared to a reference expression, wherein the reference expression comprises the expression of the corresponding transgene when translated in the absence of the untranslated nucleic acid sequence and/or in the presence of a nucleotide sequence comprising the nucleotide sequence set forth in SEQ ID NO: 1. In some aspects, the untranslated nucleic acid sequence is capable of increasing the expression of the transgene by at least about 1 fold, at least about 1.1 fold, at least about 1.2 fold, at least about 1.3 fold, at least about 1.4 fold, at least about 1.5 fold, at least about 1.6 fold, at least about 1.7 fold, at least about 1.8 fold, at least about 1.9 fold, at least about 2 fold, at least about 2.5 fold, at least about 3 fold, at least about 3.5 fold, at least about 4 fold, at least about 5 fold, at least about 6 fold, at least about 7 fold, at least about 8 fold, at least about 9 fold, or at least about 10 fold more than the reference expression.

In some aspects, a polynucleotide described herein further comprises a promoter. In some aspects, the promoter comprises a cytomegalovirus (CMV) promoter, an EF-1α promoter, a β-actin promoter, a GAPDH promoter, a HSP70 promoter, a GRP78 promoter, an eIF4a promoter, an AAT promoter, a TTR promoter, a GFAP promoter, a SV40 promoter, a SYN1 promoter, a GRK promoter, a Rho promoter, or any combination thereof.

In some aspects, the promoter is an EF-1α promoter. In some aspects, the EF-1α promoter comprises a sequence having at least about 70%, at least about 80%, at least about 85%, at least about 90%, at least about 95%, at least about 96%, at least about 97%, at least about 98%, at least about 99%, or about 100% sequence identity to the nucleotide sequence set forth in SEQ ID NO: 7. In some aspects, the promoter comprises a CMV promoter. In some aspects, the CMV promoter comprises a sequence having at least about 70%, at least about 80%, at least about 85%, at least about 90%, at least about 95%, at least about 96%, at least about 97%, at least about 98%, at least about 99%, or about 100% sequence identity to the nucleotide sequence set forth in SEQ ID NO: 5 or 6. In some aspects, the promoter comprises a β-actin promoter. In some aspects, the β-actin promoter comprises a sequence having at least about 70%, at least about 80%, at least about 85%, at least about 90%, at least about 95%, at least about 96%, at least about 97%, at least about 98%, at least about 99%, or about 100% sequence identity to the nucleotide sequence set forth in SEQ ID NO: 8.

In some aspects, a polynucleotide described herein further comprises an enhancer. In some aspects, the enhancer comprises a cytomegalovirus (CMV) enhancer, a SV40 early enhancer, an adenovirus 5 E1A enhancer, a HBV enhancer-1 regulatory region (Eh-1), a HPV-16 or -18 E6/7 long control region (LCR), a HIV-1 long terminal repeat (LTR), or any combination thereof. In some aspects, the enhancer is a CMV enhancer. In some aspects, the CMV enhancer comprises a sequence having at least about 70%, at least about 80%, at least about 85%, at least about 90%, at least about 95%, at least about 96%, at least about 97%, at least about 98%, at least about 99%, or about 100% sequence identity to the nucleotide sequence set forth in SEQ ID NO: 4.

In some aspects, a polynucleotide described herein further comprises a splicing donor sequence. In some aspects, the splicing donor sequence is linked upstream of the untranslated nucleic acid sequence. In some aspects, the splicing donor sequence comprises a sequence having at least about 70%, at least about 80%, at least about 85%, at least about 90%, at least about 95%, at least about 96%, at least about 97%, at least about 98%, at least about 99%, or about 100% sequence identity to the nucleotide sequence set forth in SEQ ID NO: 9 or 10.

In some aspects, a polynucleotide described herein further comprises an EF-1α exon 2 (E2) nucleotide sequence. In some aspects, the EF-1α exon 2 (E2) nucleotide sequence has at least about 70%, at least about 80%, at least about 85%, at least about 90%, at least about 95%, at least about 96%, at least about 97%, at least about 98%, at least about 99%, or about 100% sequence identity to the nucleotide sequence set forth in SEQ ID NO: 11.

In some aspects, a polynucleotide described herein further comprises a cytomegalovirus (CMV) exon 1 (E1) sequence, a EF-1α E1 sequence, a β-actin E1 sequence, or any combination thereof. In some aspects, the CMV E1 sequence has at least about 70%, at least about 80%, at least about 85%, at least about 90%, at least about 95%, at least about 96%, at least about 97%, at least about 98%, at least about 99%, or about 100% sequence identity to the nucleotide sequence set forth in SEQ ID NO: 12. In some aspects, the EF-1α E1 sequence has at least about 70%, at least about 80%, at least about 85%, at least about 90%, at least about 95%, at least about 96%, at least about 97%, at least about 98%, at least about 99%, or about 100% sequence identity to the nucleotide sequence set forth in SEQ ID NO: 13. In some aspects, the β-actin E1 sequence has at least about 70%, at least about 80%, at least about 85%, at least about 90%, at least about 95%, at least about 96%, at least about 97%, at least about 98%, at least about 99%, or about 100% sequence identity to the nucleotide sequence set forth in SEQ ID NO: 14 or 15.

In some aspects, a polynucleotide described herein further comprises at least one target sequence for a microRNA (miRNA) specific to an immune cell. In some aspects, the miRNA comprises miR142-3p, miR142-5p, or both. In some aspects, the target sequence for a miRNA comprises an antisense oligonucleotide, an antagomir, a small hairpin RNA (shRNA) molecule, a small interfering RNA (siRNA) molecule, a ribozyme, a peptide nucleic acid (PNA) oligonucleotide, a locked nucleic acid (LNA) oligonucleotide, or any combination thereof. In some aspects, the target sequence for a miRNA is complementary to the full-length or partial sequence of miR142-3p or miR142-5p. In some aspects, the target sequence for a miRNA comprises the nucleotide sequence set forth in SEQ ID NO: 16 or SEQ ID NO: 17.

In some aspects, a polynucleotide described herein comprises at least two target sequences, at least three target sequences, at least four target sequences, at least five target sequences, at least six target sequences, at least seven target sequences, at least eight target sequences, at least nine target sequences, or at least ten target sequences. In some aspects, two or more of the target sequences are the same. In some aspects, each of the target sequences are different.

In some aspects, a polynucleotide described herein further comprises a woodchuck hepatitis virus posttranscriptional regulatory element (WPRE) sequence. In some aspects, the WPRE sequence has at least about 70%, at least about 80%, at least about 85%, at least about 90%, at least about 95%, at least about 96%, at least about 97%, at least about 98%, at least about 99%, or about 100% sequence identity to the nucleotide sequence set forth in SEQ ID NO: 18.

In some aspects, a polynucleotide described herein further comprises one or more polyadenylation (pA) sequences. In some aspects, the pA sequence has at least about 70%, at least about 80%, at least about 85%, at least about 90%, at least about 95%, at least about 96%, at least about 97%, at least about 98%, at least about 99%, or about 100% sequence identity to the nucleotide sequence set forth in any one of SEQ ID NOs: 19 to 22.

Where the polynucleotide comprises a transgene, in some aspects, the transgene encodes a wild type polypeptide or any variant thereof, a fusion protein, an antibody or an antigen-binding fragment thereof, a RNA-based molecule, or any combination thereof. In some aspects, the transgene comprises a nucleotide sequence which has at least about 70%, at least about 80%, at least about 85%, at least about 90%, at least about 95%, at least about 96%, at least about 97%, at least about 98%, at least about 99%, or about 100% sequence identity to the nucleotide sequence set forth in SEQ ID NO: 23. In some aspects, the transgene encodes a fusion protein. In some aspects, the fusion protein comprises an inhibitor of a vascular endothelial growth factor ("VEGF"). In some aspects, the inhibitor of VEGF comprises aflibercept. Where the transgene is a RNA-based molecule, in some aspects, the RNA-based molecule comprises a miRNA, a shRNA, a siRNA, a ribozyme, or any combination thereof.

In some aspects, a polynucleotide described herein is a recombinant expression construct.

Also provided herein is a polynucleotide comprising (i) a transgene and (ii) a control element operably linked to the transgene, wherein the control element comprises (from 5' to 3'): (1) the CMV enhancer set forth in SEQ ID NO: 4; (2) a promoter selected from the CMV promoter sequence set forth in SEQ ID NO: 5 or 6, the EF-1α promoter sequence set forth in SEQ ID NO: 7, or the chicken β-actin promoter sequence set forth in SEQ ID NO: 8; (3) an exon 1 (E1) sequence selected from the CMV E1 sequence set forth in SEQ ID NO: 12, the EF-1α E1 sequence set forth in SEQ ID NO: 13, or the chicken β-actin E1 sequence set forth in SEQ ID NO: 14 or 15; (4) the splicing donor sequence set forth in SEQ ID NO: 9 or 10; (5) an untranslated nucleic acid sequence comprising, consisting essentially of, or consisting of the nucleotide sequence set forth in SEQ ID NO: 2, SEQ ID NO: 3, or SEQ ID NO: 57; and (6) the EF-1α E2 sequence set forth in SEQ ID NO: 11.

Provided herein is a vector comprising any of the polynucleotides of the present disclosure. In some aspects, the vector is a viral vector. In some aspects, the viral vector comprises an adenovirus (e.g., genetic engineered adenovirus), an adeno-associated virus (AAV), a lentivirus, a SV40-type virus, a polyomavirus, an Epstein-Barr virus, a papilloma virus, a herpes simplex virus (HSV), a vaccinia virus, a polio virus, a baculovirus, a retrovirus, a poxvirus, or any combination thereof. In some aspects, the viral vector is an AAV.

In some aspects, a viral vector described herein is for use in a gene therapy. In some aspects, a viral vector is for use in expressing the polypeptide encoded by the transgene of a polynucleotide described herein. In some aspects, the transgene comprises the nucleotide sequence set forth in SEQ ID NO: 23.

Provided herein is a cell comprising any of the polynucleotides or vectors described herein.

Also provided herein is a method for producing a recombinant virus particle comprising transducing a cell with any of the vectors described herein and a construct containing the rep and cap genes. In some aspects, the method further comprises isolating the produced recombinant virus particle.

Provided herein is a recombinant virus particle produced by the above methods. Also provided herein is a recombinant virus particle comprising (a) a capsid protein and (b) any of the vectors described herein. In some aspects, the recombinant virus particle is an adeno-associated virus (AVV). In some aspects, the serotype of the AAV is AAV1, AAV2, AAV3, AAV4, AAV5, AAV6, AAV7, AAV8, AAV9 or AAVrh10. In some aspects, the serotype of the AAV is AAV2. In some aspects, the serotype of the AAV is AAV8. In some aspects, the serotype of the AAV is AAV5. In some aspects, the serotype of the AAV is AAV9.

Present disclosure further provides a pharmaceutical composition comprising (a) any of the polynucleotides, vectors, cells, or recombinant virus particles described herein; and (b) a pharmaceutically acceptable excipient.

Also provided herein is a pharmaceutical composition comprising a recombinant adeno-associated virus particle and a pharmaceutically acceptable carrier, wherein the recombinant adeno-associated virus particle comprises (a) an AAV type 8 capsid protein and (b) a polynucleotide comprising (i) a transgene, which comprises the nucleotide sequence set forth in SEQ ID NO: 23, and (ii) a control element operably linked to the transgene, wherein the control element comprises (from 5' to 3'): (1) the cytomegalovirus (CMV) enhancer sequence set forth in SEQ ID NO: 4; (2) the chicken β-actin promoter sequence set forth in SEQ ID NO: 8; (3) the chicken β-actin exon 1 (E1) sequence set forth in SEQ ID NO: 15; (4) the splicing donor sequence of the chicken β-actin intron set forth in SEQ ID NO: 10; (5) an untranslated nucleic acid sequence comprising, consisting essentially of, or consisting of the nucleotide sequence set forth in SEQ ID NO: 2, SEQ ID NO: 3, or SEQ ID NO: 57; and (6) the EF-1α exon 2 (E2) sequence set forth in SEQ ID NO: 11.

Provided herein is a pharmaceutical composition for preventing or treating an ophthalmic disease comprising a recombinant adeno-associated virus particle and a pharmaceutically acceptable carrier, wherein the recombinant adeno-associated virus particle comprises (a) an AAV type 8 capsid protein and (b) a polynucleotide comprising (i) a transgene, which comprises the nucleotide sequence set forth in SEQ ID NO: 23, and (ii) a control element operably linked to the transgene, wherein the control element comprises (from 5' to 3'): (1) the cytomegalovirus (CMV) enhancer sequence set forth in SEQ ID NO: 4; (2) the chicken β-actin promoter sequence set forth in SEQ ID NO: 8; (3) the chicken β-actin exon 1 (E1) sequence set forth in SEQ ID NO: 15; (4) the splicing donor sequence of the chicken β-actin intron set forth in SEQ ID NO: 10; (5) an untranslated nucleic acid sequence comprising, consisting essentially of, or consisting of the nucleotide sequence set forth in SEQ ID NO: 2, SEQ ID NO: 3, or SEQ ID NO: 57; and (6) the EF-1α exon 2 (E2) sequence set forth in SEQ ID NO: 11.

In some aspects, the ophthalmic disease comprises a diabetic retinopathy, a choroidal neovascularization, a macular degeneration, a retinal degeneration, a macular edema, a retinal edema, a *Macula tumentia*, or combinations thereof. In some aspects, the macuclar degeneration comprises age-related macular degeneration (AMD).

Provided herein is a method of increasing the expression of a transgene in a cell, comprising contacting the cell with any of the polynucleotides, vectors, or recombinant virus particles described herein. In some aspects, the contacting occurs in vivo. In some aspects, the method comprises administering the polynucleotide, the vector, or the recombinant virus particle to the subject prior to the contacting. In some aspects, the contacting occurs ex vivo. In some aspects, the expression of the transgene is increased by at least about 1 fold, at least about 1.1 fold, at least about 1.2 fold, at least about 1.3 fold, at least about 1.4 fold, at least about 1.5 fold, at least about 1.6 fold, at least about 1.7 fold, at least about 1.8 fold, at least about 1.9 fold, at least about 2 fold, at least about 2.5 fold, at least about 3 fold, at least about 3.5 fold, at least about 4 fold, at least about 5 fold, at least about 6 fold, at least about 7 fold, at least about 8 fold, at least about 9 fold, or at least about 10 fold or more, compared to the corresponding expression in a reference cell, wherein the reference cell is contacted with a polynucleotide, vector, or recombinant virus particle that either lack the untranslated nucleic acid sequence or comprises the nucleotide sequence set forth in SEQ ID NO: 1.

Provided herein is a method of treating a disease or disorder in a subject in need thereof, comprising administering to the subject any of the polynucleotides, vectors, or recombinant virus particles described herein. In some aspects, the disease or disorder comprises an ophthalmic disease. In some aspects, the ophthalmic disease comprises a diabetic retinopathy, a choroidal neovascularization, a macular degeneration, a retinal degeneration, a macular edema, a retinal edema, a *Macula tumentia*, or combinations thereof. In some aspects, the macuclar degeneration comprises age-related macular degeneration (AMD). In some aspects, the method comprises administering to the subject an additional therapeutic agent.

Aspects

Aspect 1. An elongation factor-1 alpha (EF-1α) intron fragment for transgene expression comprising a sequence in which contiguous or non-contiguous ones of the nucleotides in the EF-1α intron sequence set forth in SEQ ID NO: 1 are truncated, wherein (a) the EF-1α intron fragment essentially comprises the nucleotides at positions 874 to 924 in the sequence set forth in SEQ ID NO: 1 and (b) the EF-1α intron fragment increases transgene expression when present in an expression construct compared to an intron fragment consisting only of the nucleotides at positions 874 to 924 in the sequence set forth in SEQ ID NO: 1.

Aspect 2. The EF-1α intron fragment according to aspect 1, wherein the truncation of contiguous or non-contiguous nucleotides comprises truncation of contiguous ones of the nucleotides at positions 1 to 873 in the sequence set forth in SEQ ID NO: 1, truncation of non-contiguous nucleotides remaining untruncated between the truncated nucleotides or insertion of different types of nucleotides into positions of the truncated contiguous or non-contiguous nucleotides.

Aspect 3. The EF-1α intron fragment according to aspect 2, wherein the truncation of contiguous or non-contiguous nucleotides comprises truncation of contiguous ones of the nucleotides at positions 1 to 870 in the sequence set forth in SEQ ID NO: 1, truncation of non-contiguous nucleotides remaining untruncated between the truncated nucleotides or insertion of different types of nucleotides into positions of the truncated contiguous or non-contiguous nucleotides.

Aspect 4. The EF-1α intron fragment according to aspect 3, wherein the truncation of contiguous or non-contiguous nucleotides comprises truncation of contiguous ones of the nucleotides at positions 1 to 860 in the sequence set forth in SEQ ID NO: 1, truncation of non-contiguous nucleotides remaining untruncated between the truncated nucleotides or insertion of different types of nucleotides into positions of the truncated contiguous or non-contiguous nucleotides.

Aspect 5. The EF-1α intron fragment according to aspect 4, wherein the truncation of contiguous or non-contiguous nucleotides comprises truncation of contiguous ones of the nucleotides at positions 1 to 851 in the sequence set forth in SEQ ID NO: 1, truncation of non-contiguous nucleotides remaining untruncated between the truncated nucleotides or insertion of different types of nucleotides into positions of the truncated contiguous or non-contiguous nucleotides.

Aspect 6. The EF-1α intron fragment according to aspect 5, wherein the truncation of contiguous or non-contiguous nucleotides comprises truncation of contiguous ones of the nucleotides at positions 1 to 850 in the sequence set forth in SEQ ID NO: 1, truncation of non-contiguous nucleotides remaining untruncated between the truncated nucleotides or insertion of different types of nucleotides into positions of the truncated contiguous or non-contiguous nucleotides.

Aspect 7. The EF-1α intron fragment according to aspect 6, wherein the truncation of contiguous or non-contiguous nucleotides comprises truncation of contiguous ones of the nucleotides at positions 1 to 829 in the sequence set forth in SEQ ID NO: 1, truncation of non-contiguous nucleotides remaining untruncated between the truncated nucleotides or insertion of different types of nucleotides into positions of the truncated contiguous or non-contiguous nucleotides.

Aspect 8. The EF-1α intron fragment according to aspect 7, wherein the truncation of contiguous or non-contiguous nucleotides comprises truncation of contiguous ones of the nucleotides at positions 1 to 820 in the sequence set forth in SEQ ID NO: 1, truncation of non-contiguous nucleotides remaining untruncated between the truncated nucleotides or insertion of different types of nucleotides into positions of the truncated contiguous or non-contiguous nucleotides.

Aspect 9. The EF-1α intron fragment according to aspect 8, wherein the truncation of contiguous or non-contiguous nucleotides comprises truncation of contiguous ones of the nucleotides at positions 1 to 810 in the sequence set forth in SEQ ID NO: 1, truncation of non-contiguous nucleotides remaining untruncated between the truncated nucleotides or insertion of different types of nucleotides into positions of the truncated contiguous or non-contiguous nucleotides.

Aspect 10. The EF-1α intron fragment according to aspect 9, wherein the truncation of contiguous or non-contiguous nucleotides comprises truncation of contiguous ones of the nucleotides at positions 1 to 800 in the sequence set forth in SEQ ID NO: 1, truncation of non-contiguous nucleotides remaining untruncated between the truncated nucleotides or insertion of different types of nucleotides into positions of the truncated contiguous or non-contiguous nucleotides.

Aspect 11. The EF-1α intron fragment according to aspect 10, wherein the truncation of contiguous or non-contiguous nucleotides comprises truncation of contiguous ones of the nucleotides at positions 1 to 750 in the sequence set forth in SEQ ID NO: 1, truncation of non-contiguous nucleotides remaining untruncated between the truncated nucleotides or insertion of different types of nucleotides into positions of the truncated contiguous or non-contiguous nucleotides.

Aspect 12. The EF-1α intron fragment according to aspect 11, wherein the truncation of contiguous or non-contiguous nucleotides comprises truncation of contiguous ones of the nucleotides at positions 1 to 720 in the sequence set forth in SEQ ID NO: 1, truncation of non-contiguous nucleotides remaining untruncated between the truncated nucleotides or insertion of different types of nucleotides into positions of the truncated contiguous or non-contiguous nucleotides.

Aspect 13. The EF-1α intron fragment according to aspect 12, wherein the truncation of contiguous or non-contiguous nucleotides comprises truncation of contiguous ones of the nucleotides at positions 1 to 700 in the sequence set forth in SEQ ID NO: 1, truncation of non-contiguous nucleotides remaining untruncated between the truncated nucleotides or insertion of different types of nucleotides into positions of the truncated contiguous or non-contiguous nucleotides.

Aspect 14. The EF-1α intron fragment according to aspect 13, wherein the truncation of contiguous or non-contiguous nucleotides comprises truncation of contiguous ones of the nucleotides at positions 1 to 650 in the sequence set forth in SEQ ID NO: 1, truncation of non-contiguous nucleotides remaining untruncated between the truncated nucleotides or insertion of different types of nucleotides into positions of the truncated contiguous or non-contiguous nucleotides.

Aspect 15. The EF-1α intron fragment according to aspect 14, wherein the truncation of contiguous or non-contiguous nucleotides comprises truncation of contiguous ones of the nucleotides at positions 1 to 600 in the sequence set forth in SEQ ID NO: 1, truncation of non-contiguous nucleotides remaining untruncated between the truncated nucleotides or insertion of different types of nucleotides into positions of the truncated contiguous or non-contiguous nucleotides.

Aspect 16. The EF-1α intron fragment according to aspect 15, wherein the truncation of contiguous or non-contiguous nucleotides comprises truncation of contiguous ones of the nucleotides at positions 1 to 569 in the sequence set forth in SEQ ID NO: 1, truncation of non-contiguous nucleotides remaining untruncated between the truncated nucleotides or insertion of different types of nucleotides into positions of the truncated contiguous or non-contiguous nucleotides.

Aspect 17. The EF-1α intron fragment according to aspect 16, wherein the truncation of contiguous or non-contiguous nucleotides comprises truncation of contiguous ones of the nucleotides at positions 1 to 550 in the sequence set forth in SEQ ID NO: 1, truncation of non-contiguous nucleotides remaining untruncated between the truncated nucleotides or insertion of different types of nucleotides into positions of the truncated contiguous or non-contiguous nucleotides.

Aspect 18. The EF-1α intron fragment according to aspect 17, wherein the truncation of contiguous or non-contiguous nucleotides comprises truncation of contiguous ones of the nucleotides at positions 1 to 500 in the sequence set forth in SEQ ID NO: 1, truncation of non-contiguous nucleotides remaining untruncated between the truncated nucleotides or insertion of different types of nucleotides into positions of the truncated contiguous or non-contiguous nucleotides.

Aspect 19. The EF-1α intron fragment according to aspect 7, wherein the EF-1α intron fragment comprises the nucleotide sequence set forth in SEQ ID NO: 2.

Aspect 20. The EF-1α intron fragment according to aspect 5, wherein the EF-1α intron fragment comprises the nucleotide sequence set forth in SEQ ID NO: 3.

Aspect 21. A recombinant expression construct for transgene expression comprising (a) a transgene and (b) a control element operably linked to the transgene and comprising an enhancer, a promoter, and the EF-1α intron fragment according to aspect 1 wherein the transgene is transcribed and translated in a host cell.

Aspect 22. The recombinant expression construct according to aspect 21, wherein the enhancer is a cytomegalovirus (CMV) enhancer.

Aspect 23. The recombinant expression construct according to aspect 22, wherein the cytomegalovirus (CMV) enhancer comprises the nucleotide sequence set forth in SEQ ID NO: 4.

Aspect 24. The recombinant expression construct according to aspect 21, wherein the promoter is selected from the group consisting of a cytomegalovirus (CMV) promoter, an EF-1α promoter, and a β-actin promoter.

Aspect 25. The recombinant expression construct according to aspect 24, wherein the CMV promoter comprises the nucleotide sequence set forth in SEQ ID NO: 5 or 6.

Aspect 26. The recombinant expression construct according to aspect 24, wherein the EF-1α promoter comprises the nucleotide sequence set forth in SEQ ID NO: 7.

Aspect 27. The recombinant expression construct according to aspect 24, wherein the β-actin promoter comprises the nucleotide sequence set forth in SEQ ID NO: 8.

Aspect 28. The recombinant expression construct according to aspect 21, wherein a splicing donor sequence is linked upstream of the EF-1α intron fragment.

Aspect 29. The recombinant expression construct according to aspect 28, wherein the splicing donor sequence comprises the nucleotide sequence set forth in SEQ ID NO: 9 or 10.

Aspect 30. The recombinant expression construct according to aspect 21, wherein the recombinant expression construct comprises an EF-1α exon 2 (E2) sequence.

Aspect 31. The recombinant expression construct according to aspect 30, wherein the EF-1α E2 sequence comprises the nucleotide sequence set forth in SEQ ID NO: 11.

Aspect 32. The recombinant expression construct according to aspect 21, wherein the recombinant expression construct comprises a cytomegalovirus (CMV), EF-1α or β-actin exon 1 (E1) sequence.

Aspect 33. The recombinant expression construct according to aspect 32, wherein the CMV E1 sequence comprises the nucleotide sequence set forth in SEQ ID NO: 12.

Aspect 34. The recombinant expression construct according to aspect 32, wherein the EF-1α E1 sequence comprises the nucleotide sequence set forth in SEQ ID NO: 13.

Aspect 35. The recombinant expression construct according to aspect 32, wherein the β-actin E1 sequence comprises the nucleotide sequence set forth in SEQ ID NO: 14 or 15.

Aspect 36. The recombinant expression construct according to aspect 21, further comprising one or more target sequences for microRNA (miRNA) specific to immune cells.

Aspect 37. The recombinant expression construct according to aspect 36, wherein the miRNA is miR142-3p or miR142-5.

Aspect 38. The recombinant expression construct according to aspect 36, wherein the target sequences for miRNA are selected from the group consisting of antisense oligonucleotides, antagomirs, small hairpin RNA (shRNA) molecules, small interfering RNA (siRNA) molecules, ribozymes, peptide nucleic acids (PNA) oligonucleotides, and locked nucleic acid (LNA) oligonucleotides that have sequences complementary to the full-length or partial sequence of miR142-3p or miR142-5p.

Aspect 39. The recombinant expression construct according to aspect 38, wherein the target sequence for miR142-3p comprises the nucleotide sequence set forth in SEQ ID NO: 16.

Aspect 40. The recombinant expression construct according to aspect 38, wherein the number of the target sequences for miRNA is 2 to 6.

Aspect 41. The recombinant expression construct according to aspect 40, wherein the target sequence for miR142-3p comprises the nucleotide sequence set forth in SEQ ID NO: 17.

Aspect 42. The recombinant expression construct according to aspect 21, further comprising a woodchuck hepatitis virus posttranscriptional regulatory element (WPRE) sequence.

Aspect 43. The recombinant expression construct according to aspect 42, wherein the WPRE sequence comprises the nucleotide sequence set forth in SEQ ID NO: 18.

Aspect 44. The recombinant expression construct according to aspect 21, further comprising one or more polyadenylation (pA) sequences.

Aspect 45. The recombinant expression construct according to aspect 44, wherein the polyadenylation sequences are selected from the group consisting of the nucleotide sequences set forth in SEQ ID NOs: 19 to 22.

Aspect 46. The recombinant expression construct according to aspect 21, wherein the control element comprises 1) the CMV enhancer sequence set forth in SEQ ID NO: 4, 2) the CMV promoter sequence set forth in SEQ ID NO: 5 or 6, the EF-1α promoter sequence set forth in SEQ ID NO: 7 or the chicken β-actin promoter sequence set forth in SEQ ID NO: 8, 3) the CMV E1 sequence set forth in SEQ ID NO: 12, the EF-1α E1 sequence set forth in SEQ ID NO: 13 or the chicken β-actin E1 sequence set forth in SEQ ID NO: 14 or 15, 4) the splicing donor sequence set forth in SEQ ID NO: 9 or 10, 5) the EF-1α intron fragment sequence according to claim 1, and 6) the EF-1α E2 sequence set forth in SEQ ID NO: 11.

Aspect 47. The recombinant expression construct according to aspect 21, wherein the transgene comprises the nucleotide sequence set forth in SEQ ID NO: 23.

Aspect 48. A host cell transduced with the recombinant expression construct according to aspect 21.

Aspect 49. A method for producing a recombinant virus comprising transducing a host cell with the recombinant expression construct according to aspect 21 and a construct containing the rep and cap genes.

Aspect 50. A recombinant virus comprising (a) the capsid protein and (b) the recombinant expression construct according to aspect 21.

Aspect 51. The recombinant virus according to aspect 50, wherein the recombinant virus is an adeno-associated virus (AVV).

Aspect 52. The recombinant virus according to aspect 51, wherein the serotype of the adeno-associated virus is AAV1, AAV2, AAV3, AAV4, AAV5, AAV6, AAV7, AAV8, AAV9 or AAVrh10.

Aspect 53. A pharmaceutical composition comprising the recombinant expression construct according to aspect 21 or the recombinant virus according to aspect 50.

Aspect 54. The pharmaceutical composition according to aspect 53, wherein the composition is used to prevent or treat an ophthalmic disease.

Aspect 55. The pharmaceutical composition according to aspect 54, wherein the ophthalmic disease is selected from the group consisting of diabetic retinopathy, choroidal neovascularization, macular degeneration, retinal degeneration, macular edema, retinal edema, and *Macula tumentia*.

Aspect 56. Use of the recombinant expression construct according to aspect 21 or the recombinant virus according to aspect 50 for therapeutic applications.

Aspect 57. A pharmaceutical composition for preventing or treating an ophthalmic disease, comprising a recombinant or recombinant adeno-associated virus and a pharmaceutically acceptable carrier wherein the recombinant adeno-associated virus comprises (a) an AAV type 8 capsid protein and (b) a recombinant expression construct for transgene expression comprising a transgene comprising the nucleotide sequence set forth in SEQ ID NO: 23 and a control element operably linked to the transgene control and comprising 1) the cytomegalovirus (CMV) enhancer sequence set forth in SEQ ID NO: 4, 2) the chicken β-actin promoter sequence set forth in SEQ ID NO: 8, 3) the chicken β-actin exon 1 (E1) sequence set forth in SEQ ID NO: 15, 4) the splicing donor sequence of the chicken β-actin intron set forth in SEQ ID NO: 10, 5) an EF-1α intron fragment in which contiguous or non-contiguous ones of the nucleotides at positions 1 to 829 in the sequence set forth in SEQ ID NO: 1 are truncated and the nucleotides at positions 830 to 924 in the sequence set forth in SEQ ID NO: 1 are essentially present, and 6) the EF-1α exon 2 (E2) sequence set forth in SEQ ID NO: 11.

BRIEF DESCRIPTION OF THE DRAWINGS

These and/or other aspects and advantages of the present disclosure will become apparent and more readily appreciated from the following description of the aspects, taken in conjunction with the accompanying drawings of which:

In FIG. 2A, ITR-lacking animal cell expression constructs were used. In FIG. 2B, ITR-containing pAAV expression constructs were used. In both FIGS. 2A and 2B, the eGFP expression is shown in the following transduced cell lines (HEK293, HeLa, ARPE-19, RPE-1, Huh-7, and Hep3B).

In FIG. 3A, a combination of a CMV enhancer and CMV promoter were inserted into animal cell expression constructs (i.e., lacking ITR) and used to transduce the cells. In FIG. 3B, In FIG. 3B, the combination of CMV enhancer and CMV promoter were inserted into pAAV expression constructs and used to transduce the cells. In FIG. 3C, the cells were transduced with animal cell expression constructs comprising a combination of a CMV enhancer and a chicken-β actin promoter. In each of FIGS. 3A, 3B, and 3C, the eGFP expression is shown in the following transduced cell lines (HEK293, HeLa, ARPE-19, RPE-1, Huh-7, and Hep3B).

FIG. 4A schematically shows a series of CEE constructs prepared by sequentially truncating an EF-1α intron sequence. Each of the constructs shown included the following: (1) a CMV enhancer (380 base pairs); (2) a promoter comprising a CMV promoter portion (first 31 base pairs from the 5'-end) and EF-1α promoter (201 base pairs); and (3) EF-1α exon 1 (E1) sequence (29 base pairs). The control "CE" construct did not include any additional components, including the EF-1 alpha intron sequence. The other constructs additionally included the following additional components: (4) splice donor sequence, which consisted of the first 19 base pairs from the 5'-end of the full-length EF-1 alpha intron sequence (i.e., SEQ ID NO: 1); (5) EF-1α intron sequence; and (6) EF-1α exon 2 (E2) sequence (nine base pairs). The EF-1α intron sequences included the full-length sequence (924 base pairs) ("CEE-FL") or; (ii) nucleotides 570 to 924 of SEQ ID NO: 1 (355 base pairs) ("CEE-T2"); (iii) nucleotides 721 to 924 of SEQ ID NO: 1 (204 base pairs) ("CEE-T3"); (iv) nucleotides 808 to 924 of SEQ ID NO: 1 (117 base pairs) ("CEE-T3.1"); (v) nucleotides 830 to 924 of SEQ ID NO: 1 (95 base pairs) ("CEE-T3.1.1"); (vi) nucleotides 852 to 924 of SEQ ID NO: 1 (73 base pairs) ("CEE-T3.1.2"); (vii) nucleotides 874 to 924 of SEQ ID NO: 1 (51 base pairs) ("CEE-T3.2"); and (viii) nucleotides 896 to 924 of SEQ ID NO: 1 (29 base pairs) ("CEE-T4"). The total length of each of the constructs are provided to the right. The sequences for the 5' splice site GT rich domain (i.e., CAGGTAAGT; SEQ ID NO: 75) and the consensus BPS poly Y/3' splice site (i.e., GGTTCAAAGTTTTTTTCTTCCATTTCAGG; SEQ ID NO: 76) are shown at the bottom. FIG. 4B shows the effect of the different EF-1α intron sequences (full-length or truncated) on eGFP (i.e., transgene) expression in five different cell lines (HeLa, Hep3B, Huh-7, ARPE-19, and RPE-1). ARPE-19 and RPE-1 cells originated from retina. Huh-7 and Hep3B cells original from liver. HeLa cells originated from cervix. eGFP expression is shown as a percentage of expression observed in cells transduced with the transgene using the CEE-FL construct. "ns"=no significance. ""=p<0.01 and "*"=p<0.001.

FIG. 5A schematically shows a series of CAE constructs including EF-1α intron fragments T3.1.1 and T3.1.2 in combination with the following additional components: (1) CMV enhancer (380 base pairs); (2) a chicken β-actin promoter (279 base pairs); (3) chicken β-actin exon 1 (E1) sequence (32 base pairs); (4) EF-1α exon 1 (E1) sequence (29 base pairs); (5) splice donor sequence, which consisted of the first 19 base pairs from the 5'-end of the full-length EF-1α intron sequence (i.e., SEQ ID NO: 1); and (6) EF-1α exon 2 (E2) sequence (nine base pairs). The control "CA" construct included only the CMV enhancer, chicken β-actin promoter, and the chicken β-actin E1 sequence. The control "CAE-FL" construct included the full-length EF-1α intron sequence. The total length of the constructs are provided to the left. FIG. 5B shows eGFP (i.e., transgene) expression in HeLa (left graph) and ARPE-19 (right graph) cells transduced using the CAE-T3.1.1 and CAE-T3.1.2 constructs. Gene expression is shown as a percentage of expression in corresponding cells transduced using the CA construct (i.e., lacked any EF-1α intron sequence). FIG. 5C schematically shows a series of hybrid intron CA constructs (i.e., CA-T3.1.1 and CA-T3.1.2 constructs) including both EF-1α intron fragment T3.1.1 or T3.1.2 and a chicken β-actin intron fragment. The two constructs additionally included: (1) CMV enhancer; (2) chicken β-actin promoter; (3) chicken β-actin E1 sequence; and (4) EF-1α E2 sequence. The control "CAG-FL" construct included the following: (1) CMV enhancer (380 base pairs); (2) chicken β-actin promoter (279 base pairs); (3) chicken β-actin E1 sequence (93 base pairs); (4) a chimeric intron (comprising intron from chicken β-actin and rabbit β-globin) (924 base pairs); and (5) rabbit β-globin exon 3 (E3) sequence (48 base pairs). The "CA" construct is the same as that described in FIG. 5A. FIG. 5D shows eGFP expression in HeLa (left graph) and Hep3B (right graph) cells transduced using the constructs CA-T3.1.1 and CA-T3.1.2. Gene expression is shown as a percentage of expression in corresponding cells transduced using the CA construct (i.e., lacked any EF-1α intron sequence).

FIG. 6A shows the increasing effects of fragments T3.1.1 and T3.1.2 on gene expression with in vitro gene delivery, FIG. 6B shows the increasing effects of fragments T3.1.1 and T3.1.2 on gene expression with in vivo gene delivery. FIG. 6C is a cleavage map a pAAV-CA-T3.1.1 vector into which aflibercept as a transgene was inserted.

DETAILED DESCRIPTION OF THE DISCLOSURE

Figure 1:
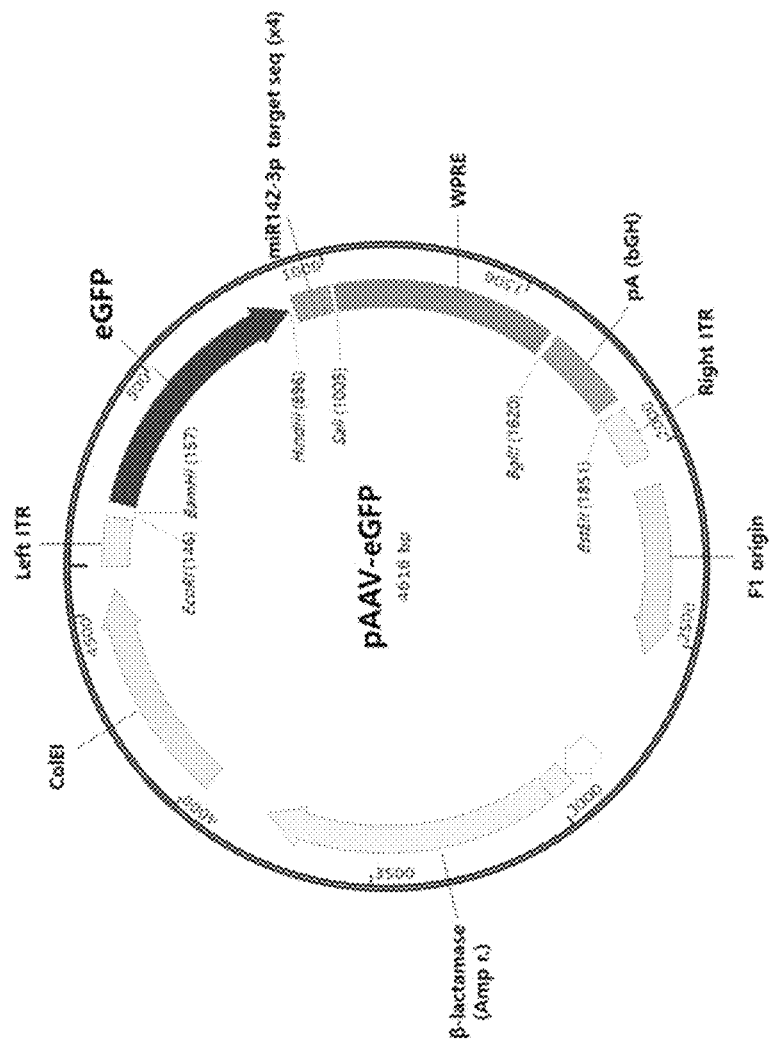
FIG. 1 shows a cleavage map of a pAAV-eGFP expression construct as described herein.

The present disclosure is generally directed to untranslated nucleic acid sequences (also referred to herein as "introns") and the use of such sequences for transgene expression. As described herein, Applicant has identified that certain fragments of the EF-1α intron sequence exhibit superior ability to increase transgene expression. As demonstrated herein, in some aspects, these EF-1α intron fragments are comparable, if not better, than the full-length EF-1α intron in increasing transgene expression. Additional aspects of the present disclosure are provided throughout the present application.

To facilitate an understanding of the disclosure disclosed herein, a number of terms and phrases are defined. Additional definitions are set forth throughout the detailed description.

I. Definitions

Throughout this disclosure, the term "a" or "an" entity refers to one or more of that entity; for example, "a polypeptide," is understood to represent one or more polypeptides. As such, the terms "a" (or "an"), "one or more," and "at least one" can be used interchangeably herein.

Furthermore, "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

The term "at least" prior to a number or series of numbers is understood to include the number adjacent to the term "at least," and all subsequent numbers or integers that could logically be included, as clear from context. For example, the number of nucleotides in a nucleic acid molecule must be an integer. For example, "at least 18 nucleotides of a 21-nucleotide nucleic acid molecule" means that 18, 19, 20, or 21 nucleotides have the indicated property. When at least is present before a series of numbers or a range, it is understood that "at least" can modify each of the numbers in the series or range. "At least" is also not limited to integers (e.g., "at least 5%" includes 5.0%, 5.1%, 5.18% without consideration of the number of significant figures.

It is understood that wherever aspects are described herein with the language "comprising," otherwise analogous aspects described in terms of "consisting of" and/or "consisting essentially of" are also provided.

Unless defined otherwise, all technical and scientific terms used herein have the same meaning as commonly understood by one of ordinary skill in the art to which this disclosure is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary Of Biochemistry And Molecular Biology, Revised, 2000, Oxford University Press, provide one of skill with a general dictionary of many of the terms used in this disclosure.

Units, prefixes, and symbols are denoted in their Système International de Unites (SI) accepted form. Numeric ranges are inclusive of the numbers defining the range. Unless otherwise indicated, amino acid sequences are written left to right in amino to carboxy orientation. The headings provided herein are not limitations of the various aspects of the disclosure, which can be had by reference to the specification as a whole. Accordingly, the terms defined immediately below are more fully defined by reference to the specification in its entirety.

The term "about" is used herein to mean approximately, roughly, around, or in the regions of. When the term "about" is used in conjunction with a numerical range, it modifies that range by extending the boundaries above and below the numerical values set forth. In general, the term "about" can modify a numerical value above and below the stated value by a variance of, e.g., 10 percent, up or down (higher or lower).

As used herein, the term "adeno-associated virus" (AAV), includes but is not limited to, AAV type 1, AAV type 2, AAV type 3 (including types 3A and 3B), AAV type 4, AAV type 5, AAV type 6, AAV type 7, AAV type 8, AAV type 9, AAV type 10, AAV type 11, AAV type 12, AAV type 13, AAVrh.74, snake AAV, avian AAV, bovine AAV, canine AAV, equine AAV, ovine AAV, goat AAV, shrimp AAV, those AAV serotypes and clades disclosed by Gao et al. (*J. Virol.* 78:6381 (2004)) and Moris et al. (*Virol.* 33:375 (2004)), and any other AAV now known or later discovered. See, e.g., FIELDS et al. VIROLOGY, volume 2, chapter 69 (4th ed., Lippincott-Raven Publishers). In some aspects, an "AAV" includes a derivative of a known AAV. In some aspects, an "AAV" includes a modified or an artificial AAV.

The terms "administration," "administering," and grammatical variants thereof refer to introducing a composition (e.g., polynucleotide comprising a transgene and untranslated nucleic acid sequence described herein) into a subject via a pharmaceutically acceptable route. The introduction of a composition into a subject is by any suitable route, including intratumorally, orally, pulmonarily, intranasally, parenterally (intravenously, intra-arterially, intramuscularly, intraperitoneally, or subcutaneously), rectally, intralymphatically, intrathecally, periocularly or topically. Administration includes self-administration and the administration by another. A suitable route of administration allows the composition or the agent to perform its intended function. For example, if a suitable route is intravenous, the composition is administered by introducing the composition or agent into a vein of the subject.

As used herein, a "CEE" construct comprises a CMV enhancer, an EF-1α promoter, and an EF-1α intron fragment. A "CE" construct comprises a CMV enhancer and an EF-1α promoter, but does not contain any intron fragment (e.g., no EF-1α intron fragment). A "CAE" construct comprises a CMV enhancer, a chicken β-actin promoter, and an EF-1α intron fragment. As used herein, a "CAG" construct comprises a CMV enhancer, a chicken β-actin promoter, and a chicken β-actin/rabbit β-globin hybrid intron fragment. A "CA" construct comprises a CMV enhancer and a chicken β-actin promoter, but does not contain any intron fragment (e.g., no EF-1α intron fragment). See FIGS. 4A, 5A, and 5C.

As used herein, the term "conserved" refers to nucleotides or amino acid residues of a polynucleotide sequence or polypeptide sequence, respectively, that are those that occur unaltered in the same position of two or more sequences being compared. Nucleotides or amino acids that are relatively conserved are those that are conserved amongst more related sequences than nucleotides or amino acids appearing elsewhere in the sequences.

In some aspects, two or more sequences are said to be "completely conserved" or "identical" if they are 100% identical to one another. In some aspects, two or more sequences are said to be "highly conserved" if they are at least 70% identical, at least 80% identical, at least 90% identical, or at least 95% identical to one another. In some aspects, two or more sequences are said to be "highly conserved" if they are about 70% identical, about 80% identical, about 90% identical, about 95%, about 98%, or about 99% identical to one another. In some aspects, two or more sequences are said to be "conserved" if they are at least 30% identical, at least 40% identical, at least 50% identical, at least 60% identical, at least 70% identical, at least 80% identical, at least 90% identical, or at least 95% identical to one another. In some aspects, two or more sequences are said to be "conserved" if they are about 30% identical, about 40% identical, about 50% identical, about 60% identical, about 70% identical, about 80% identical, about 90% identical, about 95% identical, about 98% identical, or about 99% identical to one another. Conservation of sequence can apply to the entire length of a polynucleotide or polypeptide or can apply to a portion, region or feature thereof.

The terms "complementary" and "complementarity" refer to two or more oligomers (i.e., each comprising a nucleobase sequence), or between an oligomer and a target gene, that are related with one another by Watson-Crick base-pairing rules. For example, the nucleobase sequence "T-G-A (5'→3')," is complementary to the nucleobase sequence "A-C-T (3'→5')." Complementarity can be "partial," in which less than all of the nucleobases of a given nucleobase sequence are matched to the other nucleobase sequence according to base pairing rules. For example, in some aspects, complementarity between a given nucleobase sequence and the other nucleobase sequence can be about 70%, about 75%, about 80%, about 85%, about 90%, or about 95%. Accordingly, in certain aspects, the term "complementary" refers to at least about 80%, at least about 85%, at least about 90%, at least about 91%, at least about 92%, at least about 93%, at least about 94%, at least about 95%, at least about 96%, at least about 97%, at least about 98%, or at least about 99% match or complementarity to a target nucleic acid sequence. Or, there can be "complete" or "perfect" (100%) complementarity between a given nucleobase sequence and the other nucleobase sequence to continue the example. In some aspects, the degree of complementarity between nucleobase sequences has significant effects on the efficiency and strength of hybridization between the sequences.

As used herein, the expression "contiguous or non-contiguous nucleotides are truncated" is meant to include contiguous or non-contiguous nucleotide sequences remaining as a result of the truncation compared to the wild type (or original) sequence, but not to include any process of truncation. The term can include "truncation of contiguous nucleotides", "truncation of non-contiguous nucleotides remaining untruncated between truncated nucleotides", and "insertion of different types of nucleotides into positions of truncated contiguous or non-contiguous nucleotides". For example, in the case of the nucleotide sequence "A-T-G-C-C-G-T-C", the truncation of contiguous nucleotides includes truncation of one or more contiguous nucleotides, such as "A-_-_-_-C-G-T-C", the truncation of non-contiguous nucleotides means that one or more nucleotides remain untruncated between truncated nucleotides, such as "A-_-G-_-C-G-T-_", and the insertion of different types of nucleotides into positions of truncated contiguous or non-contiguous nucleotides means that one or more nucleotides different from the original ones are inserted at the positions of truncated nucleotides, such as "A-A-G-_-C-G-T-G".

The term "downstream" refers to a nucleotide sequence that is located 3' to a reference nucleotide sequence. In certain aspects, downstream nucleotide sequences relate to sequences that follow the starting point of transcription. For example, the translation initiation codon of a gene is located downstream of the start site of transcription.

As used herein, the term "enhancer" refers to a segment of DNA which contains sequences capable of providing enhanced transcription and in some instances can function independent of their orientation relative to another control sequence. An enhancer can function cooperatively or additively with promoters and/or other enhancer elements.

The terms "excipient" and "carrier" are used interchangeably and refer to an inert substance added to a pharmaceutical composition to further facilitate administration of a compound, e.g., a polynucleotide comprising a transgene and an untranslated nucleic acid sequence described herein.

The term "exon" refers to a defined section of nucleic acid that encodes for a protein, or a nucleic acid sequence that is represented in the mature form of an RNA molecule after either portions of a pre-processed (or precursor) RNA have been removed by splicing. The mature RNA molecule can be a messenger RNA (mRNA) or a functional form of a non-coding RNA, such as rRNA or tRNA.

The term "expression," as used herein, refers to a process by which a polynucleotide produces a gene product, e.g., RNA or a polypeptide. It includes, without limitation, transcription of the polynucleotide into messenger RNA (mRNA), and the translation of mRNA into a polypeptide. Expression produces a "gene product." As used herein, a gene product can be, e.g., a nucleic acid, such as an RNA produced by transcription of a gene. As used herein, a gene product can be either a nucleic acid or a polypeptide which is translated from a transcript. Gene products described herein further include nucleic acids with post transcriptional modifications, e.g., polyadenylation or splicing, or polypeptides with post translational modifications, e.g., phosphorylation, methylation, glycosylation, the addition of lipids, association with other protein subunits, or proteolytic cleavage.

As used herein, the term "identity" refers to the overall monomer conservation between polymeric molecules, e.g., between polynucleotide molecules. The term "identical" without any additional qualifiers, e.g., polynucleotide A is identical to polynucleotide B, implies the polynucleotide sequences are 100% identical (100% sequence identity). Describing two sequences as, e.g., "70% identical," is equivalent to describing them as having, e.g., "70% sequence identity."

Calculation of the percent identity of two polypeptide or polynucleotide sequences, for example, can be performed by aligning the two sequences for optimal comparison purposes (e.g., gaps can be introduced in one or both of a first and a second polypeptide or polynucleotide sequences for optimal alignment and non-identical sequences can be disregarded for comparison purposes). In certain aspects, the length of a sequence aligned for comparison purposes is at least 30%, at least 40%, at least 50%, at least 60%, at least 70%, at least 80%, at least 90%, at least 95%, or 100% of the length of the reference sequence. The amino acids at corresponding amino acid positions, or bases in the case of polynucleotides, are then compared.

When a position in the first sequence is occupied by the same amino acid or nucleotide as the corresponding position in the second sequence, then the molecules are identical at that position. The percent identity between the two sequences is a function of the number of identical positions shared by the sequences, taking into account the number of gaps, and the length of each gap, which needs to be introduced for optimal alignment of the two sequences. The comparison of sequences and determination of percent identity between two sequences can be accomplished using a mathematical algorithm.

Suitable software programs that can be used to align different sequences (e.g., polynucleotide sequences) are available from various sources. One suitable program to determine percent sequence identity is bl2seq, part of the BLAST suite of program available from the U.S. government's National Center for Biotechnology Information BLAST web site (blast.ncbi.nlm.nih.gov). Bl2seq performs a comparison between two sequences using either the BLASTN or BLASTP algorithm. BLASTN is used to compare nucleic acid sequences, while BLASTP is used to compare amino acid sequences. Other suitable programs are, e.g., Needle, Stretcher, Water, or Matcher, part of the EMBOSS suite of bioinformatics programs and also available from the European Bioinformatics Institute (EBI) at www.ebi.ac.uk/Tools/psa.

Sequence alignments can be conducted using methods known in the art such as MAFFT, Clustal (ClustalW, Clustal X or Clustal Omega), MUSCLE, etc.

Different regions within a single polynucleotide or polypeptide target sequence that aligns with a polynucleotide or polypeptide reference sequence can each have their own percent sequence identity. It is noted that the percent sequence identity value is rounded to the nearest tenth. For example, 80.11, 80.12, 80.13, and 80.14 are rounded down to 80.1, while 80.15, 80.16, 80.17, 80.18, and 80.19 are rounded up to 80.2. It also is noted that the length value will always be an integer.

In certain aspects, the percentage identity (% ID) or of a first amino acid sequence (or nucleic acid sequence) to a second amino acid sequence (or nucleic acid sequence) is calculated as % ID=100×(Y/Z), where Y is the number of amino acid residues (or nucleobases) scored as identical matches in the alignment of the first and second sequences (as aligned by visual inspection or a particular sequence alignment program) and Z is the total number of residues in the second sequence. If the length of a first sequence is longer than the second sequence, the percent identity of the first sequence to the second sequence will be higher than the percent identity of the second sequence to the first sequence.

One skilled in the art will appreciate that the generation of a sequence alignment for the calculation of a percent sequence identity is not limited to binary sequence-sequence comparisons exclusively driven by primary sequence data. It will also be appreciated that sequence alignments can be generated by integrating sequence data with data from heterogeneous sources such as structural data (e.g., crystallographic protein structures), functional data (e.g., location of mutations), or phylogenetic data. A suitable program that integrates heterogeneous data to generate a multiple sequence alignment is T-Coffee, available at www.tcoffee.org, and alternatively available, e.g., from the EBI. It will also be appreciated that the final alignment used to calculate percent sequence identity can be curated either automatically or manually.

As used herein, the term "intron" refers to section of DNA (intervening sequences) within a gene that do not encode part of the protein that the gene produces, and that is spliced out of the mRNA that is transcribed from the gene before it is exported from the cell nucleus. "Intron sequence" refers to the nucleic acid sequence of the intron. Such sequences are also referred to herein as "untranslated nucleic acid sequence." Thus, introns are those regions of DNA sequences that are transcribed along with the coding sequence (exons) but are removed during the formation of mature mRNA.

As used herein, the term "intron fragment" refers to a fragment derived from a full-length EF-1α intron A sequence (i.e., the first intron of EF-1α, such as that set forth in SEQ ID NO: 1). The fragment is meant to exclude full-length EF-1α intron. In some aspects, the "intron fragment" includes a minimum number of nucleotides or elements required to achieve an expression level exceeding that achieved by a corresponding construct in which all nucleotides of EF-1α intron A are lacking. Accordingly, an intron fragment of the present disclosure (also referred to herein as "untranslated nucleic acid sequence") is not particularly limited as long as it comprises a fragment of EF-1α intron and can increase the expression of a transgene. As demonstrated herein, in some aspects, an intron fragment (i.e., untranslated nucleic acid sequence) can increase the transcription of a transgene, resulting in enhanced expression of the transgene. Accordingly, in some aspects, an intron fragment described herein can be an untranslated regulatory element.

As used herein, the terms "isolated," "purified," "extracted," and grammatical variants thereof are used interchangeably and refer to the state of a preparation of desired composition of the present disclosure, e.g., a polynucleotide comprising a transgene and an untranslated nucleic acid sequence, that has undergone one or more processes of purification. In some aspects, isolating or purifying as used herein is the process of removing, partially removing (e.g., a fraction) a composition of the present disclosure, e.g., a polynucleotide described herein from a sample containing contaminants.

In some aspects, an isolated composition has no detectable undesired activity or, alternatively, the level or amount of the undesired activity is at or below an acceptable level or amount. In other aspects, an isolated composition has an amount and/or concentration of desired composition of the present disclosure, at or above an acceptable amount and/or concentration and/or activity. In other aspects, the isolated composition is enriched as compared to the starting material from which the composition is obtained. This enrichment can be by at least about 10%, at least about 20%, at least about 30%, at least about 40%, at least about 50%, at least about 60%, at least about 70%, at least about 80%, at least about 90%, at least about 95%, at least about 96%, at least about 97%, at least about 98%, at least about 99%, at least about 99.9%, at least about 99.99%, at least about 99.999%, at least about 99.9999%, or greater than 99.9999% as compared to the starting material.

In some aspects, isolated preparations are substantially free of residual biological products. In some aspects, the isolated preparations are 100% free, at least about 99% free, at least about 98% free, at least about 97% free, at least about 96% free, at least about 95% free, at least about 94% free, at least about 93% free, at least about 92% free, at least about 91% free, or at least about 90% free of any contaminating biological matter. Residual biological products can include abiotic materials (including chemicals) or unwanted nucleic acids, proteins, lipids, or metabolites.

The term "linked," as used herein, refers to a first amino acid sequence or polynucleotide sequence covalently or non-covalently joined to a second amino acid sequence or polynucleotide sequence, respectively. The first amino acid or polynucleotide sequence can be directly joined or juxtaposed to the second amino acid or polynucleotide sequence or alternatively an intervening sequence can covalently join the first sequence to the second sequence. The term "linked" means not only a fusion of a first polynucleotide sequence to a second polynucleotide sequence at the 5'-end or the 3'-end, but also includes insertion of the whole first polynucleotide sequence (or the second polynucleotide sequence) into any two nucleotides in the second polynucleotide sequence (or the first polynucleotide sequence, respectively). The first polynucleotide sequence can be linked to a second polynucleotide sequence by a phosphodiester bond or a linker. The linker can be, e.g., a polynucleotide.

As used herein, the term "macular degeneration" refers to any number of disorders and conditions in which the *Macula* degenerates or loses functional activity. The degeneration or loss of functional activity can arise as a result of, for example, cell death, decreased cell proliferation, loss of normal biological function, or a combination of the foregoing. Macular degeneration can lead to and/or manifest as alterations in the structural integrity of the cells and/or extracellular matrix of the *Macula*, alteration in normal cellular and/or extracellular matrix architecture, and/or the loss of function of macular cells. The cells can be any cell type normally present in or near the *Macula* including RPE cells, photoreceptors, and/or capillary endothelial cells. Age-related macular degeneration is the most common of the macular degeneration, but the term "macular degeneration" does not necessarily exclude macular degeneration in patients who are not the elderly. Non-limiting examples of macular degenerations include: age-related macular degeneration (wet or dry); Best macular dystrophy, Sorsby fundus dystrophy, Mallatia Leventinese, Doyne honeycomb retinal dystrophy, Stargardt disease (also called Stargardt macular dystrophy, juvenile macular degeneration, or fundus flavimaculatus), and pigment epithelial detachment associated macular degeneration.

As used herein, the term "age-related macular degeneration" (AMD) refers to a retinopathy which usually affects older individuals and is associated with a loss of central vision, resulting from damage to the central part (i.e., *Macula*) of the retina. AMD is generally characterized by a progressive accumulation or aggregation of yellowish insoluble extracellular deposits, called drusen (buildup of extracellular proteins, such as amyloid beta, and lipids), in the *Macula* (primarily between the retinal pigment epithelium (RPE) and the underlying choroid). The accumulation or aggregation of these deposits within the *Macula* can cause gradual deterioration of the *Macula*, resulting in central vision impairment. As used herein, the term "*Macula*," refers to the central part of the retina that is responsible for central, high-resolution, color vision.

The pathogenesis of age-related macular degeneration is not well known, although some theories have been put forward, including oxidative stress, mitochondrial dysfunction, and inflammatory processes. The imbalance between the production of damaged cellular components and degradation leads to the accumulation of harmful products, for example, intracellular lipofuscin and extracellular drusen. Incipient atrophy is demarcated by areas of retinal pigment epithelium (RPE) thinning or depigmentation that precede geographic atrophy in the early stages of AMD. In advanced stages of AMD, atrophy of the RPE (geographic atrophy) and/or development of new blood vessels (neovascularization) result in the death of photoreceptors and central vision loss. In the dry (nonexudative) AMD, cellular debris called drusen accumulates between the retina and the choroid, causing atrophy and scarring to the retina. In the wet (exudative) AMD, which is more severe, blood vessels grow up from the choroid (neovascularization) behind the retina which can leak exudate and fluid and also cause hemorrhaging.

Depending on the extent of the drusen present, AMD can be categorized into three primary stages: (i) early, (ii) intermediate, and (iii) advanced or late. The early stage AMD is characterized by the presence of either several small (e.g., less than about 63 microns in diameter) drusen or a few medium-sized (e.g., between about 63 to 124 microns in diameter) drusen. During the early stage, patients have no apparent symptoms with no vision loss. The intermediate stage is characterized by the presence of many medium-sized drusen or one or more large (e.g., more than about 125 microns in diameter) drusen. During this stage, some patients can begin to experience blurred spots in the center of their vision. The advanced or late stage AMD is characterized by large areas of damage to the retinal tissue, causing central blind spots and the eventual loss of central vision. Based on the type of damage (e.g., presence or absence of neovascularization), advanced or late stage AMD can be further divided into two subtypes: (i) geographic atrophy (also called atrophic AMD) and (ii) wet AMD (also called neovascular or exudative AMD).

There are two primary forms of AMD: (i) dry AMD and (ii) wet AMD. Unless specified otherwise, the term "age-related macular degeneration" comprises both dry AMD and wet AMD. As used herein, the term "age-related macular degeneration" also comprises all types of age-related macular degeneration regardless of the cause and any and all symptoms of age-related macular degeneration. Non-limiting examples of symptoms associated with macular degeneration (e.g., age-related macular degeneration) include: loss of central vision, distortion, decreased contrast sensitivity, blurred vision, difficulty adapting to low light level, sudden onset and rapid worsening of symptoms, and decreased color vision. In some aspects, macular degeneration (e.g., age-related macular degeneration) can cause macular edema (i.e., swelling of the *Macula* resulting from collection of fluid and protein deposits on or under the *Macula*).

As used herein, the term "dry AMD" (also referred to as atrophic age-related macular degeneration or non-exudative AMD) refers to all forms of AMD that are not wet (neovascular) AMD. This includes early and intermediate forms of AMD, as well as the advanced form of dry AMD known as geographic atrophy. Dry AMD patients tend to have minimal symptoms in the earlier stages; visual function loss occurs more often if the condition advances to geographic atrophy.

As used herein, the term "wet AMD" (also referred to as neovascular age-related macular degeneration or exudative AMD) refers to retinal condition characterized by the presence of retinal neovascularization and is the most advanced form of AMD. In wet AMD, blood vessels grow from the choriocapillaris through defects in Bruch's membrane, and in some cases the underlying retinal pigment epithelium (choroidal neovascularization or angiogenesis). Organization of serous or hemorrhagic exudates escaping from these vessels can result in fibrovascular scarring of the macular region with attendant degeneration of the neuroretina, detachment and tears of the retinal pigment epithelium, vitreous hemorrhage, and permanent loss of central vision.

The terms "miRNA," "miR," and "microRNA" are used interchangeably and refer to a microRNA molecule found in eukaryotes that is involved in RNA-based gene regulation. The term will be used to refer to the single-stranded RNA molecule processed from a precursor. In some aspects, the term "antisense oligomers" can also be used to describe the microRNA molecules of the present disclosure. Names of miRNAs and their sequences related to the present disclosure are provided herein. MicroRNAs recognize and bind to target mRNAs through imperfect base pairing leading to destabilization or translational inhibition of the target mRNA and thereby downregulate target gene expression. Conversely, targeting miRNAs via molecules comprising a miRNA binding site (generally a molecule comprising a sequence complementary to the seed region of the miRNA) can reduce or inhibit the miRNA-induced translational inhibition leading to an upregulation of the target gene.

"Nucleic acid," "nucleic acid molecule," "nucleotide sequence," "polynucleotide," and grammatical variants thereof are used interchangeably and refer to a sequence of nucleotides connected by phosphodiester linkages. Polynucleotides are presented herein in the direction from the 5' to the 3' direction. A polynucleotide of the present disclosure can be a deoxyribonucleic acid (DNA) molecule or ribonucleic acid (RNA) molecule. Nucleotide bases are indicated herein by a single letter code: adenine (A), guanine (G), thymine (T), cytosine (C), inosine (I) and uracil (U).

As used herein, the term "operatively linked" or "operably linked" means that DNA sequences to be linked are located adjacent to each other to perform a desired function. For instance, a promoter is operatively linked to a coding region if the promoter helps initiate transcription of the coding sequence (e.g., transgene). As long as this functional relationship is maintained, the promoter needs not be contiguous with the coding region.

The terms "pharmaceutically acceptable carrier," "pharmaceutically acceptable excipient," and grammatical variations thereof, encompass any of the agents approved by a regulatory agency of the U.S. Federal government or listed in the U.S. Pharmacopeia for use in animals, including humans, as well as any carrier or diluent that does not cause the production of undesirable physiological effects to a degree that prohibits administration of the composition to a subject and does not abrogate the biological activity and properties of the administered compound. Included are excipients and carriers that are useful in preparing a pharmaceutical composition and are generally safe, non-toxic, and desirable.

As used herein, the term "pharmaceutical composition" refers to one or more of the compositions described herein (e.g., polynucleotides, vectors, cells, and/or recombinant viruses) mixed or intermingled with, or suspended in one or more other chemical components, such as pharmaceutically acceptable carriers and excipients.

As used herein, the terms "promoter" and "promoter sequence" are interchangeable and refer to a DNA sequence capable of controlling the expression of a coding sequence or functional RNA. In general, a coding sequence is located 3' to a promoter sequence. Promoters can be derived in their entirety from a native gene, or be composed of different elements derived from different promoters found in nature, or even comprise synthetic DNA segments. It is understood by those skilled in the art that different promoters can direct the expression of a gene in different tissues or cell types, or at different stages of development, or in response to different environmental or physiological conditions. Promoters that cause a gene to be expressed in most cell types at most times are commonly referred to as "constitutive promoters." Promoters that cause a gene to be expressed in a specific cell type are commonly referred to as "cell-specific promoters" or "tissue-specific promoters." Promoters that cause a gene to be expressed at a specific stage of development or cell differentiation are commonly referred to as "developmentally-specific promoters" or "cell differentiation-specific promoters." Promoters that are induced and cause a gene to be expressed following exposure or treatment of the cell with an agent, biological molecule, chemical, ligand, light, or the like that induces the promoter are commonly referred to as "inducible promoters" or "regulatable promoters." It is further recognized that since in most cases the exact boundaries of regulatory sequences have not been completely defined, DNA fragments of different lengths can have identical promoter activity.

The promoter sequence is typically bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease S1), as well as protein binding domains (consensus sequences) responsible for the binding of RNA polymerase. In some aspects, a promoter that can be used with the present disclosure includes a tissue specific promoter.

As used herein, the term "gene regulatory region" or "regulatory region" refers to nucleotide sequences located upstream (5' non-coding sequences), within, or downstream (3' non-coding sequences) of a coding region, and which influence the transcription, RNA processing, stability, or translation of the associated coding region. Regulatory regions can include promoters, translation leader sequences, introns, polyadenylation recognition sequences, RNA processing sites, effector binding sites, or stem-loop structures. If a coding region is intended for expression in a eukaryotic cell, a polyadenylation signal and transcription termination sequence will usually be located 3' to the coding sequence.

In some aspects, a polynucleotide described herein (e.g., comprising a transgene and an untranslated nucleic acid sequence) can include a promoter and/or other expression (e.g., transcription) control elements operably associated with one or more coding regions. In an operable association a coding region for a gene product is associated with one or more regulatory regions in such a way as to place expression of the gene product under the influence or control of the regulatory region(s). For example, a coding region and a promoter are "operably associated" if induction of promoter function results in the transcription of mRNA encoding the gene product encoded by the coding region, and if the nature of the linkage between the promoter and the coding region does not interfere with the ability of the promoter to direct the expression of the gene product or interfere with the ability of the DNA template to be transcribed. Other expression control elements, besides a promoter, for example enhancers, operators, repressors, and transcription termination signals, can also be operably associated with a coding region to direct gene product expression.

As used herein, the term "subject," "patient," "individual," and "host," and variants thereof, are interchangeable and refer to any mammalian subject to which any of the compositions described herein (e.g., polynucleotides, the recombinant expression constructs, cells, pharmaceutical compositions, or recombinant viruses) are administered. Non-limiting examples include humans, domestic animals (e.g., dogs, cats and the like), farm animals (e.g., cows, sheep, pigs, horses and the like), and laboratory animals (e.g., monkey, rats, mice, rabbits, guinea pigs and the like) for whom diagnosis, treatment, or therapy is desired, particularly humans. The methods described herein are applicable to both human therapy and veterinary applications.

As used herein, the phrase "subject in need thereof" includes subjects, such as mammalian subjects, that would benefit from administration of composition described herein.

As used herein, the term "therapeutically effective amount" is the amount of reagent or pharmaceutical compound comprising a composition of the present disclosure (e.g., polynucleotide comprising a transgene and an untranslated nucleic acid sequence) that is sufficient to a produce a desired therapeutic effect, pharmacologic and/or physiologic effect on a subject in need thereof. A therapeutically effective amount can be a "prophylactically effective amount" as prophylaxis can be considered therapy.

As used herein, the term "transgene" refers to at least one polynucleotide or polynucleotide region encoded in a recombinant expression construct or an expression product of the polynucleotide or polynucleotide region, a polynucleotide encoding a polypeptide or multi-polypeptide or a modulatory or regulatory nucleic acid. In some aspects, the transgene can be heterologous to the cell (i.e., not naturally expressed in the cell) in which it is inserted (or transduced).

The terms "treat," "treatment," or "treating," as used herein refers to, e.g., the reduction in severity of a disease or condition; the reduction in the duration of a disease course; the amelioration or elimination of one or more symptoms associated with a disease or condition; the provision of beneficial effects to a subject with a disease or condition, without necessarily curing the disease or condition. The term also includes prophylaxis or prevention of a disease or condition or its symptoms thereof.

The term "upstream" refers to a nucleotide sequence that is located 5' to a reference nucleotide sequence.

As used herein, the term "vector" or "construct" refers to any vehicle into which a nucleic acid or a gene can be inserted, such as delivery vehicles into which a nucleic acid sequence can be inserted for introduction into a cell where it can be replicated. The nucleic acid sequence which can be inserted into a vector can be exogenous or heterologous. The nucleic acid sequence can be a transgene. Examples of constructs include, but are not limited to, plasmids, cosmids, and viruses (e.g., AAVs). Those skilled in the art can construct the vector or construct through standard recombinant techniques (Maniatis, et al., *Molecular Cloning*, A Laboratory Manual, Cold Spring Harbor Press, Cold Spring Harbor, N. Y., 1988; and Ausubel et al., In: *Current Protocols in Molecular Biology*, John, Wiley & Sons, Inc, NY, 1994, etc.). As used herein, the term "expression vector" or "expression construct" refers to a vector or construct including a nucleotide sequence coding for at least a portion of a gene product to be transcribed. In some cases, RNA molecules are then translated into a protein, polypeptide or peptide. Expression constructs can include various control elements. In addition to regulatory sequences that govern transcription and translation, vectors and expression vectors can include nucleotide sequence that serve other functions as well.

Vectors can be engineered to encode selectable markers or reporters that provide for the selection or identification of cells that have incorporated the vector. Expression of selectable markers or reporters allows identification and/or selection of host cells that incorporate and express other coding regions contained on the vector. Examples of selectable marker genes known and used in the art include: genes providing resistance to ampicillin, streptomycin, gentamycin, kanamycin, hygromycin, bialaphos herbicide, sulfonamide, and the like; and genes that are used as phenotypic markers, i.e., anthocyanin regulatory genes, isopentenyl transferase gene, and the like. Examples of reporters known and used in the art include: luciferase (Luc), green fluorescent protein (GFP), chloramphenicol acetyltransferase (CAT), β-galactosidase (LacZ), β-glucuronidase (Gus), and the like. Selectable markers can also be considered to be reporters.

II. Polynucleotides

II.A. Untranslated Nucleic Acid Sequences

The present disclosure is directed to polynucleotides comprising an untranslated nucleic acid sequence, wherein the untranslated nucleic acid sequence is capable of increasing the expression of a transgene when translated. Specifically, provided herein are elongation factor-1 alpha (EF-1α) intron sequences that are shorter than the full-length EF-1α intron.

Elongation Factor 1 Alpha (EF-1α) is a gene located on chromosome 6 (nucleotides 73,489,308-73,525,587 of GenBank Accession Number NC 000006.12; minus strand orientation). The EF-1α gene includes 8 exons and 7 introns, and encodes the eukaryotic elongation factor 1A (also known as eEF1A1 and eEF1A) protein which plays an important role in mRNA translation (e.g., carries aminoacyl-tRNA to the A site of the ribosome as a ternary complex eEF1A1-GTP-aa-tRNA). Scaggiante et al., *Atlas Genet Cytogenet Oncol Haematol* 19(4): 256-265 (March 2015). The nucleotide sequence of the full-length EF-1α intron is set forth in SEQ ID NO: 1 (924 nucleotides long). As described herein, the untranslated nucleic acid sequences of the present disclosure (i.e., EF-1α intron fragment sequences) provide distinct advantages over the full-length EF-1α intron (or any other intron known in the art). For instance, in some aspects, the untranslated nucleic acid sequences described herein can increase the expression of a transgene to a greater extent than the full-length EF-1α intron. Also, because the untranslated nucleic acid sequences of the present disclosure are shorter than the full-length counterpart, in some aspects, they can be used in combination with larger transgenes. For instance, an AAV capsid (such as those described herein) can accommodate a maximum of about 4.7 kb of nucleic acid. Accordingly, in some aspects, with the EF-1α intron fragments described herein (i.e., untranslated nucleic acid sequences), it is possible to incorporate larger transgenes and/or additional cis-elements for much enhanced gene expression.

In some aspects, an untranslated nucleic acid sequence described herein (i.e., the EF-1α intron fragment) comprises nucleotides at positions 874 to 924 of the sequence set forth in SEQ ID NO: 1, but does not comprise SEQ ID NO: 1. In some aspects, an untranslated nucleic acid sequence consists essentially of nucleotides 874-924 of SEQ ID NO: 1. In some aspects, an untranslated nucleic acid sequence consists of nucleotides 874-924 of SEQ ID NO: 1. Such an EF-1α intron fragment is also referred to herein as "T3.2 fragment" and set forth in SEQ ID NO: 57. In some aspects, the untranslated nucleic acid sequence has at least about 70%, at least about 80%, at least about 85%, at least about 90%, at least about 95%, at least about 96%, at least about 97%, at least about 98%, at least about 99%, or about 100% sequence identity to nucleotides 874 to 924 of SEQ ID NO: 1, wherein the untranslated nucleic acid sequence does not comprise SEQ ID NO: 1.

In some aspects, an untranslated nucleic acid sequence described herein (i.e., the EF-1α intron fragment) comprises nucleotides 852-924 of SEQ ID NO: 1, but does not comprise SEQ ID NO: 1. In some aspects, an untranslated nucleic acid sequence of the present disclosure consists essentially of nucleotides 852-924 of SEQ ID NO: 1. In some aspects, an untranslated nucleic acid sequence consists of nucleotides 852-924 of SEQ ID NO: 1. Such an EF-1α intron fragment is also referred to herein as "T3.1.2 fragment" and set forth in SEQ ID NO: 3. In some aspects, the untranslated nucleic acid sequence has at least about 70%, at least about 80%, at least about 85%, at least about 90%, at least about 95%, at least about 96%, at least about 97%, at least about 98%, at least about 99%, or about 100% sequence identity to nucleotides 852-924 of SEQ ID NO: 1, wherein the untranslated nucleic acid sequence does not comprise SEQ ID NO: 1.

In some aspects, an untranslated nucleic acid sequence described herein (i.e., the EF-1α intron fragment) comprises nucleotides 830-924 of SEQ ID NO: 1, but does not comprise SEQ ID NO: 1. In some aspects, an untranslated nucleic acid sequence of the present disclosure consists essentially of nucleotides 830-924 of SEQ ID NO: 1. In some aspects, an untranslated nucleic acid sequence consists of nucleotides 830-924 of SEQ ID NO: 1. Such an EF-1α intron fragment is also referred to herein as "T3.1.1 fragment" and set forth in SEQ ID NO: 2. In some aspects, the untranslated nucleic acid sequence has at least about 70%, at least about 80%, at least about 85%, at least about 90%, at least about 95%, at least about 96%, at least about 97%, at least about 98%, at least about 99%, or about 100% sequence identity to nucleotides 830-924 of SEQ ID NO: 1, wherein the untranslated nucleic acid sequence does not comprise SEQ ID NO: 1.

As is apparent from the present disclosure, in addition to the above described nucleotides (i.e., positions 874-924, 852-924, and 830-924 of SEQ ID NO: 1—i.e., SEQ ID NO: 57, SEQ ID NO: 3, and SEQ ID NO: 2, respectively), in some aspects, an untranslated nucleic acid sequence of the present disclosure can comprise additional contiguous or non-contiguous nucleotides of the EF-1α intron sequence at the 5' region, such as that set forth in SEQ ID NO: 1. For instance, in some aspects, the additional contiguous or non-contiguous nucleotides at the 5' region can be added anywhere upstream of nucleotides 874 to 924, 852-924, or 830-924 of SEQ ID NO: 1. In some aspects, the additional contiguous or non-contiguous nucleotides at the 5' region are derived from the full-length EF-1α intron sequence, i.e., SEQ ID NO: 1. In some aspects, the additional contiguous or non-contiguous nucleotides at the 5' region and/or 3' region are derived from any sequences heterologous to the full-length EF-1α intron sequence, i.e., SEQ ID NO: 1.

Accordingly, in some aspects, un untranslated nucleic acid sequence described herein does not comprise any additional contiguous or non-contiguous nucleotides derived from nucleotide positions 1 to 873 in the sequence set forth in SEQ ID NO: 1 (resulting in an EF-1α intron fragment comprising, consisting essentially of, or consisting of nucleotides 874-924 of SEQ ID NO: 1; "T3.2 fragment"; SEQ ID NO: 57).

In some aspects, an untranslated nucleic acid sequence described herein does not comprise any contiguous or non-contiguous nucleotides derived from nucleotides at positions 1 to 870 in the sequence set forth in SEQ ID NO: 1 (resulting in an EF-1α intron fragment comprising, consisting essentially of, or consisting of nucleotides 871 to 924 of SEQ ID NO: 1; i.e., SEQ ID NO: 58). In some aspects, such an untranslated nucleic acid sequence can comprise one or more contiguous or non-contiguous nucleotides derived from within nucleotide positions 1 to 870 of SEQ ID NO: 1 with the proviso that the one or more contiguous or non-contiguous nucleotides is not the entire length of nucleotide positions 1 to 870 of SEQ ID NO: 1 (e.g., shorter than nucleotides 1 to 870 of SEQ ID NO: 1). In some aspects, such an untranslated nucleic acid sequence can comprise one or more different types of nucleotides (i.e., not derived from nucleotide positions 1 to 870 of SEQ ID NO: 1) at the 5'-end and/or the 3'-end of the untranslated nucleic acid sequence.

In some aspects, an untranslated nucleic acid sequence described herein does not comprise any contiguous or non-contiguous nucleotides derived from nucleotides at positions 1 to 860 in the sequence set forth in SEQ ID NO: 1 (resulting in an EF-1α intron fragment comprising, consisting essentially of, or consisting of nucleotides 861 to 924 of SEQ ID NO: 1; i.e., SEQ ID NO: 59). In some aspects, such an untranslated nucleic acid sequence can comprise one or more contiguous or non-contiguous nucleotides derived from within nucleotide positions 1 to 860 of SEQ ID NO: 1 with the proviso that the one or more contiguous or non-contiguous nucleotides is not the entire length of nucleotide positions 1 to 860 of SEQ ID NO: 1 (e.g., shorter than nucleotides 1 to 860 of SEQ ID NO: 1). In some aspects, such an untranslated nucleic acid sequence can comprise one or more different types of nucleotides (i.e., not derived from nucleotide positions 1 to 860 of SEQ ID NO: 1) at the 5'-end and/or the 3'-end of the untranslated nucleic acid sequence.

In some aspects, an untranslated nucleic acid sequence described herein does not comprise any contiguous or non-contiguous nucleotides derived from nucleotides at positions 1 to 851 in the sequence set forth in SEQ ID NO: 1 (resulting in an EF-1α intron fragment comprising, consisting essentially of, or consisting of nucleotides 852 to 924 of SEQ ID NO: 1; i.e., SEQ ID NO: 60). In some aspects, such an untranslated nucleic acid sequence can comprise one or more contiguous or non-contiguous nucleotides derived from within nucleotide positions 1 to 851 of SEQ ID NO: 1 with the proviso that the one or more contiguous or non-contiguous nucleotides is not the entire length of nucleotide positions 1 to 851 of SEQ ID NO: 1 (e.g., shorter than nucleotides 1 to 851 of SEQ ID NO: 1). In some aspects, such an untranslated nucleic acid sequence can comprise one or more different types of nucleotides (i.e., not derived from nucleotide positions 1 to 851 of SEQ ID NO: 1) at the 5'-end and/or the 3'-end of the untranslated nucleic acid sequence.

In some aspects, an untranslated nucleic acid sequence described herein does not comprise any contiguous or non-contiguous nucleotides derived from nucleotides at positions 1 to 850 in the sequence set forth in SEQ ID NO: 1 (resulting in an EF-1α intron fragment comprising, consisting essentially of, or consisting of nucleotides 851 to 924 of SEQ ID NO: 1; i.e., SEQ ID NO: 61). In some aspects, such an untranslated nucleic acid sequence can comprise one or more contiguous or non-contiguous nucleotides derived from within nucleotide positions 1 to 850 of SEQ ID NO: 1 with the proviso that the one or more contiguous or non-contiguous nucleotides is not the entire length of nucleotide positions 1 to 850 of SEQ ID NO: 1 (e.g., shorter than nucleotides 1 to 850 of SEQ ID NO: 1). In some aspects, such an untranslated nucleic acid sequence can comprise one or more different types of nucleotides (i.e., not derived from nucleotide positions 1 to 850 of SEQ ID NO: 1) at the 5'-end and/or the 3'-end of the untranslated nucleic acid sequence.

In some aspects, an untranslated nucleic acid sequence described herein does not comprise any contiguous or non-contiguous nucleotides derived from nucleotides at positions 1 to 829 in the sequence set forth in SEQ ID NO: 1 (resulting in an EF-1α intron fragment comprising, consisting essentially of, or consisting of nucleotides 830 to 924 of SEQ ID NO: 1; i.e., SEQ ID NO: 2). In some aspects, such an untranslated nucleic acid sequence can comprise one or more contiguous or non-contiguous nucleotides derived from within nucleotide positions 1 to 829 of SEQ ID NO: 1 with the proviso that the one or more contiguous or non-contiguous nucleotides is not the entire length of nucleotide positions 1 to 829 of SEQ ID NO: 1 (e.g., shorter than nucleotides 1 to 829 of SEQ ID NO: 1). In some aspects, such an untranslated nucleic acid sequence can comprise one or more different types of nucleotides (i.e., not derived from nucleotide positions 1 to 829 of SEQ ID NO: 1) at the 5'-end and/or the 3'-end of the untranslated nucleic acid sequence.

In some aspects, an untranslated nucleic acid sequence described herein does not comprise any contiguous or non-contiguous nucleotides derived from nucleotides at positions 1 to 820 in the sequence set forth in SEQ ID NO: 1 (resulting in an EF-1α intron fragment comprising, consisting essentially of, or consisting of nucleotides 821 to 924 of SEQ ID NO: 1; i.e., SEQ ID NO: 63). In some aspects, such an untranslated nucleic acid sequence can comprise one or more contiguous or non-contiguous nucleotides derived from within nucleotide positions 1 to 820 of SEQ ID NO: 1 with the proviso that the one or more contiguous or non-contiguous nucleotides is not the entire length of nucleotide positions 1 to 820 of SEQ ID NO: 1 (e.g., shorter than nucleotides 1 to 820 of SEQ ID NO: 1). In some aspects, such an untranslated nucleic acid sequence can comprise one or more different types of nucleotides (i.e., not derived from nucleotide positions 1 to 820 of SEQ ID NO: 1) at the 5'-end and/or the 3'-end of the untranslated nucleic acid sequence.

In some aspects, an untranslated nucleic acid sequence described herein does not comprise any contiguous or non-contiguous nucleotides derived from nucleotides at positions 1 to 810 in the sequence set forth in SEQ ID NO: 1 (resulting in an EF-1α intron fragment comprising, consisting essentially of, or consisting of nucleotides 811 to 924 of SEQ ID NO: 1; i.e., SEQ ID NO: 64). In some aspects, such an untranslated nucleic acid sequence can comprise one or more contiguous or non-contiguous nucleotides derived from within nucleotide positions 1 to 810 of SEQ ID NO: 1 with the proviso that the one or more contiguous or non-contiguous nucleotides is not the entire length of nucleotide positions 1 to 810 of SEQ ID NO: 1 (e.g., shorter than nucleotides 1 to 810 of SEQ ID NO: 1). In some aspects, such an untranslated nucleic acid sequence can comprise one or more different types of nucleotides (i.e., not derived from nucleotide positions 1 to 810 of SEQ ID NO: 1) at the 5'-end and/or the 3'-end of the untranslated nucleic acid sequence.

In some aspects, an untranslated nucleic acid sequence described herein does not comprise any contiguous or non-contiguous nucleotides derived from nucleotides at positions 1 to 807 in the sequence set forth in SEQ ID NO: 1 (resulting in an EF-1α intron fragment comprising, consisting essentially of, or consisting of nucleotides 808 to 924 of SEQ ID NO: 1; i.e., SEQ ID NO: 65). In some aspects, such an untranslated nucleic acid sequence can comprise one or more contiguous or non-contiguous nucleotides derived from within nucleotide positions 1 to 807 of SEQ ID NO: 1 with the proviso that the one or more contiguous or non-contiguous nucleotides is not the entire length of nucleotide positions 1 to 807 of SEQ ID NO: 1 (e.g., shorter than nucleotides 1 to 807 of SEQ ID NO: 1). In some aspects, such an untranslated nucleic acid sequence can comprise one or more different types of nucleotides (i.e., not derived from nucleotide positions 1 to 807 of SEQ ID NO: 1) at the 5'-end and/or the 3'-end of the untranslated nucleic acid sequence.

In some aspects, an untranslated nucleic acid sequence described herein does not comprise any contiguous or non-contiguous nucleotides derived from nucleotides at positions 1 to 800 in the sequence set forth in SEQ ID NO: 1 (resulting in an EF-1α intron fragment comprising, consisting essentially of, or consisting of nucleotides 801 to 924 of SEQ ID NO: 1; i.e., SEQ ID NO: 66). In some aspects, such an untranslated nucleic acid sequence can comprise one or more contiguous or non-contiguous nucleotides derived from within nucleotide positions 1 to 800 of SEQ ID NO: 1 with the proviso that the one or more contiguous or non-contiguous nucleotides is not the entire length of nucleotide positions 1 to 800 of SEQ ID NO: 1 (e.g., shorter than nucleotides 1 to 800 of SEQ ID NO: 1). In some aspects, such an untranslated nucleic acid sequence can comprise one or more different types of nucleotides (i.e., not derived from nucleotide positions 1 to 800 of SEQ ID NO: 1) at the 5'-end and/or the 3'-end of the untranslated nucleic acid sequence.

In some aspects, an untranslated nucleic acid sequence described herein does not comprise any contiguous or non-contiguous nucleotides derived from nucleotides at positions 1 to 750 in the sequence set forth in SEQ ID NO: 1 (resulting in an EF-1α intron fragment comprising, consisting essentially of, or consisting of nucleotides 751 to 924 of SEQ ID NO: 1; i.e., SEQ ID NO: 67). In some aspects, such an untranslated nucleic acid sequence can comprise one or more contiguous or non-contiguous nucleotides derived from within nucleotide positions 1 to 750 of SEQ ID NO: 1 with the proviso that the one or more contiguous or non-contiguous nucleotides is not the entire length of nucleotide positions 1 to 750 of SEQ ID NO: 1 (e.g., shorter than nucleotides 1 to 750 of SEQ ID NO: 1). In some aspects, such an untranslated nucleic acid sequence can comprise one or more different types of nucleotides (i.e., not derived from nucleotide positions 1 to 750 of SEQ ID NO: 1) at the 5'-end and/or the 3'-end of the untranslated nucleic acid sequence.

In some aspects, an untranslated nucleic acid sequence described herein does not comprise any contiguous or non-contiguous nucleotides derived from nucleotides at positions 1 to 720 in the sequence set forth in SEQ ID NO: 1 (resulting in an EF-1α intron fragment comprising, consisting essentially of, or consisting of nucleotides 721 to 924 of SEQ ID NO: 1; i.e., SEQ ID NO: 68). In some aspects, such an untranslated nucleic acid sequence can comprise one or more contiguous or non-contiguous nucleotides derived from within nucleotide positions 1 to 720 of SEQ ID NO: 1 with the proviso that the one or more contiguous or non-contiguous nucleotides is not the entire length of nucleotide positions 1 to 720 of SEQ ID NO: 1 (e.g., shorter than nucleotides 1 to 720 of SEQ ID NO: 1). In some aspects, such an untranslated nucleic acid sequence can comprise one or more different types of nucleotides (i.e., not derived from nucleotide positions 1 to 720 of SEQ ID NO: 1) at the 5'-end and/or the 3'-end of the untranslated nucleic acid sequence.

In some aspects, an untranslated nucleic acid sequence described herein does not comprise any contiguous or non-contiguous nucleotides derived from nucleotides at positions 1 to 700 in the sequence set forth in SEQ ID NO: 1 (resulting in an EF-1α intron fragment comprising, consisting essentially of, or consisting of nucleotides 701 to 924 of SEQ ID NO: 1; i.e., SEQ ID NO: 69). In some aspects, such an untranslated nucleic acid sequence can comprise one or more contiguous or non-contiguous nucleotides derived from within nucleotide positions 1 to 700 of SEQ ID NO: 1 with the proviso that the one or more contiguous or non-contiguous nucleotides is not the entire length of nucleotide positions 1 to 700 of SEQ ID NO: 1 (e.g., shorter than nucleotides 1 to 700 of SEQ ID NO: 1). In some aspects, such an untranslated nucleic acid sequence can comprise one or more different types of nucleotides (i.e., not derived from nucleotide positions 1 to 700 of SEQ ID NO: 1) at the 5'-end and/or the 3'-end of the untranslated nucleic acid sequence.

In some aspects, an untranslated nucleic acid sequence described herein does not comprise any contiguous or non-contiguous nucleotides derived from nucleotides at positions 1 to 650 in the sequence set forth in SEQ ID NO: 1 (resulting in an EF-1α intron fragment comprising, consisting essentially of, or consisting of nucleotides 651 to 924 of SEQ ID NO: 1; i.e., SEQ ID NO: 70). In some aspects, such an untranslated nucleic acid sequence can comprise one or more contiguous or non-contiguous nucleotides derived from within nucleotide positions 1 to 650 of SEQ ID NO: 1 with the proviso that the one or more contiguous or non-contiguous nucleotides is not the entire length of nucleotide positions 1 to 650 of SEQ ID NO: 1 (e.g., shorter than nucleotides 1 to 650 of SEQ ID NO: 1). In some aspects, such an untranslated nucleic acid sequence can comprise one or more different types of nucleotides (i.e., not derived from nucleotide positions 1 to 650 of SEQ ID NO: 1) at the 5'-end and/or the 3'-end of the untranslated nucleic acid sequence.

In some aspects, an untranslated nucleic acid sequence described herein does not comprise any contiguous or non-contiguous nucleotides derived from nucleotides at positions 1 to 600 in the sequence set forth in SEQ ID NO: 1 (resulting in an EF-1α intron fragment comprising, consisting essentially of, or consisting of nucleotides 601 to 924 of SEQ ID NO: 1; i.e., SEQ ID NO: 71). In some aspects, such an untranslated nucleic acid sequence can comprise one or more contiguous or non-contiguous nucleotides derived from within nucleotide positions 1 to 600 of SEQ ID NO: 1 with the proviso that the one or more contiguous or non-contiguous nucleotides is not the entire length of nucleotide positions 1 to 600 of SEQ ID NO: 1 (e.g., shorter than nucleotides 1 to 600 of SEQ ID NO: 1). In some aspects, such an untranslated nucleic acid sequence can comprise one or more different types of nucleotides (i.e., not derived from nucleotide positions 1 to 600 of SEQ ID NO: 1) at the 5'-end and/or the 3'-end of the untranslated nucleic acid sequence.

In some aspects, an untranslated nucleic acid sequence described herein does not comprise any contiguous or non-contiguous nucleotides derived from nucleotides at positions 1 to 569 in the sequence set forth in SEQ ID NO: 1 (resulting in an EF-1α intron fragment comprising, consisting essentially of, or consisting of nucleotides 570 to 924 of SEQ ID NO: 1; i.e., SEQ ID NO: 72). In some aspects, such an untranslated nucleic acid sequence can comprise one or more contiguous or non-contiguous nucleotides derived from within nucleotide positions 1 to 569 of SEQ ID NO: 1 with the proviso that the one or more contiguous or non-contiguous nucleotides is not the entire length of nucleotide positions 1 to 569 of SEQ ID NO: 1 (e.g., shorter than nucleotides 1 to 569 of SEQ ID NO: 1). In some aspects, such an untranslated nucleic acid sequence can comprise one or more different types of nucleotides (i.e., not derived from nucleotide positions 1 to 569 of SEQ ID NO: 1) at the 5'-end and/or the 3'-end of the untranslated nucleic acid sequence.

In some aspects, an untranslated nucleic acid sequence described herein does not comprise any contiguous or non-contiguous nucleotides derived from nucleotides at positions 1 to 550 in the sequence set forth in SEQ ID NO: 1 (resulting in an EF-1α intron fragment comprising, consisting essentially of, or consisting of nucleotides 551 to 924 of SEQ ID NO: 1; i.e., SEQ ID NO: 73). In some aspects, such an untranslated nucleic acid sequence can comprise one or more contiguous or non-contiguous nucleotides derived from within nucleotide positions 1 to 550 of SEQ ID NO: 1 with the proviso that the one or more contiguous or non-contiguous nucleotides is not the entire length of nucleotide positions 1 to 550 of SEQ ID NO: 1 (e.g., shorter than nucleotides 1 to 550 of SEQ ID NO: 1). In some aspects, such an untranslated nucleic acid sequence can comprise one or more different types of nucleotides (i.e., not derived from nucleotide positions 1 to 550 of SEQ ID NO: 1) at the 5'-end and/or the 3'-end of the untranslated nucleic acid sequence.

In some aspects, an untranslated nucleic acid sequence described herein does not comprise any contiguous or non-contiguous nucleotides derived from nucleotides at positions 1 to 500 in the sequence set forth in SEQ ID NO: 1 (resulting in an EF-1α intron fragment comprising, consisting essentially of, or consisting of nucleotides 501 to 924 of SEQ ID NO: 1; i.e., SEQ ID NO: 74). In some aspects, such an untranslated nucleic acid sequence can comprise one or more contiguous or non-contiguous nucleotides derived from within nucleotide positions 1 to 500 of SEQ ID NO: 1 with the proviso that the one or more contiguous or non-contiguous nucleotides is not the entire length of nucleotide positions 1 to 500 of SEQ ID NO: 1 (e.g., shorter than nucleotides 1 to 500 of SEQ ID NO: 1). In some aspects, such an untranslated nucleic acid sequence can comprise one or more different types of nucleotides (i.e., not derived from nucleotide positions 1 to 500 of SEQ ID NO: 1) at the 5'-end and/or the 3'-end of the untranslated nucleic acid sequence.

In some aspects, an untranslated nucleic acid sequence described has at least about 70%, at least about 80%, at least about 85%, at least about 90%, at least about 95%, at least about 96%, at least about 97%, at least about 98%, at least about 99%, or about 100% sequence identity to (i) nucleotides 871 to 924 of SEQ ID NO: 1 (i.e., SEQ ID NO: 58), (ii) nucleotides 861 to 924 of SEQ ID NO: 1 (i.e., SEQ ID NO: 59), (iii) nucleotides 852 to 924 of SEQ ID NO: 1 (i.e., SEQ ID NO: 60), (iv) nucleotides 851 to 924 of SEQ ID NO: 1 (i.e., SEQ ID NO: 61), (v) nucleotides 830 to 924 of SEQ ID NO: 1 (i.e., SEQ ID NO: 2), (vi) nucleotides 821 to 924 of SEQ ID NO: 1 (i.e., SEQ ID NO: 63), (vii) nucleotides 811 to 924 of SEQ ID NO: 1 (i.e., SEQ ID NO: 64), (viii) nucleotides 808 to 924 of SEQ ID NO: 1 (i.e., SEQ ID NO: 65), (ix) nucleotides 801 to 924 of SEQ ID NO: 1 (i.e., SEQ ID NO: 66), (x) nucleotides 751 to 924 of SEQ ID NO: 1 (i.e., SEQ ID NO: 67), (xi) nucleotides 721 to 924 of SEQ ID NO: 1 (i.e., SEQ ID NO: 68), (xii) nucleotides 701 to 924 of SEQ ID NO: 1 (i.e., SEQ ID NO: 69), (xiii) nucleotides 651 to 924 of SEQ ID NO: 1 (i.e., SEQ ID NO: 70), (xiv) nucleotides 601 to 924 of SEQ ID NO: 1 (i.e., SEQ ID NO: 71), (xv) nucleotides 570 to 924 of SEQ ID NO: 1 (i.e., SEQ ID NO: 72), (xvi) nucleotides 551 to 924 of SEQ ID NO: 1 (i.e., SEQ ID NO; 73), or (xvii) nucleotides 501 to 924 of SEQ ID NO: 1 (i.e., SEQ ID NO: 74).

In some aspects, the untranslated nucleic acid sequence has at least about 70%, at least about 80%, at least about 85%, at least about 90%, at least about 95%, at least about 96%, at least about 97%, at least about 98%, at least about 99%, or about 100% sequence identity to nucleotides 871 to 924 of SEQ ID NO: 1 (i.e., SEQ ID NO: 58). In some aspects, the untranslated nucleic acid sequence has at least about 70%, at least about 80%, at least about 85%, at least about 90%, at least about 95%, at least about 96%, at least about 97%, at least about 98%, at least about 99%, or about 100% sequence identity to nucleotides 861 to 924 of SEQ ID NO: 1 (i.e., SEQ ID NO: 59). In some aspects, the untranslated nucleic acid sequence has at least about 70%, at least about 80%, at least about 85%, at least about 90%, at least about 95%, at least about 96%, at least about 97%, at least about 98%, at least about 99%, or about 100% sequence identity to nucleotides 852 to 924 of SEQ ID NO: 1 (i.e., SEQ ID NO: 60). In some aspects, the untranslated nucleic acid sequence has at least about 70%, at least about 80%, at least about 85%, at least about 90%, at least about 95%, at least about 96%, at least about 97%, at least about 98%, at least about 99%, or about 100% sequence identity to nucleotides 851 to 924 of SEQ ID NO: 1 (i.e., SEQ ID NO: 61). In some aspects, the untranslated nucleic acid sequence has at least about 70%, at least about 80%, at least about 85%, at least about 90%, at least about 95%, at least about 96%, at least about 97%, at least about 98%, at least about 99%, or about 100% sequence identity to nucleotides 830 to 924 of SEQ ID NO: 1 (i.e., SEQ ID NO: 2). In some aspects, the untranslated nucleic acid sequence has at least about 70%, at least about 80%, at least about 85%, at least about 90%, at least about 95%, at least about 96%, at least about 97%, at least about 98%, at least about 99%, or about 100% sequence identity to nucleotides 821 to 924 of SEQ ID NO: 1 (i.e., SEQ ID NO: 63). In some aspects, the untranslated nucleic acid sequence has at least about 70%, at least about 80%, at least about 85%, at least about 90%, at least about 95%, at least about 96%, at least about 97%, at least about 98%, at least about 99%, or about 100% sequence identity to nucleotides 811 to 924 of SEQ ID NO: 1 (i.e., SEQ ID NO: 64). In some aspects, the untranslated nucleic acid sequence has at least about 70%, at least about 80%, at least about 85%, at least about 90%, at least about 95%, at least about 96%, at least about 97%, at least about 98%, at least about 99%, or about 100% sequence identity to nucleotides 808 to 924 of SEQ ID NO: 1 (i.e., SEQ ID NO: 65). In some aspects, the untranslated nucleic acid sequence has at least about 70%, at least about 80%, at least about 85%, at least about 90%, at least about 95%, at least about 96%, at least about 97%, at least about 98%, at least about 99%, or about 100% sequence identity to nucleotides 801 to 924 of SEQ ID NO: 1 (i.e., SEQ ID NO: 66). In some aspects, the untranslated nucleic acid sequence has at least about 70%, at least about 80%, at least about 85%, at least about 90%, at least about 95%, at least about 96%, at least about 97%, at least about 98%, at least about 99%, or about 100% sequence identity to nucleotides 751 to 924 of SEQ ID NO: 1 (i.e., SEQ ID NO: 67). In some aspects, the untranslated nucleic acid sequence has at least about 70%, at least about 80%, at least about 85%, at least about 90%, at least about 95%, at least about 96%, at least about 97%, at least about 98%, at least about 99%, or about 100% sequence identity to nucleotides 721 to 924 of SEQ ID NO: 1 (i.e., SEQ ID NO: 68). In some aspects, the untranslated nucleic acid sequence has at least about 70%, at least about 80%, at least about 85%, at least about 90%, at least about 95%, at least about 96%, at least about 97%, at least about 98%, at least about 99%, or about 100% sequence identity to nucleotides 701 to 924 of SEQ ID NO: 1 (i.e., SEQ ID NO: 69). In some aspects, the untranslated nucleic acid sequence has at least about 70%, at least about 80%, at least about 85%, at least about 90%, at least about 95%, at least about 96%, at least about 97%, at least about 98%, at least about 99%, or about 100% sequence identity to nucleotides 651 to 924 of SEQ ID NO: 1 (i.e., SEQ ID NO: 70). In some aspects, the untranslated nucleic acid sequence has at least about 70%, at least about 80%, at least about 85%, at least about 90%, at least about 95%, at least about 96%, at least about 97%, at least about 98%, at least about 99%, or about 100% sequence identity to nucleotides 601 to 924 of SEQ ID NO: 1 (i.e., SEQ ID NO: 71). In some aspects, the untranslated nucleic acid sequence has at least about 70%, at least about 80%, at least about 85%, at least about 90%, at least about 95%, at least about 96%, at least about 97%, at least about 98%, at least about 99%, or about 100% sequence identity to nucleotides 570 to 924 of SEQ ID NO: 1 (i.e., SEQ ID NO: 72). In some aspects, the untranslated nucleic acid sequence has at least about 70%, at least about 80%, at least about 85%, at least about 90%, at least about 95%, at least about 96%, at least about 97%, at least about 98%, at least about 99%, or about 100% sequence identity to, nucleotides 551 to 924 of SEQ ID NO: 1 (i.e., SEQ ID NO; 73). In some aspects, the untranslated nucleic acid sequence has at least about 70%, at least about 80%, at least about 85%, at least about 90%, at least about 95%, at least about 96%, at least about 97%, at least about 98%, at least about 99%, or about 100% sequence identity to nucleotides 501 to 924 of SEQ ID NO: 1 (i.e., SEQ ID NO: 74).

As is apparent from the above disclosure, in some aspects, a polynucleotide comprising an untranslated nucleic acid sequence described herein comprises at least about one, at least about two, at least three, at least about four, at least about five, at least about 10, at least about 15, at least about 20, at least about 25, at least about 30, at least about 40, at least about 50, at least about 60, at least about 70, at least about 80, at least about 90, or at least about 100 additional nucleotides at the 5' terminus ("5' region") of the untranslated nucleic acid sequence. In some aspects, a polynucleotide described herein comprises at least about one, at least about two, at least three, at least about four, at least about five, at least about 10, at least about 15, at least about 20, at least about 25, at least about 30, at least about 40, at least about 50, at least about 60, at least about 70, at least about 80, at least about 90, or at least about 100 additional nucleotides at the 3' terminus ("3' region") of the untranslated nucleic acid sequence. In some aspects, a polynucleotide comprising an untranslated nucleic acid sequence comprises at least about one, at least about two, at least three, at least about four, at least about five, at least about 10, at least about 15, at least about 20, at least about 25, at least about 30, at least about 40, at least about 50, at least about 60, at least about 70, at least about 80, at least about 90, or at least about 100 additional nucleotides at both the 5' region and the 3' region of the untranslated nucleic acid sequence.

In some aspects, a polynucleotide comprises one or more contiguous or non-contiguous nucleotides corresponding to positions 1 to 873 in SEQ ID NO: 1 at the 5' region of the untranslated nucleic acid sequence.

II.B. Transgene

In some aspects, a polynucleotide comprising an untranslated nucleic acid sequence described herein further comprises a transgene. Accordingly, in some aspects, a polynucleotide described herein comprises a transgene and an untranslated nucleic acid sequence, wherein the untranslated nucleic acid sequence comprises, consists essentially of, or consists of nucleotides 874 to 924 of SEQ ID NO: 1 but does not comprise SEQ ID NO: 1 (e.g., SEQ ID NO: 57). In some aspects, a polynucleotide described herein comprises a transgene and an untranslated nucleic acid sequence, wherein the untranslated nucleic acid sequence comprises, consists essentially of, or consists of nucleotides 852-924 of SEQ ID NO: 1 but does not comprise SEQ ID NO: 1 (e.g., SEQ ID NO: 3). In some aspects, a polynucleotide described herein comprises a transgene and an untranslated nucleic acid sequence, wherein the untranslated nucleic acid sequence comprises, consists essentially of, or consists of nucleotides 830-924 of SEQ ID NO: 1 but does not comprise SEQ ID NO: 1 (e.g., SEQ ID NO: 2).

Transgenes useful for the present disclosure is not particularly limited as long as the transgene can be translated into a polypeptide when transduced into a cell. Accordingly, any suitable transgenes of interest can be used with the untranslated nucleic acid sequences of the present disclosure. In some aspects, a transgene encodes a polypeptide (or any variant thereof), fusion protein, antibody or an antigen-binding fragment thereof, a RNA-based molecule (e.g., miRNA, shRNA, ribozyme, siRNA), or any combination thereof.

In some aspects, a transgene encodes a protein that is useful for the treatment of a disease or disorder, such as those described herein. In some aspects, the transgene encodes a therapeutic peptide for a specific disease for the purpose of sustained expression in the body of a subject or patient. In some aspects, a transgene comprises a nucleotide sequence which has at least about 70%, at least about 80%, at least about 85%, at least about 90%, at least about 95%, at least about 96%, at least about 97%, at least about 98%, at least about 99%, or about 100% sequence identity to SEQ ID NO: 23. In some aspects, the transgene encodes a fusion protein, wherein the fusion protein is an inhibitor of a vascular endothelial growth factor ("VEGF"). In some aspects, the inhibitor of VEGF comprises aflibercept (EY-LEA® and ZALTRAP®).

II.C. Control Element

In some aspects, a polynucleotide described herein further comprises a control element. Accordingly, in some aspects, a polynucleotide comprises (1) a control element, (2) an untranslated nucleic acid sequence described herein, and (3) a transgene.

As used herein, the term "control element" refers to a nucleic acid sequence that regulate (e.g., increase or decrease) the expression of an operably linked nucleic acid. Control elements useful for the present disclosure comprises an enhancer (e.g., a CMV enhancer), a promoter (e.g., a CMV promoter, an EF-1α promoter, or a β-actin promoter), an exon (e.g., exon 1 or exon 2), splicing donor sequence, receptor sequences, or combinations thereof. In some aspects, the control element can include a sequence for transcription termination (e.g., poly A), a sequence for stable transgene expression (e.g., a WPRE sequence), a sequence for the reduction of transgene-specific immunity (e.g., a miRNA target sequence), or combinations thereof.

II. C.1. Enhancer

In some aspects, the control element is an enhancer. Accordingly, in some aspects, a polynucleotide described herein comprises (in no particular order) (1) an enhancer, (2) an untranslated nucleic acid sequence, and (3) a transgene. In some aspects, a polynucleotide described herein comprises (from 5' to 3'): (1) an enhancer, (2) an untranslated nucleic acid sequence, and (3) a transgene.

Any suitable enhancers known in the art can be used with the present disclosure. Non-limiting examples of suitable enhancers include: a cytomegalovirus (CMV) enhancer, a SV40 early enhancer, an adenovirus 5 E1A enhancer, a HBV enhancer-1 regulatory region (Eh-1), a HPV-16 or -18 E6/7 long control region (LCR), a HIV-1 long terminal repeat (LTR), or any combination thereof. In some aspects, the enhancer is a cytomegalovirus (CMV) enhancer. In some aspects, the CMV enhancer comprises a sequence having at least about 70%, at least about 80%, at least about 85%, at least about 90%, at least about 95%, at least about 96%, at least about 97%, at least about 98%, at least about 99%, or about 100% sequence identity to SEQ ID NO: 4. In some aspects, the cytomegalovirus (CMV) enhancer includes the nucleotide sequence set forth in SEQ ID NO: 4.

II.C.2. Promoter

In some aspects, the control element is a promoter. Accordingly, in some aspects, a polynucleotide described herein comprises (in no particular order) (1) a promoter, (2) an untranslated nucleic acid sequence, and (3) a transgene. In some aspects, a polynucleotide comprises (from 5' to 3'): (1) a promoter, (2) an untranslated nucleic acid sequence, and (3) a transgene. In some aspects, the control element comprises both an enhancer and a promoter. In such aspects, a polynucleotide can comprise (in no particular order) (1) an enhancer, (2) a promoter, (3) an untranslated nucleic acid sequence, and (4) a transgene. In some aspects, a polynucleotide comprises (from 5' to 3'): (1) an enhancer, (2) a promoter, (3) an untranslated nucleic acid sequence, and (4) a transgene. Any suitable promoters known in the art can be used with the present disclosure.

In some aspects, the promoter comprises a cytomegalovirus (CMV) promoter, an EF-1α promoter, a β-actin promoter, a glyceraldehyde 3-phosphate dehydrogenase (GAPDH) promoter, a 70-kDa heat shock protein (HSP70) promoter, a 78-kDa glucose-regulated protein (GRP78) promoter, an eukaryotic initiation factor-4A (eIF4a) promoter, an alpha-1-antitrypsin (AAT) promoter, a transthyretin (TTR) promoter, a glial fibrillary acidic protein (GFAP) promoter, an early promoter of simian vaculating virus 40 (SV40) promoter, a synapsin I (SYN1) promoter, a G protein-coupled receptor kinases (GRK) promoter, a rhodopsin (Rho) promoter, or combinations thereof.

In some aspects, a promoter useful for the present disclosure is a CMV promoter. Accordingly, in some aspects, a polynucleotide comprises (1) an enhancer (e.g., CMV enhancer), (2) a CMV promoter, (3) an untranslated nucleic acid sequence, and (4) a transgene. In some aspects, the CMV promoter comprises a sequence having at least about 70%, at least about 80%, at least about 85%, at least about 90%, at least about 95%, at least about 96%, at least about 97%, at least about 98%, at least about 99%, or about 100% sequence identity to SEQ ID NO: 5 or 6. In some aspects, the CMV promoter includes the nucleotide sequence set forth in SEQ ID NO: 5 or 6.

In some aspects, a promoter that can be used with the present disclosure is an EF-1α promoter. In some aspects, a polynucleotide comprises (1) an enhancer (e.g., CMV enhancer), (2) an EF-1α promoter, (3) an untranslated nucleic acid sequence, and (4) a transgene. In some aspects, the EF-1α promoter comprises a sequence having at least about 70%, at least about 80%, at least about 85%, at least about 90%, at least about 95%, at least about 96%, at least about 97%, at least about 98%, at least about 99%, or about 100% sequence identity to SEQ ID NO: 7. In some aspects, the EF-1α promoter includes the nucleotide sequence set forth in SEQ ID NO: 7.

In some aspects, the promoter is a β-actin promoter. Therefore, in some aspects, a polynucleotide described herein comprises (1) an enhancer (e.g., CMV enhancer), (2) a β-actin promoter, (3) an untranslated nucleic acid sequence, and (4) a transgene. In some aspects, the β-actin promoter comprises a sequence having at least about 70%, at least about 80%, at least about 85%, at least about 90%, at least about 95%, at least about 96%, at least about 97%, at least about 98%, at least about 99%, or about 100% sequence identity to SEQ ID NO: 8. In some aspects, the β-actin promoter is a chicken β-actin promoter, such as that set forth in SEQ ID NO: 8.

As demonstrated herein (see FIG. 4A), in some aspects, a polynucleotide described herein (e.g., comprising a transgene and an untranslated nucleic acid sequence) can comprise multiple promoters. For instance, in some aspects, a polynucleotide comprises a combination of a CMV promoter, EF-1α promoter, and/or β-actin promoter. In some aspects, a polynucleotide comprises both a CMV promoter and an EF-1α promoter. In such aspects, the CMV promoter can be a portion of the full-length CMV promoter, such as the sequence set forth in SEQ ID NO: 5 (i.e., first 31 nucleotides from the 5'-end of SEQ ID NO: 6).

II.C.3. Splicing Donor Sequence

In some aspects, a polynucleotide described herein (i.e., comprising an untranslated nucleic acid sequence) comprises a splicing donor sequence. As used herein, the term "splicing donor sequence" or "splicing donor site" refers to a guanine-thymine (GT) rich domain present at the 5'-end of an intron (e.g., EF-1α intron) (signals the border between introns and exons). As demonstrated herein, such sequences can be targeted to produce the untranslated nucleic acid sequences of the present disclosure. In some aspects, a splicing donor sequence is linked upstream of the EF-1α intron fragment (i.e., untranslated nucleic acid sequence). For instance, in some aspects, a polynucleotide described herein comprises (in no particular order) (1) an enhancer (e.g., CMV enhancer), (2) a promoter (e.g., CMV promoter, EF-1α promoter, and/or β-actin promoter), (3) a splicing donor sequence, (4) an untranslated nucleic acid sequence, and (5) a transgene. In some aspects, a polynucleotide comprises (from 5' to 3'): (1) an enhancer (e.g., CMV enhancer), (2) a promoter (e.g., CMV promoter, EF-1α promoter, and/or β-actin promoter), (3) a splicing donor sequence, (4) an untranslated nucleic acid sequence, and (5) a transgene.

In some aspects, a splicing donor sequence useful for the present disclosure has at least about 70%, at least about 80%, at least about 85%, at least about 90%, at least about 95%, at least about 96%, at least about 97%, at least about 98%, at least about 99%, or about 100% sequence identity to the nucleotide sequence set forth in SEQ ID NO: 9 or SEQ ID NO: 10. In some aspects, the splicing donor sequence includes the nucleotide sequence set forth in SEQ ID NO: 9 or 10.

II.C.4. Exon Sequences

As demonstrated herein, in some aspects, a polynucleotide of the present disclosure further comprises one or more exon sequences. For instance, in some aspects, a polynucleotide described herein includes an EF-1α exon 2 (E2) sequence. Accordingly, in some aspects, a polynucleotide described herein comprises the following features (in no particular order): (1) an enhancer (e.g., CMV enhancer), (2) a promoter (e.g., CMV promoter, EF-1α promoter, and/or β-actin promoter), (3) a splicing donor sequence, (4) an untranslated nucleic acid sequence, (5) an EF-1α E2 sequence, and (6) a transgene. In some aspects, such a polynucleotide comprises (from 5' to 3'): (1) an enhancer (e.g., CMV enhancer), (2) a promoter (e.g., CMV promoter, EF-1α promoter, and/or β-actin promoter), (3) a splicing donor sequence, (4) an untranslated nucleic acid sequence, (5) an EF-1α E2 sequence, and (6) a transgene. In some aspects, the EF-1α E2 sequence has at least about 70%, at least about 80%, at least about 85%, at least about 90%, at least about 95%, at least about 96%, at least about 97%, at least about 98%, at least about 99%, or about 100% sequence identity to SEQ ID NO: 11. In some aspects, the EF-1α E2 sequence includes the nucleotide sequence set forth in SEQ ID NO: 11.

In some aspects, the one or more exon sequences that can be included in a polynucleotide described herein comprises a cytomegalovirus (CMV), EF-1α or β-actin exon 1 (E1) sequence. In some aspects, a polynucleotide described herein can comprise both the E1 and E2 sequences. For instance, in some aspects, a polynucleotide comprises (in no particular order): (1) an enhancer (e.g., CMV enhancer), (2) a promoter (e.g., CMV promoter, EF-1α promoter, and/or β-actin promoter), (3) an E1 sequence (e.g., CMV E1 sequence, EF-1α E1 sequence, and/or β-actin E1 sequence), (4) a splicing donor sequence, (5) an untranslated nucleic acid sequence, (6) an EF-1α E2 sequence, and (7) a transgene. In some aspects, a polynucleotide comprises (from 5' to 3'): (1) an enhancer (e.g., CMV enhancer), (2) a promoter (e.g., CMV promoter, EF-1α promoter, and/or β-actin promoter), (3) an E1 sequence (e.g., CMV E1 sequence, EF-1α E1 sequence, and/or β-actin E1 sequence), (4) a splicing donor sequence, (5) an untranslated nucleic acid sequence, (6) an EF-1α E2 sequence, and (7) a transgene.

In some aspects, the E1 sequence that can be used with the present disclosure is a CMV E1 sequence. In some aspects, the CMV E1 sequence has at least about 70%, at least about 80%, at least about 85%, at least about 90%, at least about 95%, at least about 96%, at least about 97%, at least about 98%, at least about 99%, or about 100% sequence identity to SEQ ID NO: 12. In some aspects, the CMV E1 sequence includes the nucleotide sequence set forth in SEQ ID NO: 12.

In some aspects, the E1 sequence is an EF-1α E1 sequence. In some aspects, the EF-1α E1 sequence has at least about 70%, at least about 80%, at least about 85%, at least about 90%, at least about 95%, at least about 96%, at least about 97%, at least about 98%, at least about 99%, or about 100% sequence identity to SEQ ID NO: 13. In some aspects, the EF-1α E1 sequence includes the nucleotide sequence set forth in SEQ ID NO: 13.

In some aspects, the E1 sequence is a β-actin E1 sequence. In some aspects, the β-actin E1 sequence has at least about 70%, at least about 80%, at least about 85%, at least about 90%, at least about 95%, at least about 96%, at least about 97%, at least about 98%, at least about 99%, or about 100% sequence identity to SEQ ID NO: 14 or 15 In some aspects, the β-actin E1 sequence includes the nucleotide sequence set forth in SEQ ID NO: 14 or 15.

II.C.5. miRNA Target Sequences

As described herein, in some aspects, the control element of a polynucleotide described herein comprises one or more target sequences for microRNA (miRNA) specific to immune cells ("miRNA target sequences"). Accordingly, in some aspects, a polynucleotide described herein comprises the following features (in no particular order): (1) an enhancer (e.g., CMV enhancer), (2) a promoter (e.g., CMV promoter, EF-1α promoter, and/or β-actin promoter), (3) an E1 sequence (e.g., CMV E1 sequence, EF-1α E1 sequence, and/or β-actin E1 sequence), (4) a splicing donor sequence, (5) an untranslated nucleic acid sequence, (6) an EF-1α E2 sequence, (7) a transgene, and (8) one or more miRNA target sequences. In some aspects, a polynucleotide comprises (from 5' to 3'): (1) an enhancer (e.g., CMV enhancer), (2) a promoter (e.g., CMV promoter, EF-1α promoter, and/or β-actin promoter), (3) an E1 sequence (e.g., CMV E1 sequence, EF-1α E1 sequence, and/or β-actin E1 sequence), (4) a splicing donor sequence, (5) an untranslated nucleic acid sequence, (6) an EF-1α E2 sequence, (7) a transgene, and (8) one or more miRNA target sequences.

In some aspects, a polynucleotide described herein comprises one, two, three, four, five, six, seven, eight, nine, or ten or more miRNA target sequences. In some aspects, the number of the target sequences for miRNA that can be included in a polynucleotide described herein is about two to about six (e.g., 2 to 6). In some aspects, the multiple miRNA target sequences are the same. In some aspects, one or more of the multiple miRNA target sequences are different.

As is apparent from the present disclosure, the inclusion of one or more miRNA target sequences can enhance the specificity of the polynucleotides described herein. For instance, where inhibition of the transgene is desirable in certain cell types (e.g., immune cells), the target sequences for miRNA specific to immune cells can be used to inhibit the expression of transgenes in immune cells, with the result that the generation of transgene-specific immunity by immune cells can be blocked. Accordingly, by using different miRNA target sequences, the expression of the transgene in different cells/tissues can be regulated.

Any suitable miRNA target sequences known in the art can be used with the present disclosure. In some aspects, the miRNA target sequences are specific for miR142-3p or miR142-5p. In some aspects, the target sequences for miRNA are selected from antisense oligonucleotides, antagomirs, small hairpin RNA (shRNA) molecules, small interfering RNA (siRNA) molecules, ribozymes, peptide nucleic acids (PNA) oligonucleotides, locked nucleic acid (LNA) oligonucleotides, or combinations thereof, that have sequences complementary to the full-length or partial sequence of miR142-3p or miR142-5p.

In some aspects, the miRNA target sequence has at least about 70%, at least about 80%, at least about 85%, at least about 90%, at least about 95%, at least about 96%, at least about 97%, at least about 98%, at least about 99%, or about 100% sequence identity to SEQ ID NO: 16. In some aspects, the miRNA target sequence has at least about 70%, at least about 80%, at least about 85%, at least about 90%, at least about 95%, at least about 96%, at least about 97%, at least about 98%, at least about 99%, or about 100% sequence identity to SEQ ID NO: 17. In some aspects, the miRNA target sequence includes the nucleotide sequence set forth in SEQ ID NO: 16 or SEQ ID NO: 17.

II.C.6. WPRE Sequences

In some aspects, a polynucleotide described herein (i.e., comprising an untranslated nucleic acid sequence) further comprises a woodchuck hepatitis virus posttranscriptional regulatory element (WPRE) sequence. Accordingly, in some aspects, a polynucleotide described herein comprises (in no particular order) (1) an enhancer (e.g., CMV enhancer), (2) a promoter (e.g., CMV promoter, EF-1α promoter, and/or β-actin promoter), (3) an E1 sequence (e.g., CMV E1 sequence, EF-1α E1 sequence, and/or β-actin E1 sequence), (4) a splicing donor sequence, (5) an untranslated nucleic acid sequence, (6) an EF-1α E2 sequence, (7) a transgene, (8) one or more miRNA target sequences, and (9) a WPRE sequence. In some aspects, a polynucleotide described herein comprises (from 5' to 3'): (1) an enhancer (e.g., CMV enhancer), (2) a promoter (e.g., CMV promoter, EF-1α promoter, and/or β-actin promoter), (3) an E1 sequence (e.g., CMV E1 sequence, EF-1α E1 sequence, and/or β-actin E1 sequence), (4) a splicing donor sequence, (5) an untranslated nucleic acid sequence, (6) an EF-1α E2 sequence, (7) a transgene, (8) one or more miRNA target sequences, and (9) a WPRE sequence.

In some aspects, the WPRE sequence has at least about 70%, at least about 80%, at least about 85%, at least about 90%, at least about 95%, at least about 96%, at least about 97%, at least about 98%, at least about 99%, or about 100% sequence identity to SEQ ID NO: 18. In some aspects, the WPRE sequence includes the nucleotide sequence set forth in SEQ ID NO: 18.

II.C.7. Polyadenylation Sequences

In some aspects, a polynucleotide described herein (i.e., comprising an untranslated nucleic acid sequence) further includes one or more polyadenylation (pA) sequences. Accordingly, in some aspects, a polynucleotide comprises (in no particular order): (1) an enhancer (e.g., CMV enhancer), (2) a promoter (e.g., CMV promoter, EF-1α promoter, and/or β-actin promoter), (3) an E1 sequence (e.g., CMV E1 sequence, EF-1α E1 sequence, and/or β-actin E1 sequence), (4) a splicing donor sequence, (5) an untranslated nucleic acid sequence, (6) an EF-1α E2 sequence, (7) a transgene, (8) one or more miRNA target sequences, (9) a WPRE sequence, and (10) one or more pA sequences. In some aspects, a polynucleotide comprises (from 5' to 3'): (1) an enhancer (e.g., CMV enhancer), (2) a promoter (e.g., CMV promoter, EF-1α promoter, and/or β-actin promoter), (3) an E1 sequence (e.g., CMV E1 sequence, EF-1α E1 sequence, and/or β-actin E1 sequence), (4) a splicing donor sequence, (5) an untranslated nucleic acid sequence, (6) an EF-1α E2 sequence, (7) a transgene, (8) one or more miRNA target sequences, (9) a WPRE sequence, and (10) one or more pA sequences.

Any suitable pA sequences known in the art can be used with the present disclosure. In some aspects, Examples of polyadenylation sequences include human growth hormone (hGH) pA sequences, bovine growth hormone (bGH) pA sequences, simian vaculating virus 40 (SV40) early pA sequences, and SV40 late pA sequences, but are not limited thereto.

In some aspects, the pA sequence has at least about 70%, at least about 80%, at least about 85%, at least about 90%, at least about 95%, at least about 96%, at least about 97%, at least about 98%, at least about 99%, or about 100% sequence identity to SEQ ID NO: 19. In some aspects, the pA sequence has at least about 70%, at least about 80%, at least about 85%, at least about 90%, at least about 95%, at least about 96%, at least about 97%, at least about 98%, at least about 99%, or about 100% sequence identity to SEQ ID NO: 20. In some aspects, the pA sequence has at least about 70%, at least about 80%, at least about 85%, at least about 90%, at least about 95%, at least about 96%, at least about 97%, at least about 98%, at least about 99%, or about 100% sequence identity to SEQ ID NO: 21. In some aspects, the pA sequence has at least about 70%, at least about 80%, at least about 85%, at least about 90%, at least about 95%, at least about 96%, at least about 97%, at least about 98%, at least about 99%, or about 100% sequence identity to SEQ ID NO: 22. In some aspects, the polyadenylation sequences are selected from the group consisting of the nucleotide sequences set forth in SEQ ID NOs: 19 to 22.

As described above, in some aspects, a polynucleotide described herein comprises (i) a transgene (e.g., SEQ ID NO: 23) and (ii) a control element operably linked to the transgene, wherein the control element comprises (from 5' to 3'): (1) the CMV enhancer sequence set forth in SEQ ID NO: 4, (2) the CMV promoter sequence set forth in SEQ ID NO: 5 or 6, the EF-1α promoter sequence set forth in SEQ ID NO: 7, or the chicken β-actin promoter sequence set forth in SEQ ID NO: 8, (3) the CMV E1 sequence set forth in SEQ ID NO: 12, the EF-1α E1 sequence set forth in SEQ ID NO: 13, or the chicken β-actin E1 sequence set forth in SEQ ID NO: 14 or 15, (4) the splicing donor sequence set forth in SEQ ID NO: 9 or 10, (5) the EF-1α intron fragment sequence (i.e., untranslated nucleic acid sequence) comprising, consisting essentially of, or consisting of the nucleotide sequence set forth in SEQ ID NO: 2, SEQ ID NO: 3, or SEQ ID NO: 57, and (6) the EF-1α E2 sequence set forth in SEQ ID NO: 11.

III. Vectors

In some aspects, provided herein are vectors (e.g., expression vectors) comprising any of the polynucleotides described herein (e.g., comprising a transgene and an untranslated nucleic acid sequence). As described herein, such vectors are useful for recombinant expression in host cells and cells targeted for therapeutic intervention. In some aspects, a vector useful for the delivery of a polynucleotide described herein (e.g., comprising a transgene and an untranslated nucleic acid sequence) comprises a viral vector. Examples of viruses that can be used as vectors in the present disclosure include, but are not limited to, retroviruses, herpes simplex viruses, lentiviruses, poxviruses, vaccinia viruses, rhabdoviruses, adenoviruses, helper-dependent adenoviruses, adeno-associated viruses (AAVs), baculovirus, and combinations thereof. In some aspects, a vector that can be used with the present disclosure comprises a non-viral vector. Non-limiting examples of such vectors include a plasmid, cosmid, yeast artificial chromosome (YAC), bacteriophage, and combinations thereof.

III.A. Adeno-Associated Virus (AAV)

In some aspects, polynucleotides described herein (e.g., comprising a transgene and an untranslated nucleic acid sequence) are delivered, e.g., to a cell, using an AAV. Adeno-associated viruses (AAVs) as single-stranded DNA viruses are helper-dependent human parvoviruses. The AAV genome has a size of about 4.7 kbp and consists of an N-terminus encoding the rep gene involved in viral replication and the expression of viral genes, a C-terminus coding for the cap gene encoding the capsid protein of the virus, and an inverted terminal repeat (ITR) with about 145 base insertions at each terminus. The 145 bp inverted terminal repeat (ITR) has a T-shaped structure, serves as an origin of replication during viral genome replication, and functions as a primary packaging signal. The ITR is only a cis-acting nucleotide sequence required to prepare a recombinant AAV (rAAV) construct. The ITR has an enhancer activity in the presence of the Rep protein but its activity is very weak in the absence of the Rep protein. In view of these features, when a transgene is cloned into a recombinant AAV construct, an enhancer, a promoter, pA, etc. are properly assembled to prepare an expression construct (R J Samulski and N Muzyczka, Annu. Rev. Virolo. 2014. 1:427-451). Four proteins are translated from the rep gene. These proteins are classified into rep78, rep68, rep52, and rep40 by their molecular weight and perform important functions in AAV DNA replication. Four proteins are translated from the cap gene. Of these, VP1, VP2, and VP3 proteins are structural proteins constituting AAV particles and the assembly-activating protein (AAP) promotes the assembly of AAV particles by the structural proteins. Some proteins and RNAs derived from helper viruses such as adenoviruses or herpes simplex viruses are required for efficient replication of adeno-associated viruses (Muzyczka N. Curr Top Microbiol Immunol 158, 97-129, 1992).

AAV possesses unique features that make it attractive as a vector system for delivering foreign DNA into cells. AAV infection of cells in culture has generally been noncytopathic, and natural infection of humans and other animals is silent and asymptomatic. Moreover, AAV infects many different types of mammalian cells allowing the possibility of targeting many different tissues in vivo. AAV also possesses additional advantages that make it a particularly attractive viral system for gene delivery, including the promotion of an immune response that is relatively mild compared to other forms of gene delivery, and persistent expression in both dividing and quiescent cells based on non-integrating, episomal vector DNA. Also, AAV withstands the conditions used to inactivate adenovirus (56° to 65° C. for several hours), making cold preservation of rAAV-based vaccines less critical.

The types or serotypes of adeno-associated viruses that can be used with the present disclosure includes AAVrh.10 (AAVrh10), AAV-DJ (AAVDJ), AAV-DJ8 (AAVDJ8), AAV1, AAV2, AAV2G9, AAV3, AAV3a, AAV3b, AAV3-3, AAV4, AAV4-4, AAV5, AAV6, AAV6.1, AAV6.2, AAV6.1.2, AAV7, AAV7.2, AAV8, AAV9, AAV9.11, AAV9.13, AAV9.16, AAV9.24, AAV9.45, AAV9.47, AAV9.61, AAV9.68, AAV9.84, AAV9.9, AAV10, AAV11, AAV12, AAV16.3, AAV24.1, AAV27.3, AAV42.12, AAV42-1b, AAV42-2, AAV42-3a, AAV42-3b, AAV42-4, AAV42-5a, AAV42-5b, AAV42-6b, AAV42-8, AAV42-10, AAV42-11, AAV42-12, AAV42-13, AAV42-15, AAV42-aa, AAV43-1, AAV43-12, AAV43-20, AAV43-21, AAV43-23, AAV43-25, AAV43-5, AAV44.1, AAV44.2, AAV44.5, AAV223.1, AAV223.2, AAV223.4, AAV223.5, AAV223.6, AAV223.7, AAV1-7/rh.48, AAV1-8/rh.49, AAV2-15/rh.62, AAV2-3/rh.61, AAV2-4/rh.50, AAV2-5/rh.51, AAV3.1/hu.6, AAV3.1/hu.9, AAV3-9/rh.52, AAV3-11/rh.53, AAV4-8/r11.64, AAV4-9/rh.54, AAV4-19/rh.55, AAV5-3/rh.57, AAV5-22/rh.58, AAV7.3/hu.7, AAV16.8/hu.10, AAV16.12/hu.11, AAV29.3/bb.1, AAV29.5/bb.2, AAV106.1/hu.37, AAV114.3/hu.40, AAV127.2/hu.41, AAV127.5/hu.42, AAV128.3/hu.44, AAV130.4/hu.48, AAV145.1/hu.53, AAV145.5/hu.54, AAV145.6/hu.55, AAV161.10/hu.60, AAV161.6/hu.61, AAV33.12/hu.17, AAV33.4/hu.15, AAV33.8/hu.16, AAV52/hu.19, AAV52.1/hu.20, AAV58.2/hu.25, AAVA3.3, AAVA3.4, AAVA3.5, AAVA3.7, AAVC1, AAVC2, AAVC5, AAVF3, AAVF5, AAVH2, AAVrh.72, AAVhu.8, AAVrh.68, AAVrh.70, AAVpi.1, AAVpi.3, AAVpi.2, AAVrh.60, AAVrh.44, AAVrh.65, AAVrh.55, AAVrh.47, AAVrh.69, AAVrh.45, AAVrh.59, AAVhu.12, AAVH6, AAVLK03, AAVH-1/hu.1, AAVH-5/hu.3, AAVLG-10/rh.40, AAVLG-4/rh.38, AAVLG-9/hu.39, AAVN721-8/rh.43, AAVCh.5, AAVCh.5R1, AAVcy.2, AAVcy.3, AAVcy.4, AAVcy.5, AAVCy.5R1, AAVCy.5R2, AAVCy.5R3, AAVCy.5R4, AAVcy.6, AAVhu.1, AAVhu.2, AAVhu.3, AAVhu.4, AAVhu.5, AAVhu.6, AAVhu.7, AAVhu.9, AAVhu.10, AAVhu.11, AAVhu.13, AAVhu.15, AAVhu.16, AAVhu.17, AAVhu.18, AAVhu.20, AAVhu.21, AAVhu.22, AAVhu.23.2, AAVhu.24, AAVhu.25, AAVhu.27, AAVhu.28, AAVhu.29, AAVhu.29R, AAVhu.31, AAVhu.32, AAVhu.34, AAVhu.35, AAVhu.37, AAVhu.39, AAVhu.40, AAVhu.41, AAVhu.42, AAVhu.43, AAVhu.44, AAVhu.44R1, AAVhu.44R2, AAVhu.44R3, AAVhu.45, AAVhu.46, AAVhu.47, AAVhu.48, AAVhu.48R1, AAVhu.48R2, AAVhu.48R3, AAVhu.49, AAVhu.51, AAVhu.52, AAVhu.54, AAVhu.55, AAVhu.56, AAVhu.57, AAVhu.58, AAVhu.60, AAVhu.61, AAVhu.63, AAVhu.64, AAVhu.66, AAVhu. 67, AAVhu.14/9, AAVhu.t19, AAVrh.2, AAVrh.2R, AAVrh.8, AAVrh.8R, AAVrh.12, AAVrh.13, AAVrh.13R, AAVrh.14, AAVrh.17, AAVrh.18, AAVrh.19, AAVrh.20, AAVrh.21, AAVrh.22, AAVrh.23, AAVrh.24, AAVrh.25, AAVrh.31, AAVrh.32, AAVrh.33, AAVrh.34, AAVrh.35, AAVrh.36, AAVrh.37, AAVrh.37R2, AAVrh.38, AAVrh.39, AAVrh.40, AAVrh.46, AAVrh.48, AAVrh.48.1, AAVrh.48.1.2, AAVrh.48.2, AAVrh.49, AAVrh.51, AAVrh.52, AAVrh.53, AAVrh.54, AAVrh.56, AAVrh.57, AAVrh.58, AAVrh.61, AAVrh.64, AAVrh.64R1, AAVrh.64R2, AAVrh.67, AAVrh.73, AAVrh.74, AAVrh8R, AAVrh8R A586R variant, AAVrh8R R533A variant, AAAV, BAAV, caprine AAV, bovine AAV, AAVhE1.1, AAVhEr1.5, AAVhER1.14, AAVhEr1.8, AAVhEr1.16, AAVhEr1.18, AAVhEr1.35, AAVhEr1.7, AAVhEr1.36, AAVhEr2.29, AAVhEr2.4, AAVhEr2.16, AAVhEr2.16, AAVhEr2.30, AAVhEr2.31, AAVhEr2.36, AAVhER1.23, AAVhEr3.1, AAV2.5T, AAV-PAEC, AAV-LK01, AAV-LK02, AAV-LK03, AAV-LK04, AAV-LK05, AAV-LK06, AAV-LK07, AAV-LK08, AAV-LK09, AAV-LK10, AAV-LK11, AAV-LK12, AAV-LK13, AAV-LK14, AAV-LK15, AAV-LK16, AAV-LK17, AAV-LK18, AAV-LK19, AAV-PAEC2, AAV-PAEC4, AAV-PAEC6, AAV-PAEC7, AAV-PAEC8, AAV-PAEC11, AAV-PAEC12, AAV-2-pre-miRNA-101, AAV-8h, AAV-8b, AAV-h, AAV-b, AAV SM 10-2, AAV Shuffle 100-1, AAV Shuffle 100-3, AAV Shuffle 100-7, AAV Shuffle 10-2, AAV Shuffle 10-6, AAV Shuffle 10-8, AAV Shuffle 100-2, AAV SM 10-1, AAV SM 10-8, AAV SM 100-3, AAV SM 100-10, B P61 AAV, B P62 AAV, B P63 AAV, AAVrh.50, AAVrh.43, AAVrh.62, AAVrh.48, AAVhu.19, AAVhu.11, AAVhu.53, AAV4-8/rh.64, AAVLG-9/hu.39, AAV54.5/hu.23, AAV54.2/hu.22, AAV54.7/hu.24, AAV54.1/hu.21, AAV54.4R/hu.27, AAV46.2/hu.28, AAV46.6/hu.29, AAV128.1/hu.43, true type AAV (ttAAV), UPENN AAV 10, and Japanese AAV 10 serotypes but are not limited thereto.

In some aspects, the serotype of the adeno-associated virus is AAV1, AAV2, AAV3, AAV4, AAV5, AAV6, AAV7, AAV8, AAV9 or AAVrh10. In some aspects, the serotype of the AAV is AAV2. In some aspects, the serotype of the AAV is AAV5. In some aspects, the serotype of the AAV is AAV8. In some aspects, the serotype of the AAV is AAV9.

III.B. Non-AAV Vectors

A non-AAV vector which comprises the polynucleotides described herein (e.g., comprising a transgene and an untranslated nucleic acid sequence) is also provided herein.

In some aspects, the vector can be a plasmid, cosmid, yeast artificial chromosome (YAC), bacteriophage or eukaryotic viral DNA. In addition to AAV vectors described above, other numerous vector backbones known in the art as useful for expressing protein can be employed. Such vectors include, but are not limited to: an adenoviral vector, retroviral vector, poxvirus vector, a baculovirus vector, a herpes viral vector, simian virus 40 (SV40), cytomegalovirus (CMV), mouse mammary tumor virus (MMTV), and Moloney murine leukemia virus. Further, one class of vectors comprises DNA elements derived from viruses such as bovine papilloma virus, polyoma virus, baculovirus, retroviruses, or Semliki Forest virus. Such vectors can be obtained commercially or assembled from the sequences described by methods well-known in the art.

It will be apparent to those skilled in the art that certain disclosures relating to AAV vectors described herein are equally applicable to non-AAV vectors. Accordingly, unless indicated otherwise, the term vector comprises both AAV and non-AAV vectors.

IV. Cells

In some aspects, provided herein are cells comprising any of the polynucleotides described herein (e.g., comprising an untranslated nucleic acid sequence). For instance, in some aspects, cells described herein are transduced, transfected, or transformed with a recombinant expression construct comprising a transgene and an untranslated nucleic acid sequence for transgene expression.

Not to be bound by any one theory, in some aspects, the cells described herein (e.g., transduced with a polynucleotide comprising an untranslated nucleic acid sequence) are useful for producing a protein, such as that encoded by a transgene described herein (e.g., a VEGF inhibitor). As described herein, in some aspects, an untranslated nucleic acid sequence described herein (i.e., EF-1α intron fragment) can enhance the expression of the protein encoded by the transgene ("encoded protein") in a cell. Accordingly, in some aspects, a cell described herein (e.g., transduced with a polynucleotide comprising a transgene and an untranslated nucleic acid sequence of the present disclosure) produces greater expression of the encoded protein compared to a reference cell. In some aspects, the reference cell is transduced with a corresponding polynucleotide but lacking the untranslated nucleic acid sequence.

In some aspects, the cells described herein can produce the protein encoded by the transgene in vitro. In certain aspects, the cells described herein can produce the encoded protein in vivo (e.g., in a subject that received an administration of a polynucleotide described herein). In some aspects, the cells described herein can produce the encoded protein both in vitro and in vivo.

In some aspects, a cell that can be used to produce a protein encoded by a transgene (e.g., in vitro) comprises a host cell. As used herein, the term "host cell" is intended to include cells of any organism that can be transduced with the expression construct (e.g., vector) to replicate the expression construct or express the gene encoded by the expression construct. Such cells include eukaryotic cells and prokaryotic cells. As used herein, the term "transduction" is intended to include "transfection" and "transformation". The host cell can be transduced, transfected or transformed with the expression construct. This process means the delivery or introduction of the exogenous nucleic acid molecule into the host cell.

In some aspects, the host cell is a eukaryotic cell. In some aspects, the host cell is selected from the group consisting of a mammalian cell, an insect cell, a yeast cell, a transgenic mammalian cell, and a plant cell. In some aspects, the host cell is a prokaryotic cell. In some aspects, the prokaryotic cell is a bacterial cell.

In some aspects, the host cell is an insect cell. In some aspects, the insect cell is Sf9. In some aspects, the host cell is a mammalian cell. Non-limiting examples of mammalian cells that can be used with the present disclosure include HEK293, HeLa, ARPE-19, RPE-1, HepG2, Hep3B, Huh-7, C8D1a, Neuro2A, CHO, MES13, BHK-21, COST, COP5, A549, MCF-7, HC70, HCC1428, BT-549, PC3, LNCaP, Capan-1, Panc-1, MIA PaCa-2, SW480, HCT166, LoVo, A172, MKN-45, MKN-74, Kato-III, NCI-N87, HT-144, SK-MEL-2, SH-SY5Y, C6, HT-22, PC-12, NIH3T3 cells, and combinations thereof.

In some aspects, a cell that can be used to produce a protein encoded by a transgene described herein (e.g., in vivo) comprises a human cell. In some aspects, the human cell is a cell of a subject that is to receive an administration of a nucleic acid molecule described herein. In certain aspects, the human cell is from a donor (e.g., healthy human subject).

V. Pharmaceutical Compositions

The various nucleic acid molecules, cells, and vectors disclosed herein (also referred to herein as "active compounds") can be incorporated into pharmaceutical compositions suitable for administration. Accordingly, in some aspects, the present disclosure is directed to such a pharmaceutical composition.

In some aspects, disclosed herein is a pharmaceutical composition comprising (a) any of the polynucleotides described herein (e.g., comprising a transgene and an untranslated nucleic acid sequence) and (b) one or more pharmaceutically acceptable carriers. In some aspects, disclosed herein is a pharmaceutical composition comprising (a) a vector (e.g., rAAV) as described herein and (b) one or more pharmaceutically acceptable carriers. In some aspects, disclosed herein is a pharmaceutical composition comprising (a) a cell as described herein and (b) one or more pharmaceutically acceptable carriers.

In some aspects, a pharmaceutical composition described herein comprises a recombinant adeno-associated virus and a pharmaceutically acceptable carrier, wherein the recombinant adeno-associated virus comprises (a) an AAV type 8 capsid protein and (b) a polynucleotide comprising (i) a transgene, which comprises the nucleotide sequence set forth in SEQ ID NO: 23, and (ii) a control element operably linked to the transgene, wherein the control element comprises (from 5' to 3'): (1) the CMV enhancer sequence set forth in SEQ ID NO: 4; (2) the chicken β-actin promoter sequence set forth in SEQ ID NO: 8; (3) the chicken β-actin exon 1 (E1) sequence set forth in SEQ ID NO: 15; (4) the splicing donor sequence of the chicken β-actin intron set forth in SEQ ID NO: 10; (5) an untranslated nucleic acid sequence comprising, consisting essentially of, or consisting of the nucleotide sequence set forth in SEQ ID NO: 2]], SEQ ID NO: 3, or SEQ ID NO: 57; and (6) the EF-1α exon 2 (E2) sequence set forth in SEQ ID NO: 11.

The pharmaceutically acceptable carriers that can be used with the present disclosure are those that are commonly used for formulation. Examples of the pharmaceutically acceptable carriers include, but are not limited to, lactose, dextrose, sucrose, sorbitol, mannitol, starch, gum acacia, calcium phosphate, alginate, gelatin, calcium silicate, microcrystalline cellulose, polyvinylpyrrolidone, cellulose, water, syrup, methyl cellulose, methyl hydroxybenzoate, propyl hydroxybenzoate, talc, magnesium stearate, and mineral oil. The pharmaceutical composition of the present disclosure can further include one or more additives selected from the group consisting of lubricating agents, wetting agents, sweetening agents, flavoring agents, emulsifying agents, suspending agents, and preservatives. Details of suitable pharmaceutically acceptable carriers and formulations can be found in Remington's Pharmaceutical Sciences (19th ed., 1995).

A pharmaceutical composition of the disclosure is formulated to be compatible with its intended route of administration. Examples of suitable parenteral routes of administration include intravenous injection, transdermal administration, subcutaneous injection, intramuscular injection, intravitreal injection, subretinal injection, suprachoroidal injection, eye drop administration, intracerebroventricular injection, intrathecal injection, intraamniotic injection, intraarterial injection, intraarticular injection, intracardiac injection, intracavernous injection, intracerebral injection, intracisternal injection, intracoronary injection, intracranial injection, intradural injection, epidural injection, intrahippocampal injection, intranasal injection, intraosseous injection, intraperitoneal injection, intrapleural injection, intraspinal injection, intrathoracic injection, intrathymic injection, intrauterine injection, intravaginal injection, intraventricular injection, intravesical injection, subconjunctival injection, intratumoral injection, local injection, intraperitoneal injection, and combinations thereof.

In some aspects, the pharmaceutical composition is administered in a daily dose of 0.0001 to 100 mg/kg.

The pharmaceutical composition of the present disclosure can be formulated with one or more pharmaceutically acceptable carriers and/or excipients. The pharmaceutical composition can be provided in unit dosage forms or dispensed in multi-dose containers. The formulation can be in the form of a solution, suspension or emulsion in an oil or aqueous medium or can be in the form of an extract, powder, granule, tablet or capsule. The formulation can further include a dispersant or a stabilizer.

VI. Kits

Also disclosed herein are kits comprising one or more polynucleotides as disclosed herein (e.g., comprising a transgene and an untranslated nucleic acid sequence), one or more vectors (e.g., rAAV) as disclosed herein, one or more cells as disclosed herein, any pharmaceutical composition as disclosed herein, or any combination thereof. In some aspects, the kit also comprises instructions for administering any of the aforesaid, or a combination thereof, to a subject in need thereof.

The terms "kit" and "system," as used herein, are intended to refer to at least one or more polynucleotides as disclosed herein, one or more vectors (e.g., rAAV) as disclosed herein, one or more host cells as disclosed herein, any pharmaceutical composition as disclosed herein, or any combination thereof, which, in some aspects, are in combination with one or more other types of elements or components (e.g., other types of biochemical reagents, containers, packages, such as packaging intended for commercial sale, instructions of use, and the like).

VII. Uses and Methods

VII.A. Methods of Producing

Also disclosed herein are methods of producing a polypeptide encoded by a transgene. In some aspects, such a method comprises culturing a cell described herein (e.g., transduced with a polynucleotide comprising a transgene and an untranslated nucleic acid molecule) under suitable conditions and recovering the encoded protein. In certain aspects, a method of producing a polypeptide encoding by a transgene comprises administering a polynucleotide of the present disclosure (e.g., comprising a transgene and an untranslated nucleic acid molecule) to a subject in need thereof, such that the encoded polypeptide is produced in the subject. Additional disclosure relating to such in vivo method of producing a polypeptide is provided elsewhere in the present disclosure (see, e.g., therapeutic uses).

In some aspects, the present disclosure provides methods of producing a recombinant adeno-associated virus (rAAV), comprising a polynucleotide described herein (e.g., comprising a transgene and an untranslated nucleic acid sequence). In some aspects, a method of producing such a recombinant AAV, comprises culturing a cell that has been transfected with an AAV vector described herein under conditions whereby the recombinant AAV is produced. In some aspects, the method further comprises recovering the recombinant AAV from a supernatant of the cell culture.

In some aspects, the recombinant adeno-associated virus vector can be constructed using (i) an AAV construct comprising the transgene and an untranslated nucleic acid sequence (see, e.g., FIG. 6C), (ii) a construct containing the rep and cap genes, and (iii) a helper construct to transduce a transgene into the host cell. In such aspect, the helper construct can contain the E2A gene that promotes AAV genome replication and gene transcription, the E4 gene that allows AAV mRNA to move from the nucleus to the cytoplasm, and the VA region that produces two VA RNAs serving to regulate translation.

In some aspects, the above-described three constructs can be replaced by two constructs for transduction into the host cell. In such aspects, an AAV construct comprises a transgene and an untranslated nucleic acid sequence, and a separate construct comprises the rep and cap genes, the E2A gene, the E4 gene, and the VA region. Additional methods for producing AAV particles described herein are generally known in the art. See, e.g., Clément et al., *Mol Ther Methods Clin Dev* 3: 16002 (March 2016); Clark, *Kidney Int.* 61: S9-15 (January 2002); and Xiao et al., *J Virol* 72(3): 2224-32 (March 1998); each of which is incorporated herein by reference in its entirety.

VII.B. Therapeutic Uses

The nucleic acid molecules described herein (e.g., comprising a transgene and an untranslated nucleic acid sequence), vectors and recombinant viruses (e.g., rAAV) harboring such nucleic acid molecules, and methods described herein have numerous in vitro and in vivo utilities. For example, the polynucleotides described herein, e.g., a vector, e.g., an AAV vector, can be administered to cells in culture, in vitro or ex vivo, or to human subjects, e.g., in vivo, to treat diseases. Accordingly, in some aspects, the present disclosure provides use of any of the polynucleotides as described herein (e.g., comprising a transgene and an untranslated nucleic acid sequence), the recombinant expression construct as described herein, cells as described herein, pharmaceutical compositions as disclosed herein, or the recombinant virus as described herein for therapeutic applications.

In some aspects, disclosed herein is a method of expressing a transgene in a subject in need thereof, comprising administering to the subject a polynucleotide as disclosed herein (e.g., comprising a transgene and an untranslated nucleic acid sequence), a vector as disclosed herein, a recombinant virus (e.g., rAAV) as disclosed herein, a cell as disclosed herein, or a pharmaceutical composition as disclosed herein, wherein after the administration the expression of the transgene is increased in the subject.

As described herein, the untranslated nucleic acid sequences of the present disclosure can increase the expression of the transgene when the transgene is translated. Accordingly, in some aspects, the present disclosure is directed to a method of increasing the expression of a transgene in a cell, comprising contacting the cell with any of the polynucleotides, vectors, or recombinant viruses (e.g., rAAV) as disclosed herein. The contacting can occur ex vivo or in vivo. When the contacting occurs in vivo, the method can further comprise administering any of the polynucleotides, vectors, or recombinant viruses to the subject prior to the contacting.

In some aspects, after the contacting, the expression of the transgene is increased by at least about 1 fold, at least about 1.1 fold, at least about 1.2 fold, at least about 1.3 fold, at least about 1.4 fold, at least about 1.5 fold, at least about 1.6 fold, at least about 1.7 fold, at least about 1.8 fold, at least about 1.9 fold, at least about 2 fold, at least about 2.5 fold, at least about 3 fold, at least about 3.5 fold, at least about 4 fold, at least about 5 fold, at least about 6 fold, at least about 7 fold, at least about 8 fold, at least about 9 fold, or at least about 10 fold or more, compared to a reference expression. In some aspects, the reference expression is the expression of the transgene in the cell prior to the contacting. In some aspects, the reference expression is the expression of the transgene in a corresponding cell that was not contacted with the polynucleotide, vector, or recombinant virus described herein (e.g., either lack the untranslated nucleic acid sequence or comprises the nucleotide sequence set forth in SEQ ID NO: 1).

Another aspect of the present disclosure provides a method for treating a disease in a subject in need thereof, comprising administering an effective amount of any of the polynucleotides, vectors, cells, recombinant viruses, or pharmaceutical compositions to the subject. As is apparent from the present disclosure, the compositions described herein (e.g., polynucleotides, the recombinant expression constructs, cells, pharmaceutical compositions, or recombinant viruses) can be used to treat any disease of interest, e.g., by modifying the transgene.

Diseases that can be prevented, ameliorated or treated by the present disclosure are not limited and include all diseases that require a reduced number of administrations of the drug. Non-limiting example of such a disease includes ophthalmic diseases. In some aspects, the ophthalmic diseases are selected from a diabetic retinopathy, choroidal neovascularization, macular degeneration, retinal degeneration, macular edema, retinal edema, *Macula tumentia*, or combinations thereof.

In some aspects, an ophthalmic disease that can be treated with the present disclosure comprises a macular degeneration. In some aspects, the macular degeneration comprises age-related macular degeneration (AMD). Age-related macular degeneration can be divided into dry (atrophic) macular degeneration and wet (neovascular or exudative) macular degeneration. Age-related macular degeneration can also be divided into early AMD, intermediate AMD, and late or advanced AMD (geographic atrophy). In some aspects, an ophthalmic disease that can be treated with the present disclosure comprises a diabetic retinopathy. In some aspects, diabetic retinopathy is non-proliferative diabetic retinopathy (NPDR). In some aspects, diabetic retinopathy is proliferative diabetic retinopathy (PDR). In some aspects, diabetic retinopathy is diabetic maculopathy. In some aspects, diabetic retinopathy is diabetic macular edema. In some aspects, diabetic retinopathy is any retinopathy associated with an ischemic damage within the retina. Unless indicated otherwise, the present disclosure can be used to treat all forms of AMD and/or diabetic retinopathy.

Another aspect of the present disclosure provides a gene therapeutic agent or a method for treating a disease that can achieve sustained transgene expression.

The use of the viral delivery system described herein enables administration of the composition described herein (e.g., polynucleotides, the recombinant expression constructs, cells, pharmaceutical compositions, or recombinant viruses) at intervals of about 1 week, about 2 weeks, about 3 weeks, about 1 month, about 2 months, about 3 months, about 4 months, about 5 months, about 6 months, about 7 months, about 8 months, about 9 months, about 10 months, about 11 months, or about 1 year or more. In some aspects, the interval is about 2 to about 3 months. In some aspects, the interval is about 6 months. In some aspects, the interval is about 1 year. In some aspects, the interval is at least about 1 year. That is, the use of the viral delivery system described herein leads to a drastic reduction in the frequency of administration of the composition, allowing a doctor, patient, or subject to avoid an uncomfortable feeling caused by repeated administration of the composition. Depending on patient's symptoms or needs, the composition can be initially administered at least 2 or 3 times, at intervals of 1 to 2 weeks and then once every 2 to 3 months, every 6 months or every year or more.

The present disclosure will be more specifically explained with reference to the following examples. It will be evident to those skilled in the art that the scope of the present disclosure is not limited by these examples according to the gist of the present disclosure.

EXAMPLES

Materials and Methods

Example 1. Preparation of pAAV-eGFP Construct Including No Enhancer-Promoter-Intron Sequences Example 1-1. Insertion of bGH Polyadenylation Signal Sequence Polymerase chain reaction (PCR) was performed using a pcDNA5/FRT/TO construct (Invitrogen, USA, Cat No. V6520-20) as a template and oligo #001 and #002 to obtain a bovine growth hormone (bGH) polyadenylation signal A sequence (poly A) fragment. Next, human growth hormone (hGH) poly A was removed and bGH poly A was inserted using the BglII/BstEII sites of a pAAV-MCS-promoterless plasmid (Cellbiolabs, USA, Cat No. VPK-411).

Example 1-2. Insertion of eGFP

Human codon optimized eGFP was derived from a pUCIDT-KAN-eGFP construct (GeneArt, Germany) and cloned into the BamHI/HindIII sites of the pAAV-bGH construct prepared in Example 1-1.

Example 1-3. Insertion of WPRE Sequence

A woodchuck hepatitis virus posttranscriptional regulatory element sequence was obtained from a pUC57-WPRE construct (GenScript, USA) and cloned into the HindIII/BglII sites of the pAAV-eGFP-bGH construct prepared in Example 1-2.

Example 1-4. Insertion of 4 Copies of miRNA142-3p Target Sequences

Oligo #003 and #004 were annealed and Oligo #005 and #006 were annealed to prepare two DNA fragments, each of which consisted of 2 copies of miRNA142-3p target sequences. The two short DNA fragments were cloned into the HindIII/SalI sites of the pAAV-eGFP-WPRE-bGH construct prepared in Example 1-3 such that a total of 4 copies of the miRNA142-3p target sequences were inserted. As a result, a pAAV-eGFP construct Including no enhancer-promoter-intron sequences was prepared (FIG. 1).

Example 2. Preparation of Constructs Including Various Types of Enhancer-Promoter-Intron Sequences

Example 2-1. Preparation of Constructs Including CEE Series (CEE-FL, CEE-T2, -T3, -T3, -T3.1, -T3.1.1, -T3.1.2, -T3.2, -T4) and CE Sequences

Example 2-1-1. Preparation of Construct Including CEE-FL (Full Length) Nucleotide Sequence A CEE-FL (CMV enhancer (SEQ ID NO: 4)-31 bp CMV promoter (SEQ ID NO: 5)-EF-1α promoter (SEQ ID NO: 7)-29 bp EF-1α exon 1 (SEQ ID NO: 13)-EF-1α intron (SEQ ID NO: 1)-9 bp EF-1α exon 2 (SEQ ID NO: 11)) DNA fragment was obtained from a pMK-RQ3_PEM construct (GeneArt, Germany) and cloned into the EcoRI/BamHI sites of the construct prepared in Example 1.

Example 2-1-2. Preparation of Construct Including CEE-T2 Nucleotide Sequence PCR was performed using the construct prepared in Example 2-1-1 as a template and oligo #007/008 and oligo #009/010 combinations. The resulting two DNA fragments were ligated with Gibson Assembly® (NEB, USA, Cat No. E2611) to prepare a construct having the CEE-T2 sequence.

Example 2-1-3. Preparation of Construct Including CEE-T3 Nucleotide Sequence PCR was performed using the construct prepared in Example 2-1-1 as a template and oligo #011/008 and oligo #012/010 combinations. The resulting two DNA fragments were ligated with Gibson assembly to prepare a construct having the CEE-T3 sequence.

Example 2-1-4. Preparation of Construct Including CEE-T3.1 Nucleotide Sequence PCR was performed using the construct prepared in Example 2-1-1 as a template and oligo #013/008 and oligo #014/010 combinations. The resulting two DNA fragments were ligated with Gibson assembly to prepare a construct having the CEE-T3.1 sequence.

Example 2-1-5. Preparation of Construct Including CEE-T3.2 Nucleotide Sequence PCR was performed using the construct prepared in Example 2-1-1 as a template and oligo #015/008 and oligo #016/010 combinations. The resulting two DNA fragments were ligated with Gibson assembly to prepare a construct having the CEE-T4 sequence.

Example 2-1-6. Preparation of Construct Including CEE-T4 Nucleotide Sequence PCR was performed using the construct prepared in Example 2-1-1 as a template and oligo #017/008 and oligo #018/010 combinations. The resulting two DNA fragments were ligated with Gibson assembly to prepare a construct having the CEE-T4 sequence.

Example 2-1-7. Preparation of Construct Including CEE-T3.1.1 Nucleotide Sequence The CEE-T3.1.1 nucleotide sequence was obtained from a pUC57-T3.1.1 construct (GenScript, USA) and cloned into the EcoRI/BamHI sites of the construct prepared in Example 2-1-1.

Example 2-1-8. Preparation of Construct Including CEE-T3.1.2 Nucleotide Sequence The CEE-T3.1.2 nucleotide sequence was obtained from a pUC57-T3.1.2 construct (GenScript, USA) and cloned into the EcoRI/BamHI sites of the construct prepared in Example 2-1-1.

Example 2-1-9. Preparation of Construct Including CE Nucleotide Sequence

A CE fragment was obtained from the construct prepared in Example 2-1-1 by PCR using oligo #019 and #020 and cloned into the EcoRI/BamHI sites of the construct prepared in Example 2-1-1.

Example 2-2. Preparation of Construct Including CCE-FL Sequence and Construct Including CC Sequence

Example 2-2-1. Preparation of Construct Including CCE-FL Sequence

A DNA fragment having the CCE-FL sequence (CMV enhancer (SEQ ID NO: 4)-CMV promoter (SEQ ID NO: 6)-30 bp CMV exon 1 (SEQ ID NO: 12)-29 bp EF-1α exon 1 (SEQ ID NO: 13)-EF-1α intron (SEQ ID NO: 1)-9 bp EF-1α exon 2 (SEQ ID NO: 11)) was obtained from a pMK-RQ4_PME construct (GeneArt, Germany). The DNA fragment was cloned into the EcoRI/BamHI sites of the pAAV-eGFP construct prepared in Example 1.

Example 2-2-2. Preparation of Construct Including the CC Sequence

A CC fragment was obtained from the construct prepared in Example 2-2-1 by PCR using oligo #019 and #021 and cloned into the EcoRI/BamHI sites of the construct prepared in Example 2-2-1.

Example 2-3. Preparation of Construct Including CAG-FL Sequence, Construct Including CA-T3.1.1 Sequence, Construct Including CA-T3.1.2 Sequence, and Construct Including CE Sequence

Example 2-3-1. Preparation of Construct Including CEG-FL Sequence

A CAG fragment was obtained from a pCAG-Neo construct (Wako Pure Chemical Industries, Ltd., Japan, Cat No. 163-25601) and cloned into the SnaBI/BamHI sites of the construct prepared in Example 2-1.

Example 2-3-2. Preparation of Construct Including CE Sequence

A CA fragment was obtained from a pUC57-CA construct (GenScript, USA) and cloned into the EcoRI/BamHI sites of the construct prepared from Example 2-3-1.

Example 2-3-3. Preparation of Construct Including CE-T3.1.1 Sequence

A T3.1.1 fragment was obtained from the construct prepared in Example 2-1-7 by PCR using oligo #022 and #023 and cloned into the AfeI/BamHI sites of the construct prepared in Example 2-3-1.

Example 2-3-4. Preparation of Construct Including CE-T3.1.2 Sequence

A T3.1.2 fragment was obtained by annealing oligo #024 and #025 and cloned into the AfeI/BamHI sites of the construct prepared from Example 2-3-1.

Example 2-4. Preparation of Construct Including CEE-FL Sequence, Construct Including CAE-T3.1.1 Sequence and Construct Including CEE-T3.1.2 Sequence

Example 2-4-1. Preparation of Construct Including CEE-FL Sequence

A CAE (CMV enhancer (SEQ ID NO: 4)-chicken β-actin promoter (SEQ ID NO: 8)-32 bp chicken β-actin exon 1 (SEQ ID NO: 14)-29 bp EF-1α exon 1 (SEQ ID NO: 13)-924 bp EF-1α intron (SEQ ID NO: 1)-9 bp EF-1α exon 2 (SEQ ID NO: 11)) fragment was obtained from a pUC57-CAE construct (GenScript, USA) and cloned into the EcoRI/BamHI sites of the construct prepared from Example 1.

Example 2-4-2. Preparation of Construct Including CEE-T3.1.1 Sequence

A CAE-T3.1.1 fragment was obtained from the construct prepared in Example 2-1-7 using oligo #026 and #027 and cloned into the KpnI/BamHI sites of the construct prepared in Example 2-1-7.

Example 2-4-3. Preparation of Construct Including CEE-T3.1.2 Sequence

A CAE-T3.1.2 fragment was obtained from the construct prepared in Example 2-1-8 using oligo #026 and #027 and cloned into the KpnI/BamHI sites of the construct prepared in Example 2-1-8.

Example 2-5. Preparation of pAAV Constructs Including Aflibercept

An aflibercept DNA fragment was obtained from a pcDNA3.1(+)-IgG-aflibercept construct (Genscript, USA) by PCR using oligo #028 and #029 and cloned into the BamHI/HindIII sites of each of the constructs prepared from Examples 2-3-1, 2-3-3, 2-3-4, 2-4-1, 2-4-2, and 2-4-3.

Example 2-6. Preparation of Animal Cell Expression Constructs Without ITR Sequence

Example 2-6-1. Preparation of pcDNA3.1(+)-eGFP Construct

The construct prepared in Example 1 was cut with BamHI/AfeI to obtain an eGFP fragment, which was then cloned into the BamHI/EcoRV sites of the pcDNA3.1(+) construct.

Example 2-6-2. Preparation of Animal Cell Expression Construct Including CEE-FL Sequence The construct prepared in Example 2-1-1 was cut with NdeI/BamHI to obtain a CEE fragment, which was then cloned into the NdeI/BamHI sites of the construct prepared in Example 2-6-1.

Example 2-6-3. Preparation of Animal Cell Expression Construct Including CE Sequence The construct prepared in Example 2-1-9 was cut with NdeI/BamHI to obtain a CE fragment, which was then cloned into the NdeI/BamHI sites of the construct prepared in Example 2-6-1.

Example 2-6-4. Preparation of Animal Cell Expression Construct Including CCE-FL Sequence The construct prepared in Example 2-2-1 was cut with NdeI/BamHI to obtain a CCE fragment, which was then cloned into the NdeI/BamHI sites of the construct prepared in Example 2-6-1.

Example 2-6-5. Preparation of Animal Cell Expression Construct Including CC Sequence The construct prepared from Example 2-2-2 was cut with NdeI/BamHI to obtain a CC fragment, which was then cloned into the NdeI/BamHI sites of the construct prepared in Example 2-6-1.

Example 2-6-6. Preparation of Animal Cell Expression Construct Including CEE-FL Sequence The construct prepared from Example 2-4-1 was cut with NdeI/BamHI to obtain a CAE fragment, which was then cloned into the NdeI/BamHI sites of the construct prepared in Example 2-6-1.

Example 2-6-7. Preparation of Animal Cell Expression Construct Including CE Sequence The construct prepared from Example 2-3-2 was cut with NdeI/BamHI to obtain a CA fragment, which was then cloned into the NdeI/BamHI sites of the construct prepared in Example 2-6-1.

Example 2-7. Sequencing

The nucleotide sequences of all constructs obtained by cloning were verified by DNA sequencing (Macrogen, Korea or Bionics, Korea).

Example 3. Cell Culture

HEK293 and HeLa cell lines were cultured in MEM media (Gibco, USA, Cat No. 42360-032) under humidified conditions at 5% $CO_2$ and 37° C., ARPE-19 cell line was cultured in DMERM/F12 medium (Gibco, USA, Cat No. 11330-032) under humidified conditions at 5% $CO_2$ and 37° C., and RPE-1 and Hep3B cell lines were cultured in DMEM media (Gibco, USA, Cat. No. 10569-010) under humidified conditions at 5% $CO_2$ and 37° C. All media had been supplemented with 10% fetal bovine serum (FBS, Gibco, USA, Cat No. 16000-044) and 1% penicillin-streptomycin (Gioco, USA, Cat No. 15140-163). Expi293 cell line was cultured in Expi293 medium (Gibco, USA, Cat. No. A14351-01) supplemented with 1% penicillin-streptomycin with shaking (250 rpm) under humidified conditions at 8% $CO_2$ and 37° C.

Example 4. Transduction

Example 4-1. Transduction of Adherent Cells

Each of the cell lines was washed twice with DPBS (Gibco, USA, Cat No. 14190-250), detached from the culture dish by treatment with trypsin-EDTA (Gibco, USA, Cat No. 25200-114), and seeded in a 12-well plate to a confluency of 80%. After 24-h culture, lipofectamine 3000 (Thermo Fisher Scientific, USA, Cat No. L300075) was used to transduce plasmid DNA into the cells.

Example 4-2. Transduction of Suspension Cells for AAV Production

For AAV production, $6 \times 10^8$ cells were seeded in 220 ml of expi293 medium in a 1 L Erlenmeyer culture flask. After ~3-4 h culture for stabilization, pHelper plasmid DNA, pUC-RC2 plasmid DNA, pUC-RC2 plasmid DNA or pUC-RC8 plasmid DNA, and transgene-containing AAV construct plasmid DNA (each 3.73 pmoles) were dissolved in 10 ml of Opti-MEM (Gibco, USA, Cat No. 51985-034). Immediately after polyethylenimine (PEI, Polyscience, USA, Cat No. 23966-1) was diluted with 10 ml of Opti-MEM, the two solutions were mixed to prepare a transduction solution. The PEI was used in an amount corresponding to twice the total amount of DNA. After incubation at room temperature for 30 min, a total of 20 ml of the transduction solution was added to the culture flask.

Example 5. Purification of AAV

Example 5-1. Purification of AAV2

72 h after transduction (Example 4-2), the cell culture solution was harvested, followed by centrifugation to remove the medium. The precipitated cells were washed with DPBS and resuspended with 16 ml of DPBS. The cells were lysed by three cycles of freezing/thawing and centrifuged to obtain an AAV2-containing supernatant. The supernatant was mixed with AAVanced™ concentration reagent (System Bioscience, USA, Cat No. AAV110A-1) in a ratio of 4:1 at 4° C. for 16 h, followed by centrifugation. The supernatant was discarded and the AAV2-containing precipitate was washed with 500 µl of Opti-MEM. After complete removal of the supernatant, the precipitate was resuspended in 400 µl of ice-cold DPBS to obtain AAV.

Example 5-2. Purification of AAV8

72 h after transduction (Example 4-2), the cell culture solution was harvested, filtered through a 0.45 µm filter to remove cell debris, and subjected to anion exchange and affinity chromatography to obtain AAV.

Example 6. Titer Determination of the AAV

The titer of the AAV2 purified in Example 5 was determined by qPCR (Bio-Rad, USA, CFX96). First, the AAV was treated with DNase I in DNase I reaction buffer (New England Biolab, USA, M0303S) at 37° C. for 1 h. Thereafter, the DNase I-treated sample was treated with proteinase K (Invitrogen, USA, Cat No. AM2548) at 55° C. for 30 min and incubated at 95° C. for 15 min to inactivate the proteinase K. The prepared samples were used as templates for qPCR and the AAV constructs were used to plot a standard curve ($7.4 \times 10^8$-$7.4 \times 10^4$, 10-fold dilution). A recombinant adeno-associated virus 2 reference standard stock (rAAV2-RSS, ATCC, USA, Cat No. VR-1616) or recombinant adeno-associated virus 8 reference standard stock (rAAV8-RSS, ATCC, USA, Cat No. VR-1816) was used as a positive control. For titer determination, qPCR was performed using 2×SsoAdvanced Universal Probe Supermix (Bio-Rad, USA, Cat No. 172-5282) and AAV2-ITR specific primers (#030, #031) and probe (#032, FAM-CACTCCCTCTCTGCGCGCTCG-BHQ1) (SEQ ID NO: 55). qPCR was repeated 40 times. Each qPCR cycle consisted of denaturation at 95° C. for 10 min, incubation at 95° C. for 30 sec, and subsequent incubation at 60° C. for 1 min. The standard curve and quantification were analyzed using Bio-Rad CFX Maestro 1.1 software (Bio-Rad, USA).

Example 7. In Vitro Transduction with the AAV2

HEK293 cells were seeded in in a 24-well culture plate at a density of $4 \times 10^5$ cells/well. 24 h after seeding, each well was treated with MG132 (Sigma-Aldrich, USA, Cat No. M7449) at a concentration of 5 µM for 8 h. For transduction, the AAV2 was treated at 25,000 multiplicity of infection (MOI) and cultured for 72 h.

Example 8. In Vivo Transduction with the AAV8

The lower portion of the eye was perforated with a 31 G syringe needle and a needle (10 kit) was inserted into the hole, The insertion was stopped at the point where the tip of the needle reached the eye wall, and then administration was performed. The success of subretinal injection was judged by observing retinal bleb creation on OCT immediately after administration. After 4 weeks, the eye was excised and 200 µl of RIPA solution (Thermo Fisher Scientific, USA, Cat No. 89900) supplemented with Halt™ Protease Inhibitor Cocktail 100× (Thermo Fisher Scientific, USA, Cat No. 78429) was added thereto. The eye was ground into a mash with a tissue grinder (Axygen, cat #14-222-358). After incubation at 4° C. for 1 h, the mash was centrifuged at 13,000 g and 4° C. for 15 min. The supernatant was collected and analyzed.

Example 9. Measurement of GFP Expression by Flow Cytometry

The expression of eGFP was measured by flow cytometry (Beckman Coulter, USA, CytoFlex). The measured value for eGFP was calculated by correcting the transduction efficiency with measurement of red fluorescence by a co-transduced pCMV-dsRed construct (Clontech, Japan, Cat No. 632416). 72 h after transduction, cells were washed with DPBS and detached with trypsin. Cells were collected by centrifugation at 1500 rpm for 5 min and resuspended in 500 µl of DPBS supplemented with 2% FBS. For flow cytometry, single cell regions were distinguished based on FSC vs. SSC plot. Among them, FL1-A (green) and FL2-A (red) were measured. Calibration was performed with samples transduced with single fluorescent vectors (pEGFP-C1, Clontech, Japan, Cat No. PT3286-1 and pCMV-DsRed-Expression2) and the values were reflected in the measurement results. All flow cytometry results were analyzed using FlowJo software 10.5.3 (Becton Dickinson & Company, USA).

Example 10. Measurement of Aflibercept Expression Level by ELISA

The levels of secretory proteins were quantified by ELISA. 48 h after transduction with AAV, the cell culture solution was obtained and centrifuged at 1500 rpm and 4° C. for 5 min. The supernatant was collected and used as a sample for ELISA. Aflibercept ELISA (Eagle bioscience, USA, Cat No. IG-AA115) was performed according to the manufacturer's protocol. ELISA results were measured with a Multiskan Sky Microplate Spectrophotometer (Thermo Fisher Scientific, USA) and analyzed with Skanit software (Thermo Fisher Scientific, USA). A set of two experiments using cell lines was conducted in duplicate. The animal experiment was conducted once per eye.

Example 11. Statistical Analysis

All experiments using cell lines except ELISA were conducted in triplicate. The results were analyzed using GraphPad Prism software 8.1.1 (GraphPad Software, Inc., USA), comparisons between two groups were performed using Student's t-tests, and comparisons between three groups or more were performed with one-way ANOVA. For animal experiments, statistical differences were determined by the Wilcoxon matched-pairs signed rank test. *p<0.05, p<0.01, *p<0.001.

TABLE 1

Oligonucleotide sequences used in the present disclosure

| Oligo NO | SEQ ID NO | Sequence (5'→3') |
|---|---|---|
| 001 | 24 | GGAAGATCTCTGTGCCTTCTAGTTGCCAGC |
| 002 | 25 | CACGTGGTTACCCCATAGAGCCCACCGCATC |
| 003 | 26 | AGCTTTCCATAAAGTAGGAAACACTACACGATTCCATAAAGTAGGAAACACTACAACGTTC |
| 004 | 27 | TAGTGTTTCCTACTTTATGGAATCGTGTAGTGTTTCCTACTTTATGGA |
| 005 | 28 | CATAAAGTAGGAAACACTACATCACTCCATAAAGTAGGAAACACTACAG |
| 006 | 29 | TCGACTGTAGTGTTTCCTACTTTATGGAGTGATGTAGTGTTTCCTACTTTATGGAACGTTG |
| 007 | 30 | GTGTGTGGTTTGCTGCAGGGAGCTCAAAATG |
| 008 | 31 | CGGTGATGACGGTGAAAACC |
| 009 | 32 | CCCTGCAGCAAACCACACACGGCACTTACC |
| 010 | 33 | GGTTTTCACCGTCATCACCG |
| 011 | 34 | GTGTGTGGTTTCGAGCTTTTGGAGTACGTCG |
| 012 | 35 | AAAAGCTCGAAACCACACACGGCACTTACC |
| 013 | 36 | GTGTGTGGTTGTTAGGCCAGCTTGGCAC |
| 014 | 37 | CTGGCCTAACAACCACACACGGCACTTACC |
| 015 | 38 | GTGTGTGGTTTCATTCTCAAGCCTCAGACAGTG |
| 016 | 39 | TTGAGAATGAAACCACACACGGCACTTACC |

TABLE 1-continued

Oligonucleotide sequences used in the present disclosure

| Oligo NO | SEQ ID NO | Sequence (5'→3') |
|---|---|---|
| 017 | 40 | GTGTGTGGTTTGGTTCAAAGTTTTTTTCTTCCATTTCAGG |
| 018 | 41 | CTTTGAACCAAACCACACACGGCACTTACC |
| 019 | 42 | CCGGAATTCTGACATTGATTATTGACTAGTTATTAATAGTAATCAATTACGG |
| 020 | 43 | CGCGGATCCCTGTGTTCTGGCGGCAAAC |
| 021 | 44 | CGCGGATCCCGGTTCACTAAACGAGCTCTGCTTATATAG |
| 022 | 45 | TGTAATTCTCCTTGGAATTTGCCCTTTTG |
| 023 | 46 | CCCAAGCTTGGATCCTCACGACACCTGAAATG |
| 024 | 47 | CCTTTTTGAGTTTGGATCTTGGTTCATTCTCAAGCCTCAGACAGTGGTTCAAAGTTTTTTTCTTCCATTTCAGGTGTCGTGAGGATCCA |
| 025 | 48 | AGCTTGGATCCTCACGACACCTGAAATGGAAGAAAAAAACTTTGAACCACTGTCTGAGGCTTGAGAATGAACCAAGATCCAAACTCAAAAAGG |
| 026 | 49 | CGGGGTACCTTCGCAACGGGTTTGCCG |
| 027 | 50 | CGCGGATCCTCACGACACCTG |
| 028 | 51 | TGAGGATCCGCCACCATGGAGTTTGG |
| 029 | 52 | CGCAAGCTTCAGTAGCGCTTTAGCCAGGAGACAAGCTCAGAGACTTCTG |
| 030 | 53 | GGAACCCCTAGTGATGGAGTT |
| 031 | 54 | CGGCCTCAGTGAGCGA |
| 032 | 55 | FAM-CACTCCCTCTCTGCGCGCTCG-BHQ1 |

Experiment Results

1. Increased eGFP Expression by EF-1α Intron in Combination with EF-1α Promoter

Figure 2A:
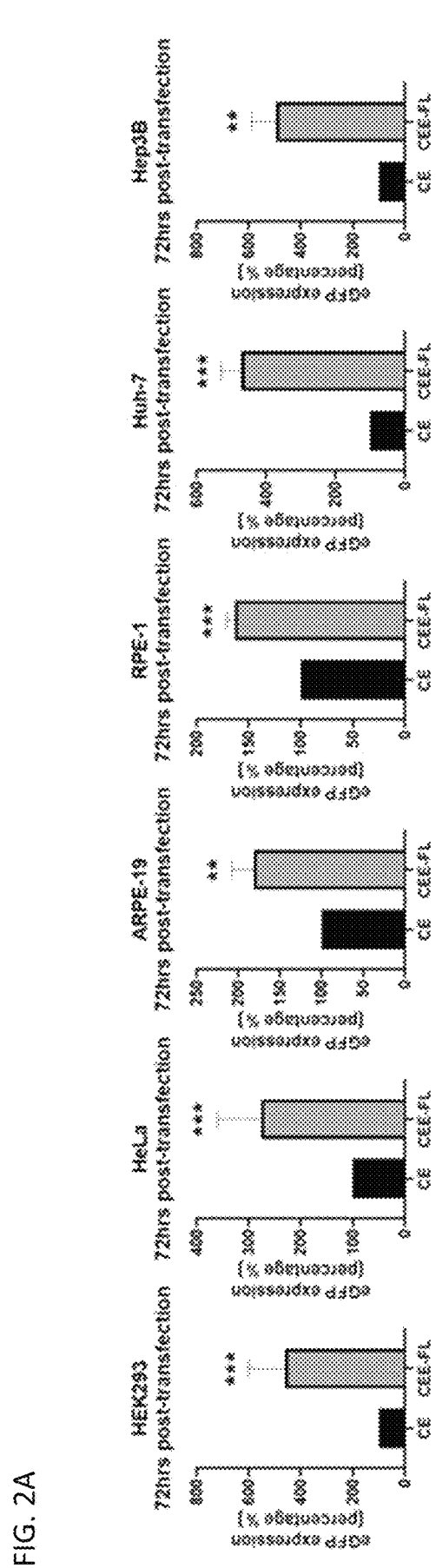
FIGS. 2A and 2B show increases in the expression of eGFP in cells transduced with expression constructs comprising the full-length EF-1α intron in combination with an EF-1α promoter ("CEE-FL"). Control cells were transduced with the corresponding expression constructs that lacked an EF-1α intron ("CE").
Figure 2B:
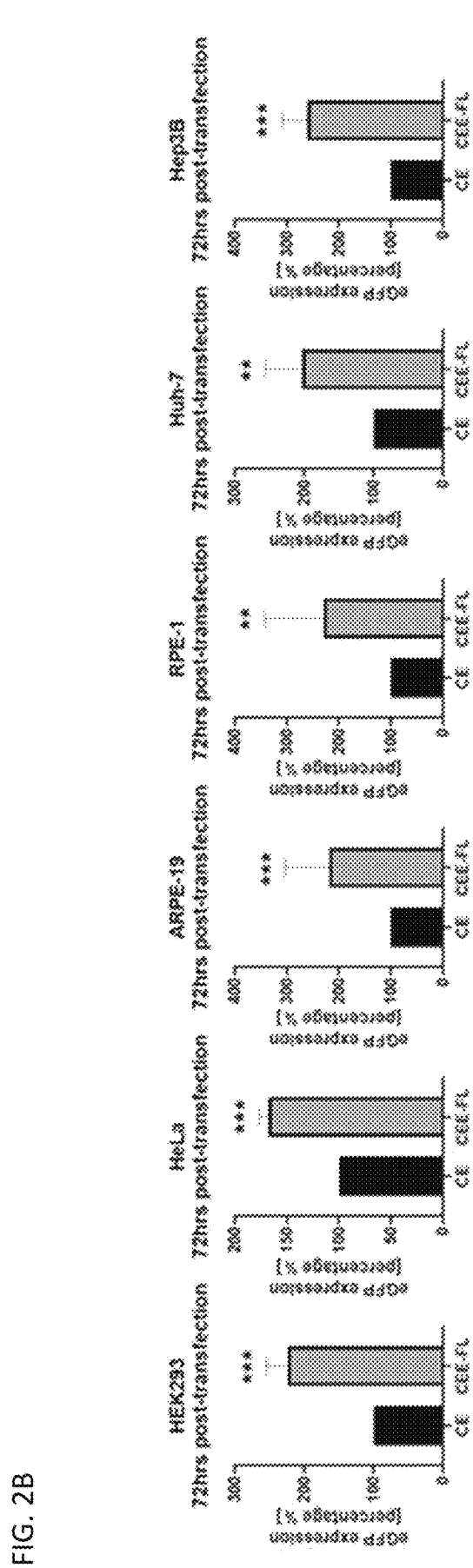

An experiment was conducted to test the influence of human elongation factor-1 alpha (EF-1α) intron on eGFP expression regulated by a combination of a cytomegalovirus (CMV) enhancer and an EF-1α promoter. First, a comparison was performed in the ITR-lacking animal cell expression constructs. As a result, the expression levels of eGFP in all cell lines used (HEK293, HeLa, ARPE-19, RPE-1, Huh-7, and Hep3B) were found to be increased (459.6%, 276.3%, 181.8%, 163.4%, 471.1%, and 494.3%) by EF-1α intron (FIG. 2A). The expression levels of eGFP in the ITR-containing pAAV constructs were found to be increased (224.0%, 167.7%, 218.7%, 229.5%, 202.5%, and 260.5%) by EF-1α intron (FIG. 2B). These results suggest that the combination of EF-1α intron with an EF-1α promoter can increase gene expression in various transgene expression constructs.

Figure 3A:
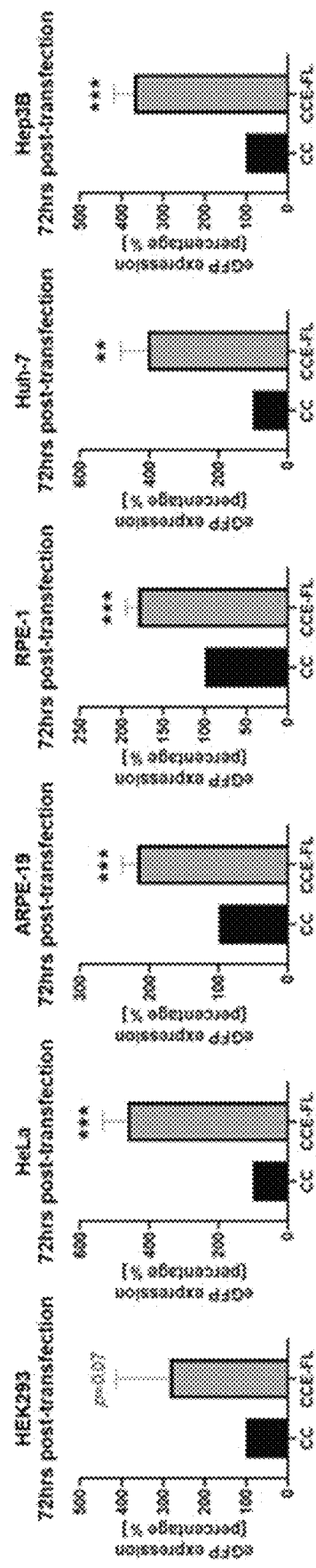
FIGS. 3A, 3B, and 3C show the expression of eGFP in cells transduced with expression constructs comprising the full-length EF-1α intron in combination with various promoters ("CCE-FL"). Control cells were transduced with the corresponding expression constructs but lacking the EF-1α intron.

2. Increased eGFP Expression by EF-1α Intron in Combination with Various Promoters A test was conducted to observe whether EF-1α intron increased gene expression when combined with promoters other than EF-1α promoters. Specifically, a test was conducted to determine the influence of EF-1α intron on the expression of eGFP induced by a combination of a cytomegalovirus (CMV) enhancer and a CMV promoter. First, a comparison was performed in the ITR-lacking animal cell expression constructs. As a result, the expression levels of eGFP in all cell lines used (HEK293, HeLa, ARPE-19, RPE-1, Huh-7, and Hep3B) were found to be increased (284.3%, 464.0%, 217.5%, 180.4%, 405.7%, and 370.6%) by EF-1α intron (FIG. 3A).

Figure 3B:
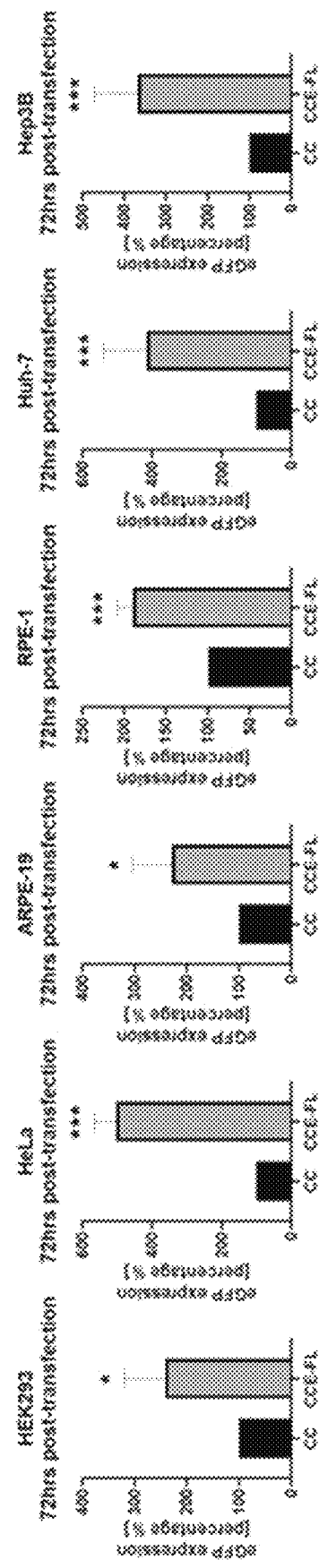

Similarly, EF-1α intron increased the expression of eGFP regulated by a combination of a cytomegalovirus (CMV) enhancer and an EF-1α promoter in the ITR-containing pAAV constructs (241.4%, 494.8%, 266.8%, 185.5%, 415.5%, and 367.8%) (FIG. 3B).

Figure 3C:
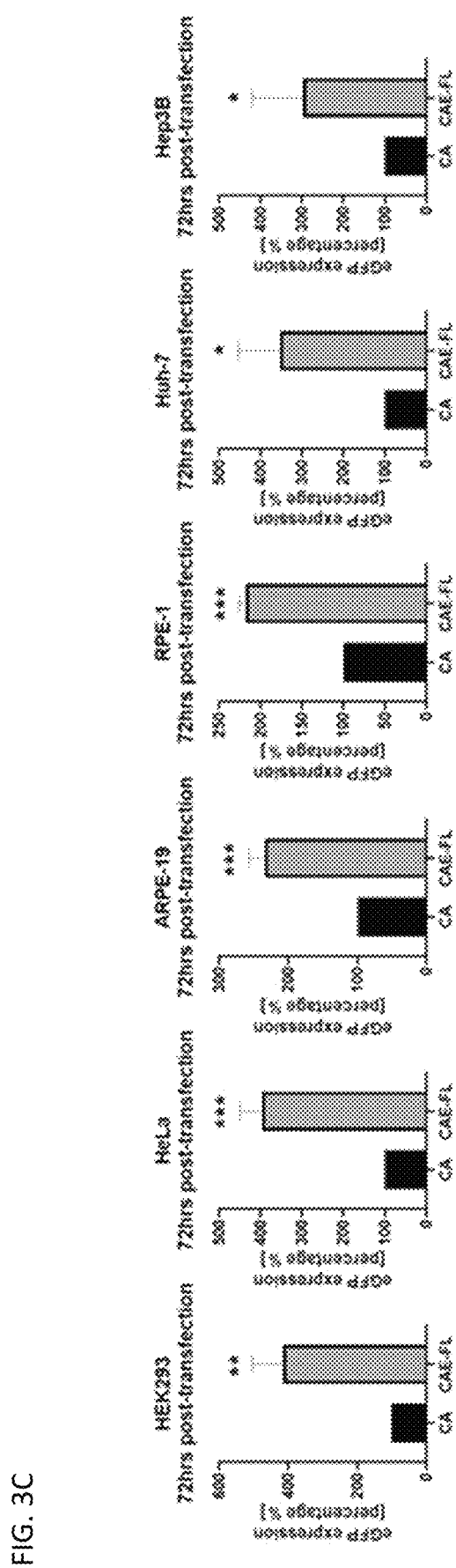

Next, the influence of EF-1α intron on the expression of eGFP regulated by a combination of a CMV enhancer and a chicken β-actin promoter was determined. A comparison was performed in the animal cell expression constructs. As a result, the expression levels of eGFP in all cell lines used (HEK293, HeLa, ARPE-19, RPE-1, Huh-7, and Hep3B) were found to be increased (415.2%, 396.7%, 233.9%, 217.9%, 353.7%, and 297.7%) by EF-1α intron (FIG. 3C). These results suggest that EF-1α intron increases gene expression even when combined with promoters other than EF-1α promoters.

Figure 4A:
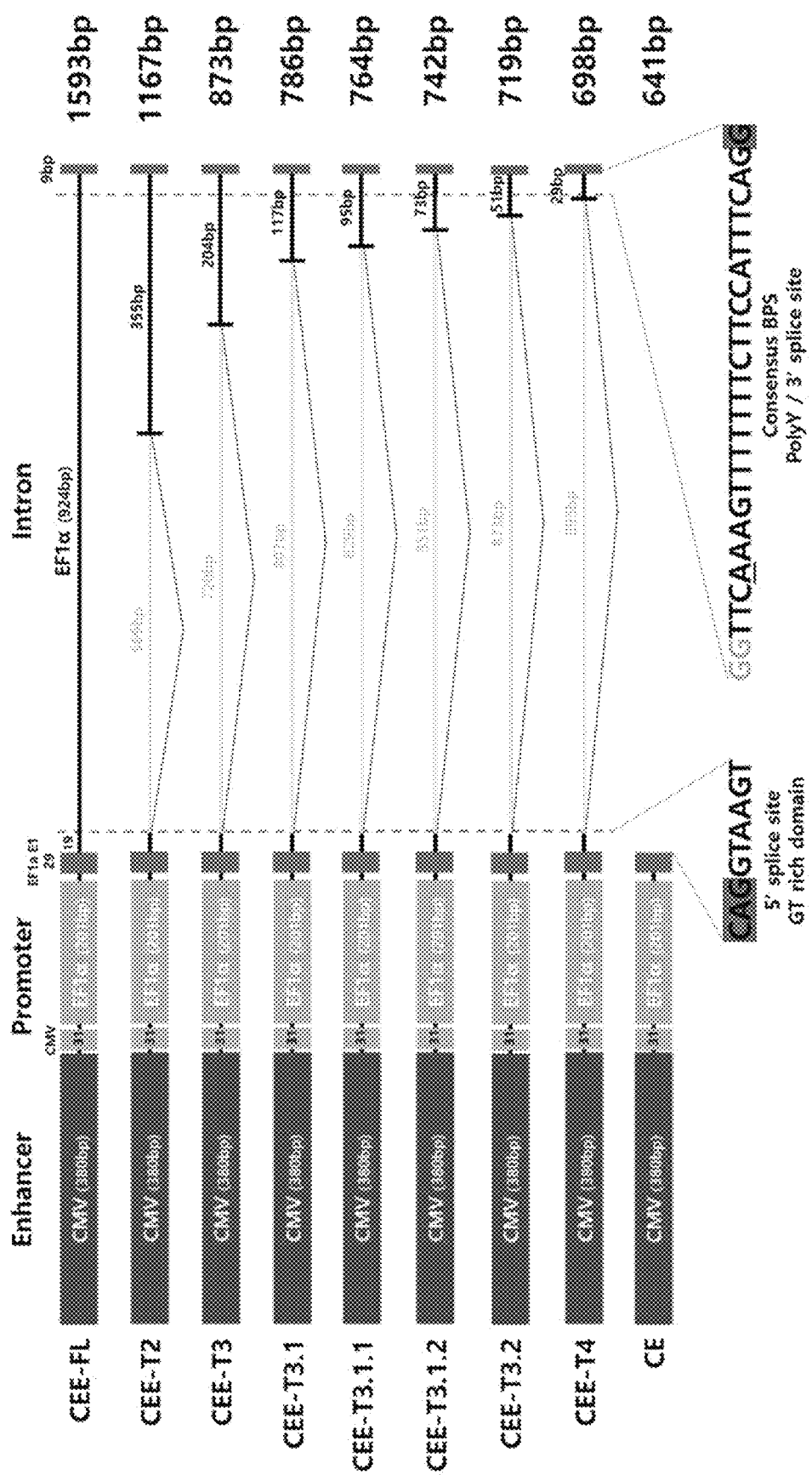
FIGS. 4A and 4B show the increasing or decreasing effect of various EF-1α intron fragment sequences (i.e., untranslated nucleic acid sequences described herein) on gene expression.

3. Determination of the Shortest EF-1α Intron Fragment Showing Increasing Effect on Gene Expression 3-A. Preparation of Series of CEE Constructs in which the Sequence of EF-1α Intron was Sequentially Truncated A CEE-FL construct was designed to include CMV enhancer and CMV promoter portions (31 bp at the 5' end), an EF-1α promoter, 29 bp EF-1α exon 1, 924 bp EF-1α intron, and 9 bp EF-1α exon 2. A splicing donor was located at the 5' end of the core sequence associated with the splicing function of the intron and a splicing acceptor including the branch point site (BPS) was located at the 3' end of the core sequence. To find the shortest EF-1α intron sequence having the ability to increase gene expression, the splicing donor sequence at the 5' end of the intron was conserved and the downstream nucleotides were sequentially truncated. That is, CEE constructs were prepared in which up to 19 bp from the 5' end of EF-1α intron, which are assumed to be the splicing donor consensus sequence of EF-1α intron, were present in common and the downstream 659 bp (T2), 720 bp (T3), 807 bp (T3.1), 829 bp (T3.1.1), 851 bp (T3.1.2), 873 bp (T3.2), and 895 bp (T4) were truncated, as in Example 2-1 (FIG. 4A).

Figure 4B:
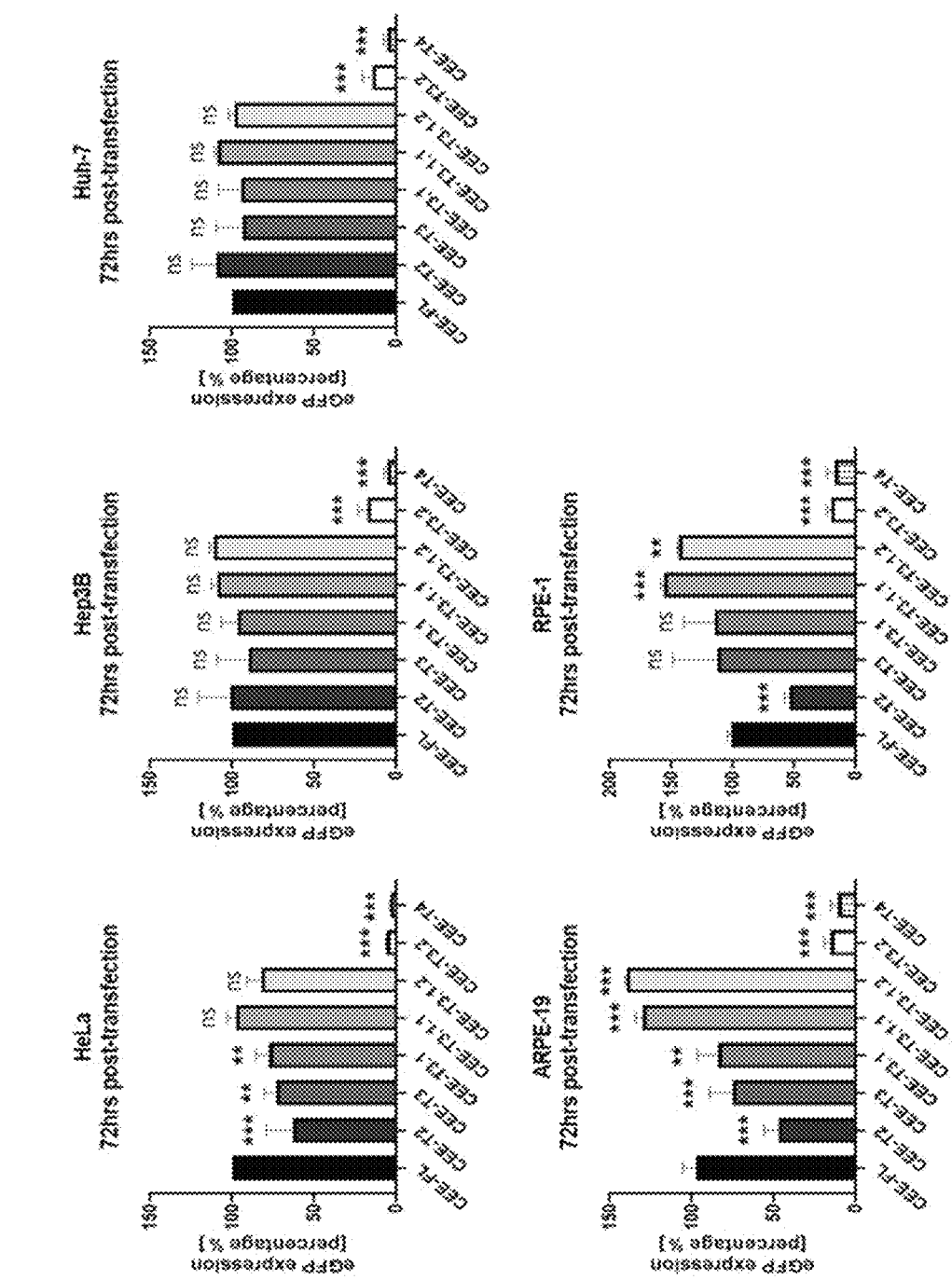

3-B. Increasing or Decreasing Effect of Sequential Truncation of Nucleotides in the EF-1α Intron Sequence on Gene Expression The expressions of eGFP in the eight constructs, i.e. the construct including the full-length EF-1α intron sequence (CEE-FL) and the constructs including sequentially truncated EF-1α intron sequences, were compared in five animal cell lines. First, the expressions of eGFP in the sequentially truncated constructs in HeLa, Hep3B, and Huh-7 cell lines were compared with those of the construct containing the full-length EF-1α intron A. As a result, the eGFP expressions were maintained in CEE-T2 to CEE-T3.1.2 but were drastically decreased in CEE-T3.2 and CEE-T4. In ARPE-19 and RPE-1 cell lines, the eGFP expressions in CEE-T2 were reduced by ~50% compared to those in CEE-FL, but the eGFP expressions in CEE-T3 to CEE-T3.1.2 were similar to or slightly higher than those in CEE-FL. As in the previous cell lines, the gene expressions in CEE-T3.2 and CEE-T4 were drastically decreased. The above results suggest that fragments T2 to T3.1.2 of EF-1α intron A function to increase gene expression and the shortest one of these fragments is T3.1.2 (but is longer than T3.2) (FIG. 4B).

4. Increased Gene Expression by EF-1α Intron Fragments T3.1.1 and T3.1.2

Figure 5A:
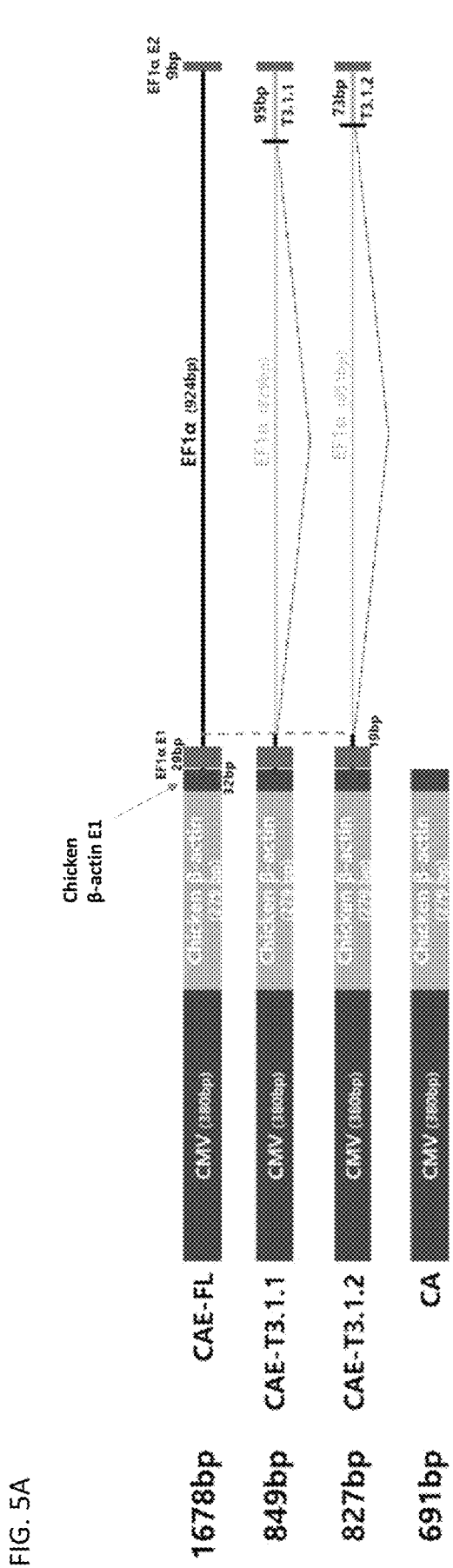
FIGS. 5A, 5B, 5C, and 5D show the abilities of EF-1α intron fragments T3.1.1 (i.e., nucleotides 830 to 924 of SEQ ID NO: 1 (95 base pairs)) and T3.1.2 (i.e., nucleotides 852 to 924 of SEQ ID NO: 1 (73 base pairs)) to increase transgene expression.

4-A. Construction of EF-1α Intron Fragments T3.1.1 and T3.1.2 in Combination with Chicken β-actin Promoter A CAE-FL construct was designed to include a CMV enhancer, a chicken β-actin promoter, 32 bp chicken β-actin exon 1, 29 bp EF-1α exon 1, 924 bp EF-1α intron A, and 9 bp EF-1α exon 2. CA refers to a construct in which all nucleotides of EF-1α intron were truncated. A CAE-T3.1.1 construct was the same as the CAE-FL construct, except that the 19 bp sequence and the T3.1.1 sequence were present at the 5' and 3' ends of EF-1α intron, respectively, and 829 bp between the 5' and 3' ends were truncated in the CAE-T3.1.1 construct. A CAE-T3.1.2 construct was the same as the CAE-FL construct, except that the 19 bp sequence and the T3.1.2 sequence were present at the 5' and 3' ends of EF-1α intron, respectively, and 851 bp between the 5' and 3' ends were truncated in the CAE-T3.1.1 construct (FIG. 5A).

Figure 5B:
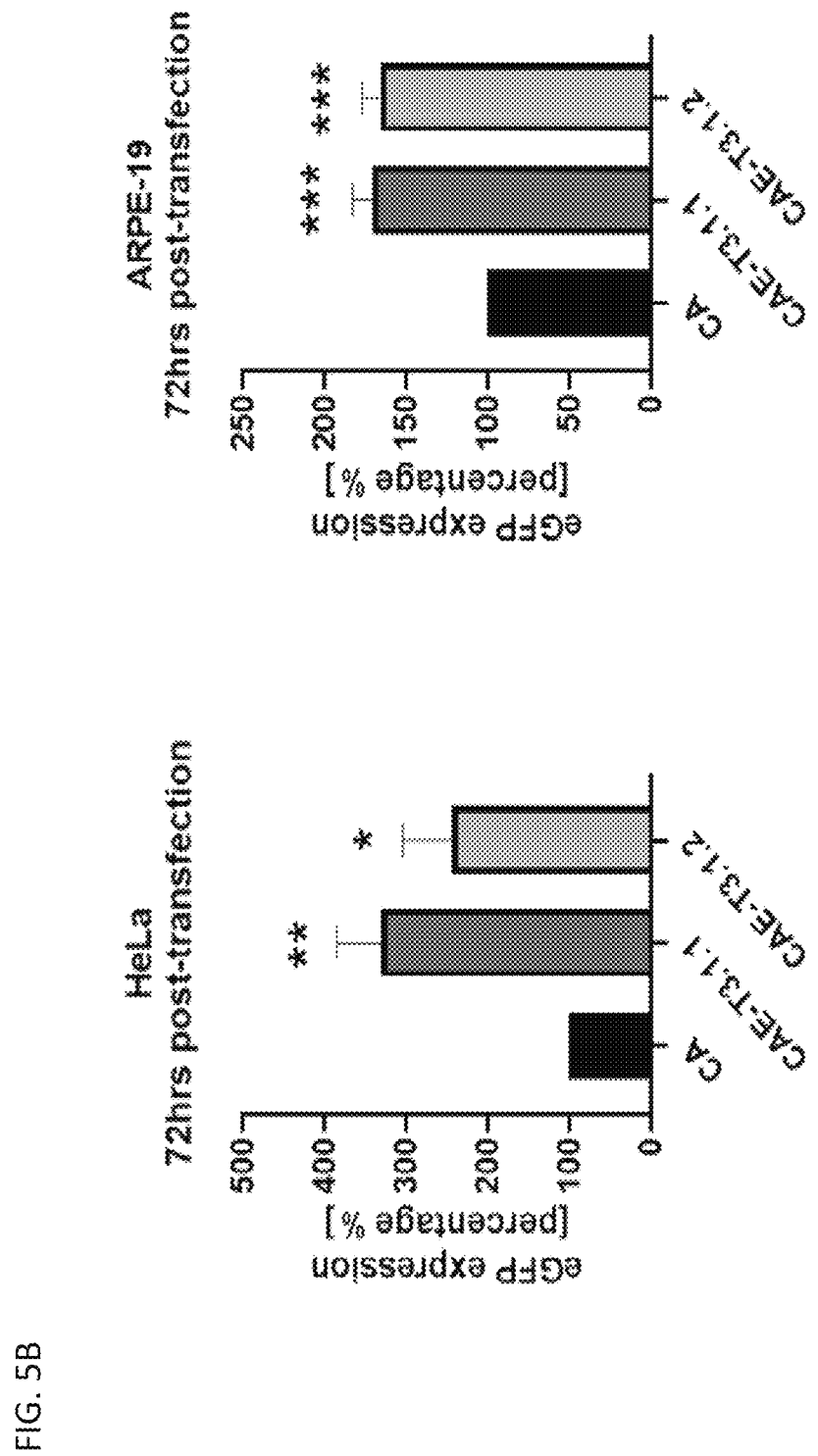

4-B. Increased Gene Expression by EF-1α Intron Fragment T3.1.1 and T3.1.2 in Combination with Chicken β-actin Promoter The expressions of eGFP in CA in which all nucleotides of EF-1α intron were truncated and CAE-T3.1.1 and CAE-T3.1.2 in which the nucleotides of EF-1α intron were partially truncated were compared in two animal cell lines (HeLa, ARPE-19). The eGFP expressions in the CAE-T3.1.1 and CAE-T3.1.2 constructs were increased by 330.5% and 243.9% in HeLa and 170.8% and 165.9% in ARPE-19 compared to those in the CA construct (FIG. 5B). These results suggest that the fragments T3.1.1 and T3.1.2 of EF-1α intron can increase gene expression even when combined with a chicken β-actin promoter.

Figure 5C:
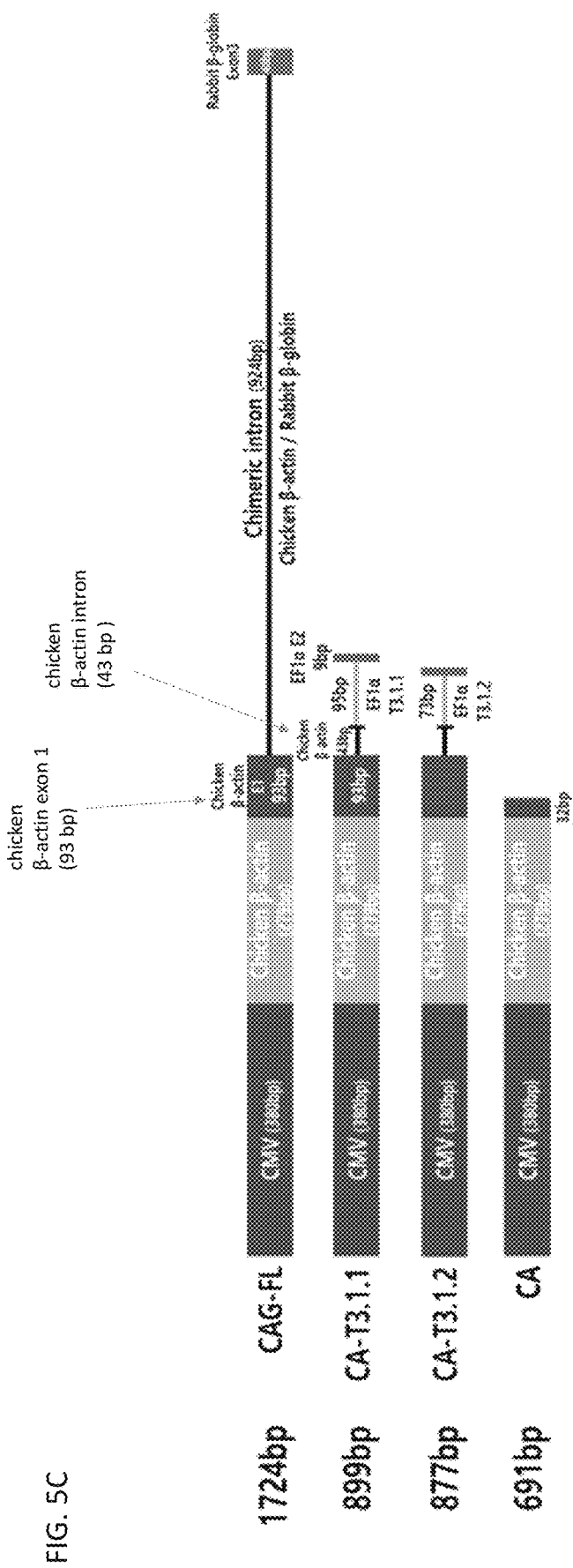

4-C. Preparation of Constructs including EF-1α Intron Fragments T3.1.1 and T3.1.2 in Combination with Splicing Donor of Chicken β-actin CA-T3.1.1 and CA-T3.1.2 constructs were designed to have hybrid intron structures including a 95 bp (T3.1.1) or 73 bp fragment (T3.1.2) at the 3' end of EF-1α intron and 9 bp EF-1α exon 2 in a state in which a CMV enhancer, a chicken β-actin promoter, 93 bp chicken β-actin exon 1, and 43 bp chicken β-actin intron were maintained. Portions of the chicken β-actin exon 1 and the chicken β-actin intron were estimated to serve as splicing donors. The EF-1α intron A fragments were estimated to serve as splicing receptors. A CA construct with no intron sequence was prepared and tested as a control (FIG. 5C).

Figure 5D:
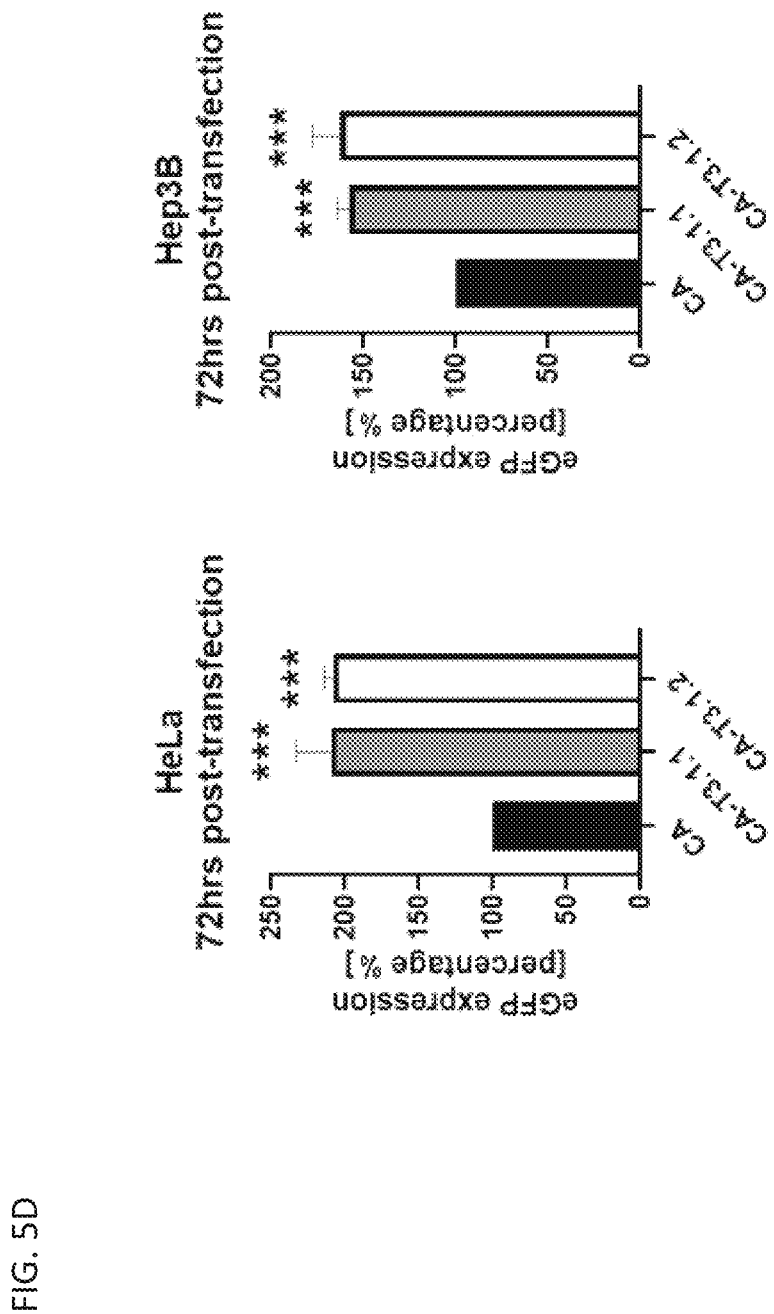

4-D. Increased Gene Expression by Intron Hybridized with Splicing Donor Fragment of Chicken β-actin and Fragments T3.1.1 and T3.1.2 at the 3' end of EF-1α Intron A After transduction of the CA, CA-T3.1.1, and CA-T3.1.2 constructs into HeLa and Hep3B cell lines, gene expression levels were compared. As a result, the gene expressions in CA-T3.1.1 and CA-T3.1.2 were increased (HeLa: 215.7%, 211.0%, Hep3B: 155.0%, 167.5%) compared to those in intron-lacking CA. These results suggest that the EF-1α intron fragments T3.1.1 and T3.1.2 can increase gene expression even when combined with splicing donors of other genes (FIG. 5D).

5. Increased Gene Expression by Fragments T3.1.1 and T3.1.2 in Gene Delivery Using AAV 5-A. Increased Gene Expression by Fragments T3.1.1 and T3.1.2 in In Vitro Gene Delivery Using AAV2

Figure 6A:
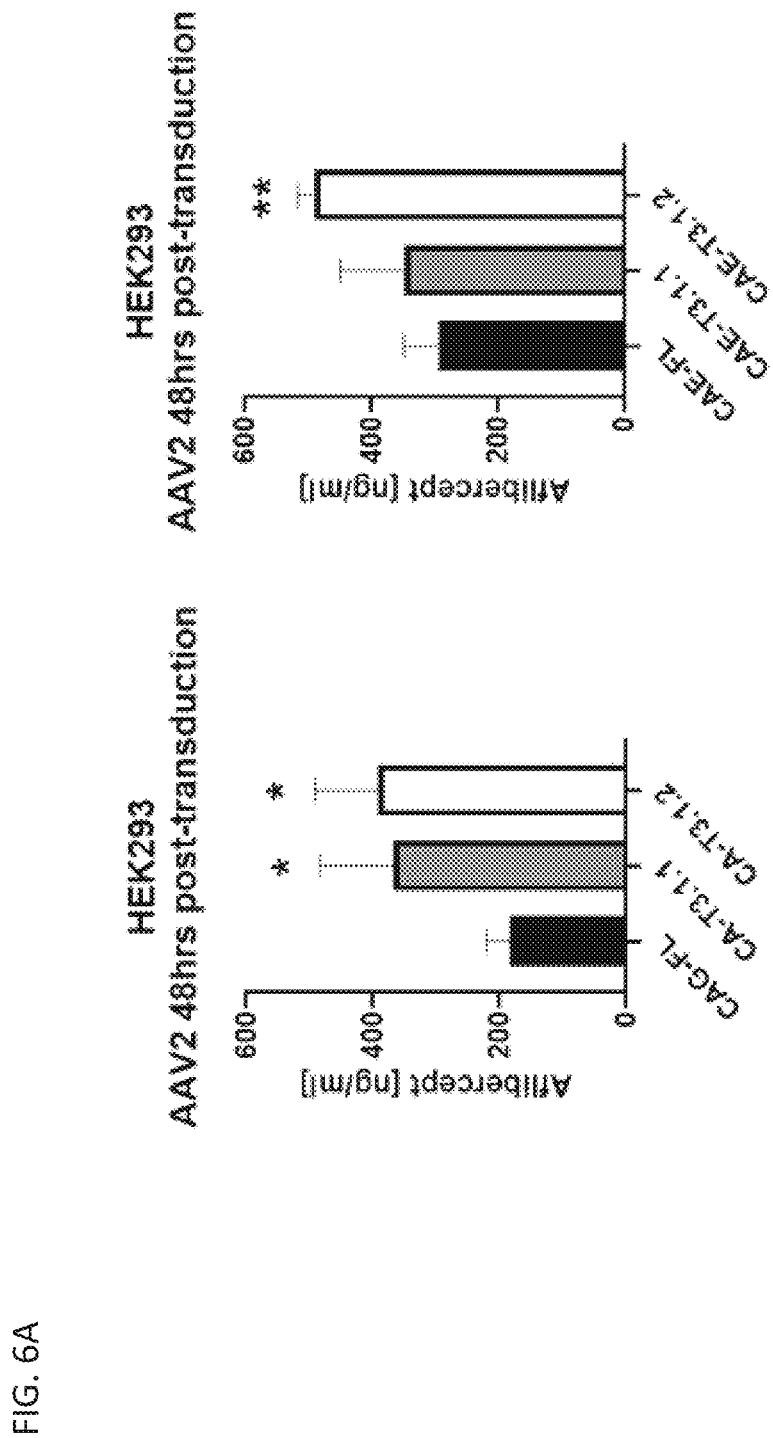
FIGS. 6A, 6B, and 6C show the increasing effects of EF-1α intron fragments T3.1.1 and T3.1.2 on transgene (i.e., aflibercept) expression when AAV was used for gene delivery.

To determine whether the fragments T3.1.1 and T3.1.2 of EF-1α intron had the ability to efficiently induce gene expression when AAV was used for gene delivery, the gene expressions in AAV2 constructs including the fragments CA-T3.1.1, CA-T3.1.2, CAE-T3.1.1, and CAE-T3.1.2 were compared with those in AAV2 constructs including CAG-FL and CAE-FL as regulatory sites for gene expression. The AAV2 constructs were designed to express extracellular secretory aflibercept protein (the nucleotide sequence of SEQ ID NO: 26 encoding a hIgG signal peptide was used as a signal peptide sequence). MG132-treated HEK293 cell line was infected with AAV2 at 25,000 MOI. 48 h after infection, the concentration of aflibercept in the cell culture solution was determined by ELISA. As a result, the expression of aflibercept was increased by 200.1% and 213.1% when infected with CA-T3.1.1 and CA-T3.1.2 as the AAV2 constructs, respectively, compared to when infected with CAG-FL. In addition, the expressions of aflibercept in CAE-T3.1.1 and CAE-T3.1.2 as the AAV2 constructs were increased by 118.2% and 166.5%. respectively, compared to those in CAG-FL (FIG. 6A). The above results suggest that the EF-1α intron A fragments T3.1.1 and T3.1.2 can efficiently increase gene expression when AAV2 is used for gene delivery, similarly to when plasmid DNA is used for gene delivery.

5-B. Increased Gene Expression by Fragments T3.1.1 and T3.1.2 in In Vivo Gene Delivery Using AAV8

Figure 6B:
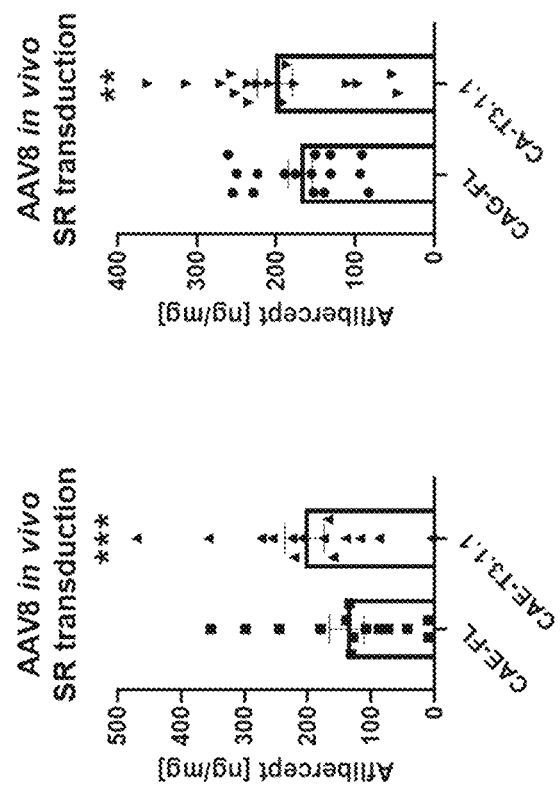

To determine whether the fragment T3.1.1 of EF-1α intron had the ability to efficiently induce gene expression when AAV was used for in vivo gene delivery, the gene expressions in AAV8 constructs including the fragment CA-T3.1.1 and CAE-T3.1.12 were compared with those in AAV8 constructs including CAG-FL and CAE-FL as regulatory sites for gene expression. The AAV8 constructs were designed to express extracellular secretory aflibercept protein (the nucleotide sequence of SEQ ID NO: 26 encoding a hIgG signal peptide was used as a signal peptide sequence). 1×10⁹vg of each AAV8 construct was injected subretinally into both eyes of 8 mice per group. 28 days after injection, the expression of aflibercept in each eye was determined by ELISA. As a result, the expression of aflibercept in the CAE-T3.1.1-administered group was increased by 147.6% compared to that in the CAE-FL group. The expression of aflibercept in the CA-T3.1.1-administered group was increased by 118.7% compared to that in the CAG-FL group (FIG. 6B). These results suggest that the EF-1α intron fragment T3.1.1 can efficiently induce gene expression even in vivo.

Figure 6C:
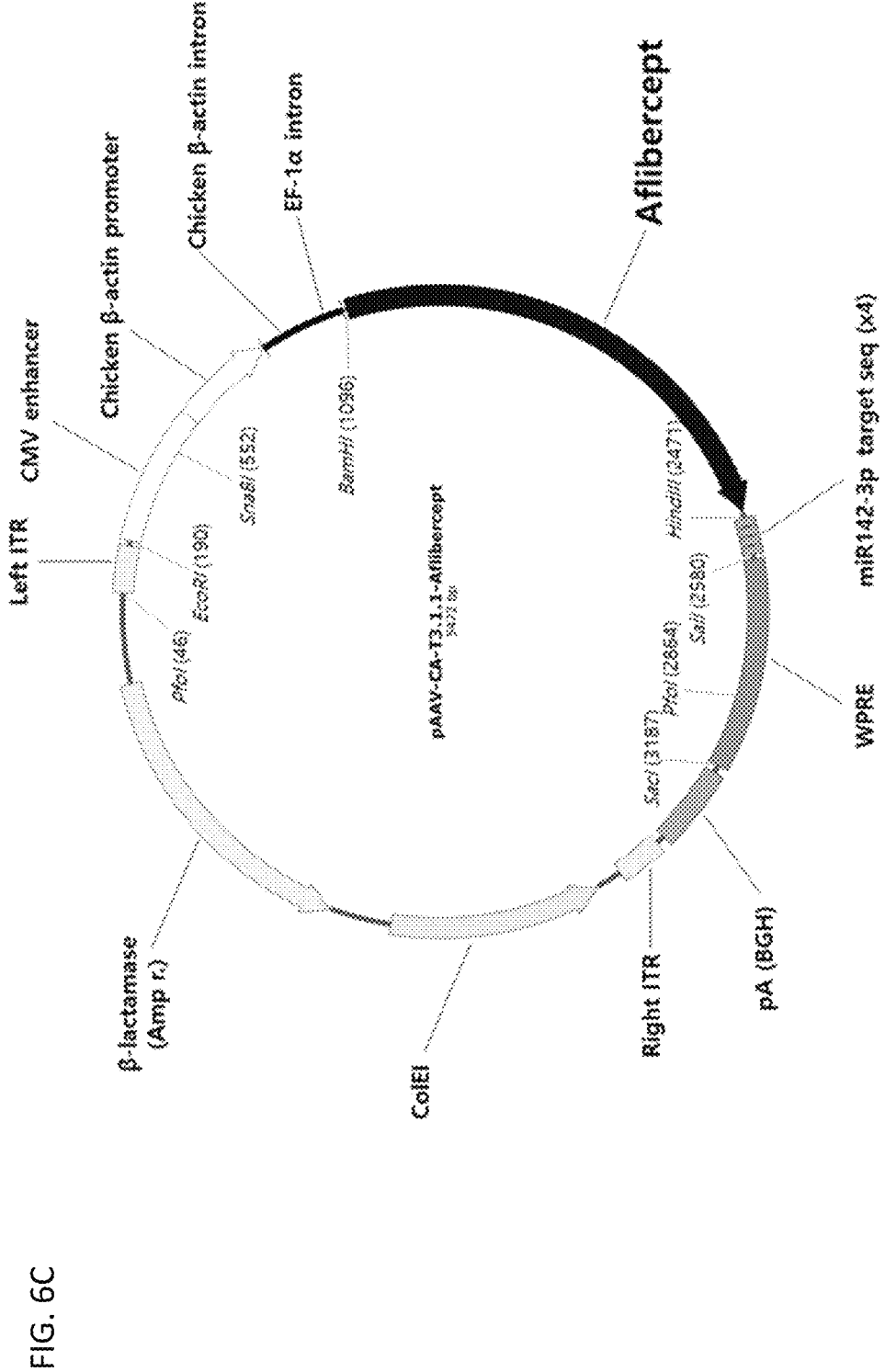

FIG. 6C is a cleavage map of the pAAV-CA-T3.1.1 vector into which aflibercept as a transgene was inserted.

All publications, patents, patent applications and other documents cited in this application are hereby incorporated by reference in their entireties for all purposes to the same extent as if each individual publication, patent, patent application or other document were individually indicated to be incorporated by reference for all purposes.

Although the present disclosure has been described herein with reference to the foregoing aspects, those skilled in the art will appreciate that various changes and modifications are possible by addition, modification, deletion or insertion of the elements without departing from the spirit of the present disclosure as disclosed in the accompanying claims. It is to be understood that such changes and modifications are within the scope of the present disclosure.

What is claimed is:

1. An isolated polynucleotide comprising an elongation factor-1 alpha (EF-1α) intron fragment and a transgene, wherein the EF-1α intron fragment comprises a splice donor sequence directly joined upstream of a nucleotide sequence selected from the group consisting of SEQ ID NOS: 2, 3, 57, 65, 68 and 72, and wherein the splice donor sequence has at least 70% identity with the sequence of SEQ ID NO: 9 or 10.

2. The polynucleotide of claim 1, which further comprises (i) a promoter, (ii) an enhancer, (iii) an exon sequence, (iv) a target sequence for a microRNA (miRNA), (v) a woodchuck hepatitis virus posttranscriptional regulatory element (WPRE) sequence, (vi) a polyadenylation (pA) sequence, or (vii) a combination thereof.

3. The polynucleotide of claim 2,
(i) wherein the transgene encodes a wild type polypeptide or any variant thereof, a fusion protein, an antibody or an antigen-binding fragment thereof, a RNA-based molecule, or any combination thereof;
(ii) wherein the promoter comprises a cytomegalovirus (CMV) promoter, an EF-1a promoter, β-actin promoter, a GAPDH promoter, a HSP70 promoter, a GRP78 promoter, an eIF4a promoter, an AAT promoter, a TTR promoter, a GFAP promoter, a SV40 promoter, a SYN1 promoter, a GRK promoter, a Rho promoter, or a combination thereof;
(iii) wherein the enhancer comprises a cytomegalovirus (CMV) enhancer, a SV40 early enhancer, an adenovirus 5 E1A enhancer, a HBV enhancer-1 regulatory region (Eh-1), a HPV-16 or −18 E6/7 long control region (LCR), a HIV-1 long terminal repeat (LTR), or a combination thereof;
(iv) wherein the exon sequence comprises an EF-1α exon 2 (E2) nucleotide sequence, a cytomegalovirus (CMV) exon 1 (E1) sequence, a EF-1α E1 sequence, a β-actin E1 sequence, or a combination thereof; or
(v) any combination of (i) to (iv).

4. The polynucleotide of claim 3,
(1) wherein the transgene comprises a sequence having at least 70% sequence identity to the nucleotide sequence set forth in SEQ ID NO: 23;
(2) wherein (i) the EF-1α promoter comprises a sequence having at least 70% sequence identity to the nucleotide sequence set forth in SEQ ID NO: 7; (ii) the CMV promoter comprises a sequence having at least 70% sequence identity to the nucleotide sequence set forth in SEQ ID NO: 5 or 6, or (iii) the β-actin promoter comprises a sequence having at least 70% sequence identity to the nucleotide sequence set forth in SEQ ID NO: 8;
(3) wherein the CMV enhancer comprises a sequence having at least 70% sequence identity to the nucleotide sequence set forth in SEQ ID NO: 9 or 10;
(4) wherein the EF-1α exon 2 (E2) nucleotide sequence has at least 70% sequence identity to the nucleotide sequence set forth in SEQ ID NO: 11;
(5) wherein (i) the CMV E1 sequence has at least 70% sequence identity to the nucleotide sequence set forth in SEQ ID NO: 12; (ii) the EF-1α E1 sequence has at least 70% sequence identity to the nucleotide sequence set forth in SEQ ID NO: 13; or (iii) the β-acting E1 sequence has at least 70% sequence identity to the nucleotide sequence set forth in SEQ ID NO: 14 or 15;
(6) wherein the WRPE sequence has at least 70% sequence identity to the nucleotide sequence set forth in SEQ ID NO: 18;
(7) wherein the pA sequence has at least 70% sequence identity to the nucleotide sequence set forth in any one of SEQ ID NOs: 19 to 22;
(8) wherein the target sequence for a miRNA: (i) is complementary to the full-length or partial sequence of miR142-3p or miR142-5p; (ii) comprises the nucleotide sequence set forth in SEQ ID NO: 16 or SEQ ID NO: 17; or (iii) both (i) and (ii); or
(9) any combination of (1) to (8).

5. A vector comprising the polynucleotide of claim 1.

6. The vector of claim 5, which is a viral vector.

7. An in vitro cell comprising the polynucleotide of claim 1.

8. A method for producing a recombinant virus particle comprising transducing a cell with the vector of claim 5 and a construct containing a rep gene and a cap gene.

9. A recombinant virus particle produced by the method of claim 8.

10. A recombinant virus particle comprising (a) a capsid protein and (b) the vector of claim 5.

11. The recombinant virus particle of claim 10, which is an adeno-associated virus (AVV).

12. A pharmaceutical composition comprising (a) the polynucleotide of claim 1 and (b) a pharmaceutically acceptable excipient.

13. The polynucleotide of claim 1, which does not comprise:
(a) nucleotides 1 to 851 of SEQ ID NO: 1,
(b) nucleotides 1 to 850 of SEQ ID NO: 1,
(c) nucleotides 1 to 829 of SEQ ID NO: 1,
(d) nucleotides 1 to 820 of SEQ ID NO: 1,
(e) nucleotides 1 to 810 of SEQ ID NO: 1,
(f) nucleotides 1 to 807 of SEQ ID NO: 1,
(g) nucleotides 1 to 800 of SEQ ID NO: 1, or
(h) nucleotides 1 to 750 of SEQ ID NO: 1.

14. The polynucleotide of claim 1, which does not comprise nucleotides 721 to 851 of SEQ ID NO: 1.

15. A polynucleotide comprising (i) a transgene and (ii) a control element operably linked to the transgene, wherein the control element comprises from 5' to 3':
1) The CMV enhancer set forth in SEQ ID NO: 4;
2) a promoter selected from the CMV promoter sequence set forth in SEQ ID NO: 5 or 6, the EF-1α promoter sequence set forth in SEQ ID NO: 7, or the chicken β-actin promoter sequence set forth in SEQ ID NO: 8;
3) an exon 1 (E1) sequence selected from the CMV E1 sequence set forth in SEQ ID NO: 12, the EF-1α E1 sequence set forth in SEQ ID NO: 13, or the chicken β-actin E1 sequence set forth in SEQ ID NO: 14 or 15;
4) the splicing donor sequence set forth in SEQ ID NO: 9 or 10 directly joined upstream of a nucleotide sequence selected from the group consisting of SEQ ID NOS: 2 and 3; and
5) the EF-1α E2 sequence set forth in SEQ ID NO: 11.

16. A pharmaceutical composition comprising (a) the polynucleotide of claim 15 and (b) a pharmaceutically acceptable excipient.

17. The polynucleotide of claim 15, wherein:
(a) the transgene comprises the nucleotide sequence set forth in SEQ ID NO: 23;
(b) the promoter is the chicken β-actin promoter sequence set forth in SEQ ID NO: 8;

(c) the E1 sequence is the chicken β-actin E1 sequence set forth in SEQ ID NO: 15; and
(d) the splicing donor sequence is the splicing donor sequence set forth in SEQ ID NO: 10.

* * * * *

SEQUENCE LISTING

```
<160> NUMBER OF SEQ ID NOS: 76

<210> SEQ ID NO 1
<211> LENGTH: 924
<212> TYPE: DNA
<213> ORGANISM: Artificial Sequence
<220> FEATURE:
<223> OTHER INFORMATION: EF-1 alpha intron FL

<400> SEQUENCE: 1
cccgcgggcc tggcctcttt acgggttatg gcccttgcgt gccttgaatt acttccacgc      60
ccctggctgc agtacgtgat tcttgatccc gagcttcggg ttggaagtgg gtgggagagt     120
tcgaggcctt gcgcttaagg agccccttcg cctcgtgctt gagttgaggc ctggcttggg     180 cgctgggggcc gccgcgtgcg aatctggtgg caccttcgcg cctgtctcgc tgctttcgat     240
aagtctctag ccatttaaaa ttttttgatga cctgctgcga cgcttttttt ctggcaagat     300
agtcttgtaa atgcgggcca agatctgcac actggtattt cggttttttgg ggccgcgggc     360 ggcgacgggg cccgtgcgtc ccagcgcaca tgttcggcga ggcggggcct gcgagcgcgg     420
ccaccgagaa tcggacgggg gtagtctcaa gctggccggc ctgctctggt gcctggcctc     480
gcgccgccgt gtatcgcccc gccctgggcg gcaaggctgg cccggtcggc accagttgcg     540
tgagcggaaa gatggccgct tcccggccct gctgcaggga gctcaaaatg gaggacgcgg     600 cgctcggagag agcgggcggg tgagtcaccc acacaaagga aaagggcctt tccgtcctca     660
gccgtcgctt catgtgactc cacggagtac cgggcgccgt ccaggcacct cgattagttc     720
tcgagctttt ggagtacgtc gtctttaggt tggggggagg ggttttatgc gatggagttt     780
ccccacactg agtgggtgga gactgaagtt aggccagctt ggcacttgat gtaattctcc     840
ttggaatttg cccttttttga gtttggatct tggttcattc tcaagcctca gacagtggtt     900
caaagttttt ttcttccatt tcag                                           924

<210> SEQ ID NO 2
<211> LENGTH: 95
<212> TYPE: DNA
<213> ORGANISM: Artificial Sequence
<220> FEATURE:
<223> OTHER INFORMATION: EF-1 alpha intron fragment T3.1.1

<400> SEQUENCE: 2
tgtaattctc cttggaattt gccctttttg agtttggatc ttggttcatt ctcaagcctc      60
agacagtggt tcaaagtttt tttcttccat ttcag                               95

<210> SEQ ID NO 3
```

<211> LENGTH: 73
<212> TYPE: DNA
<213> ORGANISM: Artificial Sequence
<220> FEATURE:
<223> OTHER INFORMATION: EF-1 alpha intron fragment T3.1.2

<400> SEQUENCE: 3

```
ccttttgag tttggatctt ggttcattct caagcctcag acagtggttc aaagttttt      60 tcttccattt cag                                                       73
```

<210> SEQ ID NO 4
<211> LENGTH: 380
<212> TYPE: DNA
<213> ORGANISM: Artificial Sequence
<220> FEATURE:
<223> OTHER INFORMATION: CMV enhancer

<400> SEQUENCE: 4

```
gacattgatt attgactagt tattaatagt aatcaattac ggggtcatta gttcatagcc    60
catatatgga gttccgcgtt acataactta cggtaaatgg cccgcctggc tgaccgccca    120 acgaccccg cccattgacg tcaataatga cgtatgttcc catagtaacg ccaataggga    180
ctttccattg acgtcaatgg gtggagtatt tacggtaaac tgcccacttg gcagtacatc    240
aagtgtatca tatgccaagt acgccccta ttgacgtcaa tgacggtaaa tggcccgcct    300
ggcattatgc ccagtacatg accttatggg actttcctac ttggcagtac atctacgtat    360
tagtcatcgc tattaccatg                                                380
```

<210> SEQ ID NO 5
<211> LENGTH: 31
<212> TYPE: DNA
<213> ORGANISM: Artificial Sequence
<220> FEATURE:
<223> OTHER INFORMATION: CMV promoter fragment

<400> SEQUENCE: 5

```
gtgatgcggt tttggcagta caccaatggg c                                   31
```

<210> SEQ ID NO 6
<211> LENGTH: 218
<212> TYPE: DNA
<213> ORGANISM: Artificial Sequence
<220> FEATURE:
<223> OTHER INFORMATION: CMV promoter

<400> SEQUENCE: 6

```
gtgatgcggt tttggcagta catcaatggg cgtggatagc ggtttgactc acggggattt    60
ccaagtctcc accccattga cgtcaatggg agtttgtttt ggcaccaaaa tcaacgggac    120
tttccaaaat gtcgtaacaa ctccgcccca ttgacgcaaa tgggcggtag cgtgtacgg    180 tgggaggtct atataagcag agctcgttta gtgaaccg                            218
```

<210> SEQ ID NO 7
<211> LENGTH: 201
<212> TYPE: DNA
<213> ORGANISM: Artificial Sequence
<220> FEATURE:
<223> OTHER INFORMATION: EF-1 alpha promoter

<400> SEQUENCE: 7

```
gctccggtgc ccgtcagtgg gcagagcgca catcgcccac agtccccgag aagttggggg    60
gaggggtcgg caattgaacc ggtgcctaga gaaggtggcg cggggtaaac tgggaaagtg    120
```

```
atgtcgtgta ctggctccgc cttttttcccg agggtggggg agaaccgtat ataagtgcag    180
tagtcgccgt gaacgttctt t                                               201
```

<210> SEQ ID NO 8
<211> LENGTH: 279
<212> TYPE: DNA
<213> ORGANISM: Artificial Sequence
<220> FEATURE:
<223> OTHER INFORMATION: Chicken beta-actin promoter

<400> SEQUENCE: 8

```
gtcgaggtga gccccacgtt ctgcttcact ctccccatct cccccccctc cccaccccca     60
attttgtatt tatttatttt ttaattattt tgtgcagcga tggggcgggg gggggggggg    120
gggcgcgcgc caggcggggc ggggcggggc gaggggcggg gcggggcgag gcggagaggt    180
gcggcggcag ccaatcagag cggcgcgctc cgaaagtttc cttttatggc gaggcggcgg    240
cggcggcggc cctataaaaa gcgaagcgcg cggcgggcg                           279
```

<210> SEQ ID NO 9
<211> LENGTH: 19
<212> TYPE: DNA
<213> ORGANISM: Artificial Sequence
<220> FEATURE:
<223> OTHER INFORMATION: EF-1 alpha splicing donor

<400> SEQUENCE: 9

```
gtaagtgccg tgtgtggtt                                                  19
```

<210> SEQ ID NO 10
<211> LENGTH: 43
<212> TYPE: DNA
<213> ORGANISM: Artificial Sequence
<220> FEATURE:
<223> OTHER INFORMATION: Chicken beta-actin splicing donor

<400> SEQUENCE: 10

```
gtgagcgggc gggacggccc ttctcctccg ggctgtaatt agc                       43
```

<210> SEQ ID NO 11
<211> LENGTH: 9
<212> TYPE: DNA
<213> ORGANISM: Artificial Sequence
<220> FEATURE:
<223> OTHER INFORMATION: EF-1 alpha exon 2 fragment

<400> SEQUENCE: 11

```
gtgtcgtga                                                              9
```

<210> SEQ ID NO 12
<211> LENGTH: 30
<212> TYPE: DNA
<213> ORGANISM: Artificial Sequence
<220> FEATURE:
<223> OTHER INFORMATION: CMV exon 1 fragment

<400> SEQUENCE: 12

```
tcagatcgcc tggagacgcc atccacgctg                                      30
```

<210> SEQ ID NO 13
<211> LENGTH: 29
<212> TYPE: DNA
<213> ORGANISM: Artificial Sequence
<220> FEATURE:

```
<223> OTHER INFORMATION: EF-1 alpha exon 1 fragment

<400> SEQUENCE: 13
ttcgcaacgg gtttgccgcc agaacacag                                           29

<210> SEQ ID NO 14
<211> LENGTH: 32
<212> TYPE: DNA
<213> ORGANISM: Artificial Sequence
<220> FEATURE:
<223> OTHER INFORMATION: Chicken beta-actin exon 1 fragment 1

<400> SEQUENCE: 14
ggagtcgctg cgcgctgcct tcgccccgtg cc                                       32

<210> SEQ ID NO 15
<211> LENGTH: 93
<212> TYPE: DNA
<213> ORGANISM: Artificial Sequence
<220> FEATURE:
<223> OTHER INFORMATION: Chicken beta-actin exon 1 fragment 2

<400> SEQUENCE: 15
ggagtcgctg cgcgctgcct tcgccccgtg ccccgctccg ccgccgcctc gcgccgcccg         60
ccccggctct gactgaccgc gttactccca cag                                      93

<210> SEQ ID NO 16
<211> LENGTH: 23
<212> TYPE: DNA
<213> ORGANISM: Artificial Sequence
<220> FEATURE:
<223> OTHER INFORMATION: miR142-3p target sequence

<400> SEQUENCE: 16
tccataaagt aggaaacact aca                                                 23

<210> SEQ ID NO 17
<211> LENGTH: 104
<212> TYPE: DNA
<213> ORGANISM: Artificial Sequence
<220> FEATURE:
<223> OTHER INFORMATION: Four repeats of miR142-3p target sequence with
      spacer

<400> SEQUENCE: 17
tccataaagt aggaaacact acacgattcc ataaagtagg aaacactaca acgttccata         60
aagtaggaaa cactacatca ctccataaag taggaaacac taca                          104

<210> SEQ ID NO 18
<211> LENGTH: 589
<212> TYPE: DNA
<213> ORGANISM: Artificial Sequence
<220> FEATURE:
<223> OTHER INFORMATION: WPRE

<400> SEQUENCE: 18
aatcaacctc tggattacaa aatttgtgaa agattgactg gtattcttaa ctatgttgct         60
ccttttacgc tatgtggata cgctgcttta atgcctttgt atcatgctat tgcttcccgt        120
atggctttca ttttctcctc cttgtataaa tcctggttgc tgtctcttta tgaggagttg        180
tggcccgttg tcaggcaacg tggcgtggtg tgcactgtgt ttgctgacgc aaccccact         240 ggttggggca ttgccaccac ctgtcagctc ctttccggga ctttcgcttt ccccctccct        300
```

```
attgccacgg cggaactcat cgccgcctgc cttgcccgct gctggacagg ggctcggctg      360
ttgggcactg acaattccgt ggtgttgtcg gggaagctga cgtcctttcc atggctgctc      420
gcctgtgttg ccacctggat tctgcgcggg acgtccttct gctacgtccc ttcggccctc      480
aatccagcgg accttccttc ccgcggcctg ctgccggctc tgcggcctct tccgcgtctt      540
cgccttcgcc ctcagacgag tcggatctcc ctttgggccg cctccccgc                  589

<210> SEQ ID NO 19
<211> LENGTH: 477
<212> TYPE: DNA
<213> ORGANISM: Artificial Sequence
<220> FEATURE:
<223> OTHER INFORMATION: hGH pA sequence

<400> SEQUENCE: 19
gggtggcatc cctgtgaccc ctccccagtg cctctcctgg ccctggaagt tgccactcca       60
gtgcccacca gccttgtcct aataaaatta gttgcatca ttttgtctga ctaggtgtcc      120
ttctataata ttatggggtg agggggggtg gtatggagca aggggcaagt tgggaagaca      180
acctgtaggg cctgcggggt ctattgggaa ccaagctgga gtgcagtggc acaatcttgg      240
ctcactgcaa tctccgcctc ctgggttcaa gcgattctcc tgcctcagcc tcccgagttg      300
ttgggattcc aggcatgcat gaccaggctc agctaatttt tgttttttg gtagagacgg      360 ggtttcacca tattggccag gctggtctcc aactcctaat ctcaggtgat ctacccacct      420
tggcctccca aattgctggg attacaggcg tgaaccactg ctcccttccc tgtccttt      477

<210> SEQ ID NO 20
<211> LENGTH: 225
<212> TYPE: DNA
<213> ORGANISM: Artificial Sequence
<220> FEATURE:
<223> OTHER INFORMATION: bGH pA sequence

<400> SEQUENCE: 20
ctgtgccttc tagttgccag ccatctgttg tttgccctc ccccgtgcct tccttgaccc       60
tggaaggtgc cactcccact gtcctttcct aataaaatga ggaaattgca tcgcattgtc      120
tgagtaggtg tcattctatt ctggggggtg ggtgggca ggacagcaag ggggaggatt      180
gggaagacaa tagcaggcat gctggggatg cggtgggctc tatgg                     225

<210> SEQ ID NO 21
<211> LENGTH: 122
<212> TYPE: DNA
<213> ORGANISM: Artificial Sequence
<220> FEATURE:
<223> OTHER INFORMATION: SV40 early pA sequence

<400> SEQUENCE: 21
aacttgttta ttgcagctta taatggttac aaataaagca atagcatcac aaatttcaca       60
aataaagcat ttttttcact gcattctagt tgtggtttgt ccaaactcat caatgtatct      120
ta                                                                    122

<210> SEQ ID NO 22
<211> LENGTH: 134
<212> TYPE: DNA
<213> ORGANISM: Artificial Sequence
<220> FEATURE:
<223> OTHER INFORMATION: SV40 late pA sequence

<400> SEQUENCE: 22
```

```
atgctttatt tgtgaaattt gtgatgctat tgctttattt gtaaccatta taagctgcaa    60
taaacaagtt aacaacaaca attgcattca ttttatgttt caggttcagg gggaggtgtg   120
ggaggttttt taaa                                                     134
```

<210> SEQ ID NO 23
<211> LENGTH: 1296
<212> TYPE: DNA
<213> ORGANISM: Artificial Sequence
<220> FEATURE:
<223> OTHER INFORMATION: Aflibercept

<400> SEQUENCE: 23

```
tctgataccg gcagacccct cgtggaaatg tacagcgaga tccccgagat catccacatg    60
accgagggca gagagctggt catcccttgc agagtgacaa gccccaacat caccgtgaca   120
ctgaagaagt tccctctgga cacactgatc cccgacggca gagaatcat ctgggacagc    180 cggaagggct catcatcag caacgccacc tacaaagaga tcggcctgct gacatgcgag    240
gccacagtga atggccacct gtacaagacc aactacctga cacacagaca gaccaacacc    300
atcatcgacg tggtgctgag ccccttctcac ggcattgagc tgtctgtggg agagaagctg   360
gtgctgaatt gcaccgccag aaccgagctg aacgtgggca tcgacttcaa ctgggagtac   420
cccagcagca gcaccagca caagaaactg gtcaaccggg acctgaaaac ccagagcggc    480
agcgagatga agaaattcct gagcaccctg accatcgacg gcgtgacaag aagcgatcag    540
ggcctgtaca catgtgccgc cagctctggc ctgatgacca gaaaaaacag caccttcgtg    600
cgggtgcacg agaaggacaa gacccacaca tgtcctccat gtcctgctcc agaactgctc    660
ggcggaccct ccgttttcct gtttccacct aagcctaagg acaccctgat gatcagcaga    720 accccctgaag tgacctgcgt ggtggtggat gtgtctcacg aggaccccga agtgaagttc    780
aattggtacg tggacggcgt ggaagtgcac aacgccaaga ccaagcctag agaggaacag    840
tacaactcca catacagagt ggtgtccgtg ctgaccgtgc tgcaccagga ttggctgaac    900
ggcaaagagt acaagtgcaa ggtgtccaac aaggccctgc ctgctcctat cgagaaaacc    960
atctccaagg ccaagggcca gccaagagaa ccccaggttt acacactgcc tccaagcagg  1020
gacgagctga caaagaatca ggtgtccctg acctgcctgg tcaagggctt ctacccttcc  1080
gatatcgccg tggaatggga gagcaatggc cagcctgaga caactacaa gcaacccct     1140 cctgtgctgg acagcgacgg ctcattcttc ctgtacagca agctgacagt ggacaagagc  1200
agatggcagc agggcaacgt gttcagctgt tctgtgatgc acgaggccct gcacaaccac  1260
tacacccaga gtctctgag cttgtctcct ggctaa                              1296
```

<210> SEQ ID NO 24
<211> LENGTH: 30
<212> TYPE: DNA
<213> ORGANISM: Artificial Sequence
<220> FEATURE:
<223> OTHER INFORMATION: Oligo #001

<400> SEQUENCE: 24

```
ggaagatctc tgtgccttct agttgccagc                                     30
```

<210> SEQ ID NO 25
<211> LENGTH: 31
<212> TYPE: DNA
<213> ORGANISM: Artificial Sequence
<220> FEATURE:

<223> OTHER INFORMATION: Oligo #002

<400> SEQUENCE: 25
cacgtggtta ccccatagag cccaccgcat c                                31

<210> SEQ ID NO 26
<211> LENGTH: 61
<212> TYPE: DNA
<213> ORGANISM: Artificial Sequence
<220> FEATURE:
<223> OTHER INFORMATION: Oligo #003

<400> SEQUENCE: 26
agctttccat aaagtaggaa acactacacg attccataaa gtaggaaaca ctacaacgtt    60
c                                                                  61

<210> SEQ ID NO 27
<211> LENGTH: 48
<212> TYPE: DNA
<213> ORGANISM: Artificial Sequence
<220> FEATURE:
<223> OTHER INFORMATION: Oligo #004

<400> SEQUENCE: 27
tagtgtttcc tactttatgg aatcgtgtag tgtttcctac tttatgga               48

<210> SEQ ID NO 28
<211> LENGTH: 49
<212> TYPE: DNA
<213> ORGANISM: Artificial Sequence
<220> FEATURE:
<223> OTHER INFORMATION: Oligo #005

<400> SEQUENCE: 28
cataaagtag gaaacactac atcactccat aaagtaggaa acactacag              49

<210> SEQ ID NO 29
<211> LENGTH: 61
<212> TYPE: DNA
<213> ORGANISM: Artificial Sequence
<220> FEATURE:
<223> OTHER INFORMATION: Oligo #006

<400> SEQUENCE: 29
tcgactgtag tgtttcctac tttatggagt gatgtagtgt ttcctacttt atggaacgtt    60
g                                                                  61

<210> SEQ ID NO 30
<211> LENGTH: 31
<212> TYPE: DNA
<213> ORGANISM: Artificial Sequence
<220> FEATURE:
<223> OTHER INFORMATION: Oligo #007

<400> SEQUENCE: 30
gtgtgtggtt tgctgcaggg agctcaaaat g                                31

<210> SEQ ID NO 31
<211> LENGTH: 20
<212> TYPE: DNA
<213> ORGANISM: Artificial Sequence
<220> FEATURE:
<223> OTHER INFORMATION: Oligo #008

<400> SEQUENCE: 31
cggtgatgac ggtgaaaacc                                                     20

<210> SEQ ID NO 32
<211> LENGTH: 30
<212> TYPE: DNA
<213> ORGANISM: Artificial Sequence
<220> FEATURE:
<223> OTHER INFORMATION: Oligo #009

<400> SEQUENCE: 32
ccctgcagca aaccacacac ggcacttacc                                          30

<210> SEQ ID NO 33
<211> LENGTH: 20
<212> TYPE: DNA
<213> ORGANISM: Artificial Sequence
<220> FEATURE:
<223> OTHER INFORMATION: Oligo #010

<400> SEQUENCE: 33
ggttttcacc gtcatcaccg                                                     20

<210> SEQ ID NO 34
<211> LENGTH: 31
<212> TYPE: DNA
<213> ORGANISM: Artificial Sequence
<220> FEATURE:
<223> OTHER INFORMATION: Oligo #011

<400> SEQUENCE: 34
gtgtgtggtt tcgagctttt ggagtacgtc g                                        31

<210> SEQ ID NO 35
<211> LENGTH: 30
<212> TYPE: DNA
<213> ORGANISM: Artificial Sequence
<220> FEATURE:
<223> OTHER INFORMATION: Oligo #012

<400> SEQUENCE: 35
aaaagctcga aaccacacac ggcacttacc                                          30

<210> SEQ ID NO 36
<211> LENGTH: 28
<212> TYPE: DNA
<213> ORGANISM: Artificial Sequence
<220> FEATURE:
<223> OTHER INFORMATION: Oligo #013

<400> SEQUENCE: 36
gtgtgtggtt gttaggccag cttggcac                                            28

<210> SEQ ID NO 37
<211> LENGTH: 30
<212> TYPE: DNA
<213> ORGANISM: Artificial Sequence
<220> FEATURE:
<223> OTHER INFORMATION: Oligo #014

<400> SEQUENCE: 37
ctggcctaac aaccacacac ggcacttacc                                          30

<210> SEQ ID NO 38
<211> LENGTH: 33
<212> TYPE: DNA

```
<213> ORGANISM: Artificial Sequence
<220> FEATURE:
<223> OTHER INFORMATION: Oligo #015

<400> SEQUENCE: 38
gtgtgtggtt tcattctcaa gcctcagaca gtg                                   33

<210> SEQ ID NO 39
<211> LENGTH: 30
<212> TYPE: DNA
<213> ORGANISM: Artificial Sequence
<220> FEATURE:
<223> OTHER INFORMATION: Oligo #016

<400> SEQUENCE: 39
ttgagaatga aaccacacac ggcacttacc                                       30

<210> SEQ ID NO 40
<211> LENGTH: 40
<212> TYPE: DNA
<213> ORGANISM: Artificial Sequence
<220> FEATURE:
<223> OTHER INFORMATION: Oligo #017

<400> SEQUENCE: 40
gtgtgtggtt tggttcaaag ttttttttctt ccatttcagg                           40

<210> SEQ ID NO 41
<211> LENGTH: 30
<212> TYPE: DNA
<213> ORGANISM: Artificial Sequence
<220> FEATURE:
<223> OTHER INFORMATION: Oligo #018

<400> SEQUENCE: 41
ctttgaacca aaccacacac ggcacttacc                                       30

<210> SEQ ID NO 42
<211> LENGTH: 52
<212> TYPE: DNA
<213> ORGANISM: Artificial Sequence
<220> FEATURE:
<223> OTHER INFORMATION: Oligo #019

<400> SEQUENCE: 42
ccggaattct gacattgatt attgactagt tattaatagt aatcaattac gg              52

<210> SEQ ID NO 43
<211> LENGTH: 28
<212> TYPE: DNA
<213> ORGANISM: Artificial Sequence
<220> FEATURE:
<223> OTHER INFORMATION: Oligo #020

<400> SEQUENCE: 43
cgcggatccc tgtgttctgg cggcaaac                                         28

<210> SEQ ID NO 44
<211> LENGTH: 39
<212> TYPE: DNA
<213> ORGANISM: Artificial Sequence
<220> FEATURE:
<223> OTHER INFORMATION: Oligo #021

<400> SEQUENCE: 44
cgcggatccc ggttcactaa acgagctctg cttatatag                             39
```

<210> SEQ ID NO 45
<211> LENGTH: 30
<212> TYPE: DNA
<213> ORGANISM: Artificial Sequence
<220> FEATURE:
<223> OTHER INFORMATION: Oligo #022

<400> SEQUENCE: 45
tgtaattctc cttggaattt gcccttttg                              30

<210> SEQ ID NO 46
<211> LENGTH: 32
<212> TYPE: DNA
<213> ORGANISM: Artificial Sequence
<220> FEATURE:
<223> OTHER INFORMATION: Oligo #023

<400> SEQUENCE: 46
cccaagcttg gatcctcacg acacctgaaa tg                          32

<210> SEQ ID NO 47
<211> LENGTH: 89
<212> TYPE: DNA
<213> ORGANISM: Artificial Sequence
<220> FEATURE:
<223> OTHER INFORMATION: Oligo #024

<400> SEQUENCE: 47 ccttttgag tttggatctt ggttcattct caagcctcag acagtggttc aaagttttt    60 tcttccattt caggtgtcgt gaggatcca                                    89

<210> SEQ ID NO 48
<211> LENGTH: 93
<212> TYPE: DNA
<213> ORGANISM: Artificial Sequence
<220> FEATURE:
<223> OTHER INFORMATION: Oligo #025

<400> SEQUENCE: 48
agcttggatc ctcacgacac ctgaaatgga agaaaaaaac tttgaaccac tgtctgaggc  60
ttgagaatga accaagatcc aaactcaaaa agg                              93

<210> SEQ ID NO 49
<211> LENGTH: 27
<212> TYPE: DNA
<213> ORGANISM: Artificial Sequence
<220> FEATURE:
<223> OTHER INFORMATION: Oligo #026

<400> SEQUENCE: 49
cggggtacct tcgcaacggg tttgccg                                27

<210> SEQ ID NO 50
<211> LENGTH: 21
<212> TYPE: DNA
<213> ORGANISM: Artificial Sequence
<220> FEATURE:
<223> OTHER INFORMATION: Oligo #027

<400> SEQUENCE: 50
cgcggatcct cacgacacct g                                      21

<210> SEQ ID NO 51

```
<211> LENGTH: 26
<212> TYPE: DNA
<213> ORGANISM: Artificial Sequence
<220> FEATURE:
<223> OTHER INFORMATION: Oligo #028

<400> SEQUENCE: 51
tgaggatccg ccaccatgga gtttgg                                            26

<210> SEQ ID NO 52
<211> LENGTH: 49
<212> TYPE: DNA
<213> ORGANISM: Artificial Sequence
<220> FEATURE:
<223> OTHER INFORMATION: Oligo #029

<400> SEQUENCE: 52
cgcaagcttc agtagcgctt tagccaggag acaagctcag agacttctg                   49

<210> SEQ ID NO 53
<211> LENGTH: 21
<212> TYPE: DNA
<213> ORGANISM: Artificial Sequence
<220> FEATURE:
<223> OTHER INFORMATION: Oligo #030

<400> SEQUENCE: 53 ggaacccta gtgatggagt t                                                  21

<210> SEQ ID NO 54
<211> LENGTH: 16
<212> TYPE: DNA
<213> ORGANISM: Artificial Sequence
<220> FEATURE:
<223> OTHER INFORMATION: Oligo #031

<400> SEQUENCE: 54
cggcctcagt gagcga                                                       16

<210> SEQ ID NO 55
<211> LENGTH: 21
<212> TYPE: DNA
<213> ORGANISM: Artificial Sequence
<220> FEATURE:
<223> OTHER INFORMATION: Oligo #032

<400> SEQUENCE: 55
cactccctct ctgcgcgctc g                                                 21

<210> SEQ ID NO 56
<211> LENGTH: 57
<212> TYPE: DNA
<213> ORGANISM: Artificial Sequence
<220> FEATURE:
<223> OTHER INFORMATION: hIgG signal peptide sequence

<400> SEQUENCE: 56
atggagtttg ggctgagctg ggttttcctc gttgctcttt ttagaggtgt ccagtgt          57

<210> SEQ ID NO 57
<211> LENGTH: 51
<212> TYPE: DNA
<213> ORGANISM: artificial sequence
<220> FEATURE:
<223> OTHER INFORMATION: EF-1 alpha intron fragment T3.2

<400> SEQUENCE: 57
```

```
ttcattctca agcctcagac agtggttcaa agttttttc ttccatttca g         51
```

<210> SEQ ID NO 58
<211> LENGTH: 54
<212> TYPE: DNA
<213> ORGANISM: artificial sequence
<220> FEATURE:
<223> OTHER INFORMATION: EF-1 alpha intron fragment

<400> SEQUENCE: 58

```
tggttcattc tcaagcctca gacagtggtt caaagttttt ttcttccatt tcag     54
```

<210> SEQ ID NO 59
<211> LENGTH: 64
<212> TYPE: DNA
<213> ORGANISM: artificial sequence
<220> FEATURE:
<223> OTHER INFORMATION: EF-1 alpha intron fragment

<400> SEQUENCE: 59

```
gtttggatct tggttcattc tcaagcctca gacagtggtt caaagttttt ttcttccatt   60
tcag                                                                64
```

<210> SEQ ID NO 60
<211> LENGTH: 73
<212> TYPE: DNA
<213> ORGANISM: artificial sequence
<220> FEATURE:
<223> OTHER INFORMATION: EF-1 alpha intron fragment

<400> SEQUENCE: 60

```
ccttttgag tttggatctt ggttcattct caagcctcag acagtggttc aaagtttttt   60
tcttccattt cag                                                     73
```

<210> SEQ ID NO 61
<211> LENGTH: 74
<212> TYPE: DNA
<213> ORGANISM: artificial sequence
<220> FEATURE:
<223> OTHER INFORMATION: EF-1 alpha intron fragment

<400> SEQUENCE: 61

```
ccctttttga gtttggatct tggttcattc tcaagcctca gacagtggtt caaagttttt   60
ttcttccatt tcag                                                     74
```

<210> SEQ ID NO 62

<400> SEQUENCE: 62

000

<210> SEQ ID NO 63
<211> LENGTH: 104
<212> TYPE: DNA
<213> ORGANISM: artificial sequence
<220> FEATURE:
<223> OTHER INFORMATION: EF-1 alpha intron fragment

<400> SEQUENCE: 63

```
ggcacttgat gtaattctcc ttggaatttg ccctttttga gtttggatct tggttcattc   60
tcaagcctca gacagtggtt caaagttttt ttcttccatt tcag                   104
```

```
<210> SEQ ID NO 64
<211> LENGTH: 114
<212> TYPE: DNA
<213> ORGANISM: artificial sequence
<220> FEATURE:
<223> OTHER INFORMATION: EF-1 alpha intron fragment

<400> SEQUENCE: 64
aggccagctt ggcacttgat gtaattctcc ttggaatttg ccctttttga gtttggatct    60
tggttcattc tcaagcctca gacagtggtt caaagttttt tcttccatt tcag          114

<210> SEQ ID NO 65
<211> LENGTH: 117
<212> TYPE: DNA
<213> ORGANISM: artificial sequence
<220> FEATURE:
<223> OTHER INFORMATION: EF-1 alpha intron fragment

<400> SEQUENCE: 65
gttaggccag cttggcactt gatgtaattc tccttggaat tgccctttt tgagtttgga    60 tcttggttca ttctcaagcc tcagacagtg gttcaaagtt ttttcttcc atttcag      117

<210> SEQ ID NO 66
<211> LENGTH: 124
<212> TYPE: DNA
<213> ORGANISM: artificial sequence
<220> FEATURE:
<223> OTHER INFORMATION: EF-1 alpha intron fragment

<400> SEQUENCE: 66
gactgaagtt aggccagctt ggcacttgat gtaattctcc ttggaatttg ccctttttga    60
gtttggatct tggttcattc tcaagcctca gacagtggtt caaagttttt tcttccatt   120 tcag                                                                124

<210> SEQ ID NO 67
<211> LENGTH: 174
<212> TYPE: DNA
<213> ORGANISM: artificial sequence
<220> FEATURE:
<223> OTHER INFORMATION: EF-1 alpha intron fragment

<400> SEQUENCE: 67 tgggggagg ggttttatgc gatggagttt ccccacactg agtgggtgga gactgaagtt     60
aggccagctt ggcacttgat gtaattctcc ttggaatttg ccctttttga gtttggatct   120
tggttcattc tcaagcctca gacagtggtt caaagttttt tcttccatt tcag          174

<210> SEQ ID NO 68
<211> LENGTH: 204
<212> TYPE: DNA
<213> ORGANISM: artificial sequence
<220> FEATURE:
<223> OTHER INFORMATION: EF-1 alpha intron fragment

<400> SEQUENCE: 68
tcgagctttt ggagtacgtc gtctttaggt tgggggagg ggttttatgc gatggagttt     60
ccccacactg agtgggtgga gactgaagtt aggccagctt ggcacttgat gtaattctcc   120
ttggaatttg ccctttttga gtttggatct tggttcattc tcaagcctca gacagtggtt   180
caaagttttt tcttccatt tcag                                            204

<210> SEQ ID NO 69
```

```
<211> LENGTH: 224
<212> TYPE: DNA
<213> ORGANISM: artificial sequence
<220> FEATURE:
<223> OTHER INFORMATION: EF-1 alpha intron fragment

<400> SEQUENCE: 69
ccaggcacct cgattagttc tcgagctttt ggagtacgtc gtctttaggt tgggggagg      60 ggttttatgc gatggagttt ccccacactg agtgggtgga gactgaagtt aggccagctt   120
ggcacttgat gtaattctcc ttggaatttg ccctttttga gtttggatct tggttcattc   180
tcaagcctca gacagtggtt caaagttttt ttcttccatt tcag                     224

<210> SEQ ID NO 70
<211> LENGTH: 274
<212> TYPE: DNA
<213> ORGANISM: artificial sequence
<220> FEATURE:
<223> OTHER INFORMATION: EF-1 alpha intron fragment

<400> SEQUENCE: 70
tccgtcctca gccgtcgctt catgtgactc cacggagtac cgggcgccgt ccaggcacct    60
cgattagttc tcgagctttt ggagtacgtc gtctttaggt tgggggagg ggttttatgc    120 gatggagttt ccccacactg agtgggtgga gactgaagtt aggccagctt ggcacttgat   180
gtaattctcc ttggaatttg ccctttttga gtttggatct tggttcattc tcaagcctca   240
gacagtggtt caaagttttt ttcttccatt tcag                                274

<210> SEQ ID NO 71
<211> LENGTH: 324
<212> TYPE: DNA
<213> ORGANISM: artificial sequence
<220> FEATURE:
<223> OTHER INFORMATION: EF-1 alpha intron fragment

<400> SEQUENCE: 71
cgctcgggag agcgggcggg tgagtcaccc acacaaagga aagggccctt tccgtcctca    60
gccgtcgctt catgtgactc cacggagtac cgggcgccgt ccaggcacct cgattagttc   120
tcgagctttt ggagtacgtc gtctttaggt tgggggagg ggttttatgc gatggagttt   180
ccccacactg agtgggtgga gactgaagtt aggccagctt ggcacttgat gtaattctcc   240
ttggaatttg ccctttttga gtttggatct tggttcattc tcaagcctca gacagtggtt   300
caaagttttt ttcttccatt tcag                                            324

<210> SEQ ID NO 72
<211> LENGTH: 355
<212> TYPE: DNA
<213> ORGANISM: artificial sequence
<220> FEATURE:
<223> OTHER INFORMATION: EF-1 alpha intron fragment

<400> SEQUENCE: 72
tgctgcaggg agctcaaaat ggaggacgcg gcgctcggga gagcgggcgg gtgagtcacc    60
cacacaaagg aaagggcct ttccgtcctc agccgtcgct tcatgtgact ccacggagta   120
ccgggcgccg tccaggcacc tcgattagtt ctcgagcttt tggagtacgt cgtctttagg   180 ttgggggag gggttttatg cgatggagtt tccccacact gagtgggtgg agactgaagt   240
taggccagct tggcacttga tgtaattctc cttggaattt gccctttttg agtttggatc   300
ttggttcatt ctcaagcctc agacagtggt tcaaagtttt ttcttccat ttcag          355
```

<210> SEQ ID NO 73
<211> LENGTH: 374
<212> TYPE: DNA
<213> ORGANISM: artificial sequence
<220> FEATURE:
<223> OTHER INFORMATION: EF-1 alpha intron fragment

<400> SEQUENCE: 73

```
gatggccgct tcccggccct gctgcaggga gctcaaaatg gaggacgcgg cgctcgggag      60
agcgggcggg tgagtcaccc acacaaagga aagggccttt ccgtcctca gccgtcgctt      120 catgtgactc cacggagtac cgggcgccgt ccaggcacct cgattagttc tcgagctttt    180
ggagtacgtc gtctttaggt tggggggagg ggttttatgc gatggagttt ccccacactg    240
agtgggtgga gactgaagtt aggccagctt ggcacttgat gtaattctcc ttggaatttg    300 cccttttga gtttggatct tggttcattc tcaagcctca gacagtggtt caaagttttt     360
ttcttccatt tcag                                                      374
```

<210> SEQ ID NO 74
<211> LENGTH: 424
<212> TYPE: DNA
<213> ORGANISM: artificial sequence
<220> FEATURE:
<223> OTHER INFORMATION: EF-1 alpha intron fragment

<400> SEQUENCE: 74

```
gccctgggcg gcaaggctgg cccggtcggc accagttgcg tgagcggaaa gatggccgct     60
tcccggccct gctgcaggga gctcaaaatg gaggacgcgg cgctcgggag agcgggcggg    120
tgagtcaccc acacaaagga aagggccttt ccgtcctca gccgtcgctt catgtgactc     180
cacggagtac cgggcgccgt ccaggcacct cgattagttc tcgagctttt ggagtacgtc    240
gtctttaggt tggggggagg ggttttatgc gatggagttt ccccacactg agtgggtgga    300
gactgaagtt aggccagctt ggcacttgat gtaattctcc ttggaatttg cccttttga    360 gtttggatct tggttcattc tcaagcctca gacagtggtt caaagttttt ttcttccatt    420
tcag                                                                 424
```

<210> SEQ ID NO 75
<211> LENGTH: 9
<212> TYPE: DNA
<213> ORGANISM: Artificial Sequence
<220> FEATURE:
<223> OTHER INFORMATION: 5' splice site GT rich domain

<400> SEQUENCE: 75

```
caggtaagt                                                              9
```

<210> SEQ ID NO 76
<211> LENGTH: 29
<212> TYPE: DNA
<213> ORGANISM: Artificial Sequence
<220> FEATURE:
<223> OTHER INFORMATION: consensus BPS polyY/3' splice site

<400> SEQUENCE: 76

```
ggttcaaagt ttttttcttc catttcagg                                       29
```